US012760019B2

(12) United States Patent
Bootsma et al.

(10) Patent No.: US 12,760,019 B2
(45) Date of Patent: Oct. 13, 2026

(54) SIK INHIBITORS

(71) Applicant: Pfizer Inc., New York, NY (US)

(72) Inventors: Andrea Nicole Bootsma, Arlington, MA (US); David Christopher Ebner, Newton, MA (US); Daniel Wei-Shung Kung, Salem, CT (US); Matthew Alexander Perry, Uncasville, CT (US); Daniel Copley Schmitt, Zionsville, IN (US); Joseph Walter Strohbach, Wentzville, MO (US); Atli Thorarensen, Stow, MA (US)

(73) Assignee: Pfizer Inc., New York, NY (US)

( * ) Notice: Subject to any disclaimer, the term of this patent is extended or adjusted under 35 U.S.C. 154(b) by 297 days.

(21) Appl. No.: 18/466,034

(22) Filed: Sep. 13, 2023

(65) Prior Publication Data

US 2024/0124450 A1 Apr. 18, 2024

Related U.S. Application Data

(60) Provisional application No. 63/376,480, filed on Sep. 21, 2022.

(51) Int. Cl.
*C07D 471/04* (2006.01)

(52) U.S. Cl.
CPC .................................. *C07D 471/04* (2013.01)

(58) Field of Classification Search
CPC ............................ C07D 471/04; A61K 31/437
See application file for complete search history.

(56) References Cited

FOREIGN PATENT DOCUMENTS

| | | | |
|---|---|---|---|
| EP | 3985005 | A1 | 4/2022 |
| WO | 2009140128 | A2 | 11/2009 |
| WO | 2019238424 | A1 | 12/2019 |
| WO | 2020239660 | A1 | 12/2020 |
| WO | 2022165529 | A1 | 1/2022 |
| WO | 2022031928 | A1 | 2/2022 |
| WO | 2022165530 | A1 | 8/2022 |

OTHER PUBLICATIONS

Berdeaux, Rebecca, et al., "SIK1 is a class II HDAC kinase that promotes survival of skeletal myocytes", Nature Medicine, May 2007, pp. 597-603, 13(5).

Clark, Kristopher, et al., "Phosphorylation of CRTC3 by the salt-inducible kinases controls the interconversion of classically activated and regulatory macrophages", PNAS, Oct. 2, 2012, pp. 16986-16991, 109(42).

Darling, Nicola, et al., "Inhibition of SIK2 and SIK3 during differentiation enhances the anti-inflammatory phenotype of macrophages", Biochemical Journal, Feb. 2017, pp. 521-537, 474(4).

Darling, Nicola, et al., "Salt-inducible kinases are required for the IL-33-dependent secretion of cytokines and chemokines in mast cells", Journal of Biological Chemistry, Feb. 16, 2021, pp. 100428; 1-12, vol. 296.

Henriksson, Emma, et al., "SIK2 regulates CRTCs, HDAC4 and glucose uptaek in adipocytes", Journal Cell Science, 2015, pp. 472-486, 128(3).

(Continued)

*Primary Examiner* — Sahar Javanmard

(57) ABSTRACT

A compound of formula I having the structure:

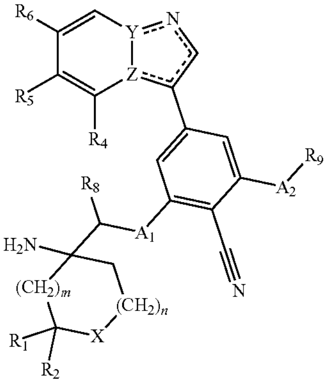

I or a pharmaceutically acceptable salt thereof, wherein $A_1$ and $A_2$ are independently O or S; X is selected from $CH_2$, $CD_2$, $NR_3$, O, and S, where $R_3$ is selected from hydrogen, $C_1$-$C_4$ linear or branched chain alkyl, halo($C_1$-$C_4$)linear or branched chain alkyl, and hydroxyl($C_1$-$C_4$)linear or branched chain alkyl; Y and Z are selected from C and N, where when Y is C, then Z is N, and when Y is N, then Z is C; $R_1$ and $R_2$ are independently selected from hydrogen, deuterium, $C_1$-$C_4$ linear or branched chain alkyl, etc.; or a $C_1$-$C_2$ alkyl substituted with a $C_3$-$C_5$ cycloalkyl ring; or taken together to form a $C_3$-$C_6$ cycloalkyl ring; or where X is $CH_2$ or $CD_2$, then $R_1$ and $R_2$ are independently selected from hydrogen, deuterium, halogen, hydroxyl, $C_1$-$C_4$ linear or branched chain alkyl, etc.; $R_4$ is selected from hydrogen, deuterium, cyano, halogen, ($C_1$-$C_3$) alkoxy, etc.; $R_5$ is selected from hydrogen, deuterium, halogen, $C_1$-$C_3$ alkoxy, amino, ($C_1$-$C_4$ linear or branched chain alkyl)amino, etc.; $R_6$ is selected from hydrogen, deuterium, halogen, $CO_2R_7$ where $R_7$ is selected from H and $C_1$-$C_4$ linear or branched chain alkyl, etc.; $R_8$ is selected from hydrogen, deuterium, and $C_1$-$C_3$ linear or branched chain alkyl; $R_9$ is selected from $C_1$-$C_3$ linear or branched chain alkyl, and a halo($C_1$-$C_3$) linear or branched chain alkyl; and, n and m are independently selected from 0, 1 and 2. The invention also relates to pharmaceutical compositions thereof and therapeutic methods of use therewith.

22 Claims, No Drawings

(56) References Cited

OTHER PUBLICATIONS

Horike, Nanao, et al., "Adipose-specific Expression, Phosphorylation of Ser794 in Insulin Receptor Substrate-1, and Activation in Diabetic Animals of Salt-inducible Kinase-2*", Journal of Biological Chemistry, May 16, 2003, pp. 18440-18447, 278(20).

Katoh, Yoshiko, et al., "Salt-inducible kinase (SIK) isoforms: their involvement in steroidogenesis and adipogenesis", Molecular and Cellular Endocrinology, Mar. 31, 2004, pp. 109-112, 217(1-2).

Ozanne, James, et al., "The clinically approved drugs dasatinib and bosutinib induce anti-inflammatory macrophages by inhibiting the salt-inducible kinases", Biochemical Journal, Jan. 2015, pp. 271-279, 465(2).

Saraiva, Margarida, et al., "Cytokines Focas Biology and therapeutic potential of interleukin-10", Journal of Experimental Medicine, 2020, pp. e20190418, 217(1).

Sundberg, Thomas B., et al., "Small-molecule screening identifies inhibition of salt-inducible kinases as a therapeutic strategy to enhance immunoregulatory functions of dendritic cells", PNAS, Aug. 26, 2014, pp. 12468-12473, 111(34).

Wang, Zhi-nong, et al., "Cloning of a novel kinase (SIK) of the SNF1/AMPK family from high salt diet-treated rat adrenal1", FEBS Letters, 1999, pp. 135-139, 453(1-2).

SIK INHIBITORS

This application is a U.S. Non-Provisional Patent application under 35 U.S.C. 119 (e) which claims the benefit of U.S. Provisional Patent Application No. 63/376,480, filed on Sep. 21, 2022, under 35 USC 119 (e), the disclosures of which are hereby incorporated by reference in their entirety.

FIELD OF THE INVENTION

The present invention relates to novel Salt-Inducible Kinase (SIK) inhibitors, pharmaceutical compositions comprising such compounds and their use as medicaments. More particularly, the present invention provides novel SIK inhibitors which are useful for the treatment and prevention of intestinal bowel disorder and ulcerative colitis.

BACKGROUND

Protein kinases are a family of enzymes that catalyze the phosphorylation of the hydroxyl sidechains of serine, threonine, or tyrosine amino acids of their protein substrates. The resulting phosphorylated substrates play physiological roles controlling cellular functions including cell signal transduction, metabolism, differentiation, motility, survival, proliferation, and apoptosis. Poorly controlled kinase function has been implicated in a wide range of inflammatory, autoimmune, allergic, fibrotic, oncologic, and metabolic diseases. Therapeutics that inhibit protein kinases have been a successful and effective approach in treating diseases.

Three closely related Salt-Inducible Kinase (SIK) isoforms have been identified: SIK1, SIK2 and SIK3. SIK1 was identified in 1999 (Wang, FEBS Lett. (1999) 453, 135-139) followed by close homologues SIK2 and SIK3 (Horike, J. Biol. Chem. (2003) 278 18440-18447; Katoh, Molecular and Cellular Endocrinology (2004) 217, 109-112). These serine-threonine kinases belong to the AMP-activated Protein Kinase (AMPK) subfamily and are broadly expressed across cell types and tissues.

Characterized substrates of the SIKs are the class 2 Histone Deacetylases (HDAC4, HDAC5, HDAC7 and HDAC9) and the cyclic-AMP-response-element binding protein (CREB) regulated transcriptional co-activators (CRTC2, CRTC3). Phosphorylation of these proteins by the SIK kinases results in their nuclear export and cytoplasmic localization through binding to the 14-3-3s proteins (Berdeaux, Nature Medicine (2007) 13 597-603; Henriksson (2015) J. Cell Sci. 128 472-486; Clark, Proc. Natl. Acad. Sci. U.S.A. (2012) 109 16986-16991). Inactivation or inhibition of the SIK kinases leads to their translocation into the nucleus (Ozanne, Biochemical Journal (2015) 465, 271-279). Once transited into the nucleus, the class 2 HDAC molecules repress the expression of genes, including pro-inflammatory cytokines, chemokines, and other proteins involved in signal transduction and immune response. Thus, inhibition of SIKs has been demonstrated to result in the reduction in pro-inflammatory molecules such as TNF-alpha, IL-6, IL-12, GM-CSF, IL-13, CCL2, CCL3, CCL4 and CCL24 (Ozanne, ibid.; Darling, Biochem. J. (2017) 474 521-537; Darling, J. Biol. Chem. (2021) 296 100428) molecules that are key contributors to the pathology of inflammatory diseases.

Nuclear translocation of the CRTC transcriptional co-activators leads to activation of the transcription factor CREB and induction of CREB-regulated gene expression including the cytokine IL-10. IL-10 is an anti-inflammatory cytokine, its immune-modulating effects are important in regulating immune response and its deficiency associated with disease (Saraiva, Journal of Experimental Medicine (2020) 217 e20190418). Pharmacological inhibition or genetic ablation of SIK kinase activity has been demonstrated to lead to the induction of IL-10 (Clark, ibid.; Sundberg, PNAS (2014) 111 (34) 12468-73; Ozanne, ibid.; Darling, ibid.).

Inhibition of SIK kinases has been demonstrated to result in the concomitant down-regulation of pro-inflammatory and the induction of anti-inflammatory molecules. Therefore, the inhibition of the SIKs may result in the suppression of inflammation and the promotion of an immune tolerogenic, anti-inflammatory phenotype; these factors make the SIK family of kinases targets in disease intervention—diseases including inflammatory bowel disease, rheumatoid arthritis, psoriasis, vitiligo and other immune disorders.

Despite advancements in therapeutics, patients with these diseases still suffer from debilitating symptoms and may struggle to manage their disease with the current treatment options and standard of care. Patients can fail to achieve deep long-term remission, or they can relapse or experience adverse events, or become refractory over time to current therapies.

As a result, there is a significant unmet medical need for effective additional therapies for the treatment of these diseases.

SUMMARY OF THE INVENTION

The present invention provides a compound having the structure of formula I:

I

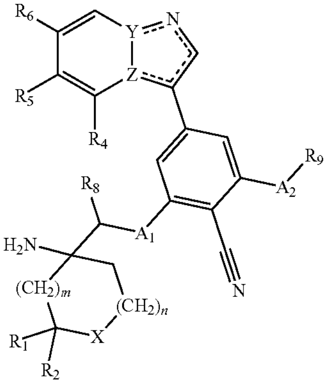

or a pharmaceutically acceptable salt thereof, wherein $A_1$ and $A_2$ are independently O or S;

X is selected from $CH_2$, $CD_2$, $NR_3$, O, and S, where $R_3$ is selected from hydrogen, $C_1$-$C_4$ linear or branched chain alkyl, halo($C_1$-$C_4$)linear or branched chain alkyl, and hydroxyl($C_1$-$C_4$)linear or branched chain alkyl;

Y and Z are selected from C and N, where when Y is C, then Z is N, and when Y is N, then Z is C;

$R_1$ and $R_2$ are independently selected from hydrogen, deuterium, $C_1$-$C_4$ linear or branched chain alkyl, halo ($C_1$-$C_4$)linear or branched chain alkyl, hydroxyl($C_1$-$C_4$)linear or branched chain alkyl, cyano($C_1$-$C_4$)linear or branched chain alkyl, and $C_1$-$C_3$ alkoxy($C_1$-$C_4$) linear or branched chain alkyl; or a $C_1$-$C_2$ alkyl substituted with a $C_3$-$C_5$ cycloalkyl ring; or taken together to form a $C_3$-$C_6$ cycloalkyl ring; or where X is $CH_2$ or $CD_2$, then $R_1$ and $R_2$ are independently selected from hydrogen, deuterium, halogen, hydroxyl, $C_1$-$C_4$ linear or branched chain alkyl, halo($C_1$-$C_4$)linear or branched chain alkyl, hydroxyl($C_1$-$C_4$)linear or branched chain alkyl, cyano($C_1$-$C_4$)linear or branched chain alkyl, and $C_1$-$C_3$ alkoxy($C_1$-$C_4$)linear or branched chain alkyl, and a $C_1$-$C_2$ alkyl substituted with a $C_3$-$C_5$ cycloalkyl ring;

$R_4$ is selected from hydrogen, deuterium, cyano, halogen, ($C_1$-$C_3$) alkoxy, halo($C_1$-$C_3$) alkoxy, $C_1$-$C_3$ alkyl-substituted thiol, $C_1$-$C_4$ linear or branched chain alkyl, halo($C_1$-$C_4$)linear or branched chain alkyl, and a hydroxyl($C_1$-$C_4$)linear or branched chain alkyl;

$R_5$ is selected from hydrogen, deuterium, halogen, $C_1$-$C_3$ alkoxy, amino, ($C_1$-$C_4$ linear or branched chain alkyl) amino, di($C_1$-$C_4$ linear or branched chain alkyl)amino, (4-6 membered)heterocyclic, $C_1$-$C_4$ linear or branched chain alkyl, halo($C_1$-$C_4$)linear or branched chain alkyl, and a hydroxyl($C_1$-$C_4$)linear or branched chain alkyl;

$R_6$ is selected from hydrogen, deuterium, halogen, $C_1$-$C_4$ linear or branched chain alkoxy, $CONH_2$, $C_1$-$C_4$ linear or branched chain alkyl, halo($C_1$-$C_4$)linear or branched chain alkyl, hydroxyl($C_1$-$C_4$)linear or branched chain alkyl, and $CO_2R_7$ where $R_7$ is selected from H and $C_1$-$C_4$ linear or branched chain alkyl;

$R_8$ is selected from hydrogen, deuterium, and $C_1$-$C_3$ linear or branched chain alkyl;

$R_9$ is selected from $C_1$-$C_3$ linear or branched chain alkyl, and a halo($C_1$-$C_3$)linear or branched chain alkyl; and, n and m are independently selected from 0, 1 and 2.

In other aspects, the present invention also provides:

pharmaceutical compositions comprising a pharmaceutically acceptable carrier and a compound of formula I, or a pharmaceutically acceptable salt thereof.

In other aspects, the present invention also provides methods for treating conditions or disorders including:

Arthritis, including rheumatoid arthritis, juvenile arthritis, and psoriatic arthritis;

Autoimmune or inflammatory diseases or disorders, including Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, autoimmune hepatitis, primary sclerosing cholangitis, chronic aggressive hepatitis, non-alcoholic fatty liver disease, non-alcoholic steatohepatitis ulcerative colitis and membranous glomerulopathy, systemic lupus erythematosus, rheumatoid arthritis, psoriatic arthritis, Sjogren's syndrome, Reiter's syndrome, polymyositis, dermatomyositis, type I interferonopathies including Aicardi-Goutières syndrome and other mendelian diseases of overexpression of type I interferon systemic sclerosis, polyarteritis nodosa, multiple sclerosis, relapsing remitting multiple sclerosis, primary progressive multiple sclerosis, secondary progressive multiple sclerosis, and bullous pemphigoid, and additional autoimmune diseases, which can be O-cell (humoral) based or T-cell based, including Cogan's syndrome, ankylosing spondylitis, Wegener's granulomatosis, autoimmune alopecia, Type I or juvenile onset diabetes, or thyroiditis;

Cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, or angiogenic-associated disorders including solid tumors;

Diabetes, including Type I diabetes or complications from diabetes;

Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, or ocular neovascularization;

Intestinal inflammations, including Crohn's disease, ulcerative colitis, inflammatory bowel disease, celiac diseases, proctitis, eosinophilic gastroenteritis, or mastocytosis;

Neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemia, renal ischemia, heart attacks, cardiac hypertrophy, atherosclerosis and arteriosclerosis, organ hypoxia, or platelet aggregation;

Skin diseases, conditions or disorders including atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummular dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, *Pityriasis alba*, pemphigus, vulvovaginitis, acne, chronic spontaneous urticaria, chronic idiopathic urticaria, chronic physical urticaria, Vogt-Koyanagi-Harada disease, Sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurtiva, psoriasis, plaque psoriasis, pustular psoriasis, nail psoriasis, flexural psoriasis, guttate psoriasis, psoriatic arthritis, erythrodermic psoriasis, or inverse psoriasis;

Allergic reactions including allergic dermatitis in mammal (including horse allergic diseases such as bite hypersensitivity), summer eczema, sweet itch in horses, heaves, inflammatory airway disease, recurrent airway obstruction, airway hyper-responsiveness, or chronic obstruction pulmonary disease;

Asthma and other obstructive airways diseases, including chronic or inveterate asthma, late asthma, bronchitis, bronchial asthma, allergic asthma, intrinsic asthma, extrinsic asthma, or dust asthma; and, Transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation.

The present invention will be further understood from the following description given by way of example only. The present invention is directed to a class of benzonitrile derivatives. In particular, the present invention is directed to benzonitrile compounds useful as inhibitors of SIK. While the present invention is not so limited, an appreciation of various aspects of the invention will be gained through the following discussion and the examples.

The terms "isolated" and "in isolated form" means that a compound, or salt thereof, for a compound refers to the physical state of the compound after being isolated from a synthetic process, e.g., from a reaction mixture. Thus, the terms "isolated" and "in isolated form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan. As examples, the purification techniques disclosed herein (e.g., LC-MS and LC-MS/MS techniques) result in isolated forms of the subject compounds. Such isolation and purification techniques would be expected to result in product purities containing at least about 70%, at least about 80%, at least about 90%, at least about 95%, at least about 97%, or at least about 99% by weight of the compound, or salt thereof.

The term "subject" refers to a mammal, e.g., human, livestock or companion animals. A "patient", an "individual" or a "subject," used interchangeably, is a mammal, more preferably, a human.

The term "companion animal" or "companion animals" refers to animals kept as pets or household animals. Examples of companion animals include dogs, cats, and rodents including hamsters, guinea pigs, gerbils and the like, rabbits, ferrets and birds.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits, as well as birds, such as chickens, ducks and turkeys.

Unless otherwise defined herein, scientific and technical terms used in connection with the present invention have the meanings that are commonly understood by those of ordinary skill in the art.

If substituents are described as being "independently selected" from a group, each substituent is selected independent of the other. Each substituent therefore may be identical to or different from the other substituent(s).

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above.

The term "selective", when used herein to describe a functionally-defined receptor ligand or enzyme inhibitor means selective for the defined receptor or enzyme subtype as compared with other receptor or enzyme subtypes in the same family. For instance, a selective SIK inhibitor is a compound which inhibits the SIK enzyme subtype more potently than any other SIK enzyme subtype. Such selectivity is, in one embodiment, at least 2 fold (as measured using conventional binding assays), or, in another embodiment, at least 10 fold, or, in a further embodiment, at least 100 fold.

The term "therapeutically-effective" indicates the capability of an agent to prevent, or reduce the severity of, the disorder. The phrase "therapeutically-effective" is to be understood to be equivalent to the phrase "effective for the treatment, prevention, or amelioration", and both are intended to qualify the amount of an agent—which will achieve the goal of mitigating the severity of cancer, cardiovascular disease, or pain and inflammation and the frequency of incidence over treatment of each agent by itself.

"Pharmaceutically acceptable" means suitable for use in a subject.

As used throughout this specification and the appended claims, the following terms have the following meanings:

The term "$C_1$-$C_3$ linear or branched alkyl" as used herein, means a straight or branched hydrocarbon chain containing from 1 to 3 carbon atoms. Representative examples of $C_1$-$C_3$ linear or branched alkyl include methyl, ethyl, n-propyl, and isopropyl.

The term "$C_1$-$C_4$ linear or branched alkyl" as used herein, means a straight or branched hydrocarbon chain containing from 1 to 4 carbon atoms. Representative examples of $C_1$-$C_4$ linear or branched alkyl include, but are not limited to, methyl, ethyl, n-propyl, n-butyl, iso-butyl, and isopropyl.

The term "halo($C_1$-$C_3$)linear or branched chain alkyl" as used herein, means at least one halogen, as defined herein, appended to the parent molecular moiety through a ($C_1$-$C_3$) linear or branched alkyl group, as defined herein. Representative examples of halo($C_1$-$C_3$)linear or branched alkyl include, but are not limited to, fluoromethyl, difluoromethyl, trifluoromethyl, 2,2,2-trifluoroethyl, and 2,2-difluoropropyl.

The term "halo($C_1$-$C_4$)linear or branched chain alkyl" as used herein, means at least one halogen, as defined herein, appended to the parent molecular moiety through a ($C_1$-$C_4$) linear or branched alkyl group, as defined herein. Representative examples of halo($C_1$-$C_4$)linear or branched alkyl include, but are not limited to, fluoromethyl, chloromethyl, difluoromethyl, trifluoromethyl, 2,2,2-trifluoroethyl, and pentafluoroethyl.

The term "cyano($C_1$-$C_4$)linear or branched chain alkyl" as used herein, means at least one cyano or nitrile group, as defined herein, appended to the parent molecular moiety through a ($C_1$-$C_4$)linear or branched alkyl group, as defined herein. Representative examples of cyano($C_1$-$C_4$)linear or branched alkyl include, but are not limited to, cyanomethyl, 2-cyanoethyl, 3-cyanopropyl, and 4-cyanobutyl.

The term "hydroxyl($C_1$-$C_4$)linear or branched chain alkyl" as used herein, means at least one hydroxyl group, as defined herein, is appended to the parent molecular moiety through a ($C_1$-$C_4$)linear or branched alkyl group, as defined herein. Representative examples of hydroxyl($C_1$-$C_4$)linear or branched alkyl include, but are not limited to, hydroxymethyl, 2-hydroxyethyl, 3-hydroxypropyl, 2,3-dihydroxypropyl, and 3,4-dihydroxybutyl.

The term "$C_1$-$C_3$ alkoxy($C_1$-$C_4$)linear or branched chain alkyl" as used herein, means at least one $C_1$-$C_3$ alkoxy group, as defined herein, is appended to the parent molecular moiety through a ($C_1$-$C_4$)linear or branched alkyl group, as defined herein. Representative examples of $C_1$-$C_3$ alkoxy ($C_1$-$C_4$)linear or branched alkyl include, but are not limited to, 2-methoxyethyl, 2-methoxypropyl, 3-methoxypropyl, 2-ethoxyethyl, and 3,4-dimethoxybutyl.

The term "halo($C_1$-$C_3$)alkoxy" as used herein, means at least one halogen, as defined herein, appended to the parent molecular moiety through a ($C_1$-$C_3$)alkoxy group, as defined herein. Representative examples of halo($C_1$-$C_3$)alkoxy include, but are not limited to, fluoromethoxy, difluoromethoxy, trifluoromethoxy, and 2-fluoroethoxy.

The term "($C_1$-$C_3$) alkoxy" as used herein, means a ($C_1$-$C_3$) alkoxy group, as defined herein, appended to the parent molecular moiety through an oxygen atom. Representative examples of ($C_1$-$C_3$) alkoxy include methoxy, ethoxy, propoxy, and 2-propoxy.

The term "$C_1$-$C_4$ linear or branched chain alkoxy" as used herein, means a $C_1$-$C_4$ linear or branched chain alkyl group, as defined herein, appended to the parent molecular moiety through an oxygen atom. Representative examples of $C_1$-$C_4$ linear or branched chain alkoxy include methoxy, ethoxy, propoxy, 2-propoxy, and butoxy.

The term "$C_1$-$C_3$ alkyl-substituted thiol" as used herein, means a $C_1$-$C_3$ alkyl group, as defined herein, appended to the parent molecular moiety through a sulfur atom. Representative examples of $C_1$-$C_3$ alkylthio include methylthio, ethylthio, propylthio, and 2-propylthio.

The term "($C_3$-$C_5$) cycloalkyl" as used herein, means a saturated cyclic hydrocarbon group containing from 3 to 5 carbons, examples of ($C_3$-$C_5$) cycloalkyl include cyclopropyl, cyclobutyl, and cyclopentyl.

The term "($C_3$-$C_6$) cycloalkyl" as used herein, means a saturated cyclic hydrocarbon group containing from 3 to 6 carbons, examples of ($C_3$-$C_6$) cycloalkyl include cyclopropyl, cyclobutyl, cyclopentyl, and cyclohexyl.

The term "($C_1$-$C_4$ linear or branched chain alkyl)amino" as used herein, means one ($C_1$-$C_4$ linear or branched chain alkyl) appended to the parent molecular moiety through a nitrogen atom. Representative examples of ($C_1$-$C_4$ linear or branched chain alkyl)amino include, but are not limited to, methylamino, ethylamino, propylamino, and 2-propylamino, and butylamino.

The term "di($C_1$-$C_4$ linear or branched chain alkyl)amino" as used herein, means two ($C_1$-$C_4$ linear or branched chain alkyl) appended to the parent molecular moiety through a nitrogen atom. Representative examples of di($C_1$-$C_4$ linear or branched chain alkyl)amino include, but are not limited to, dimethylamino, ethylmethylamino, diethylamino, methylpropylamino, and 2-propylmethylamino, and butylmethylamino.

The term "(4-6 membered)heterocyclic" or "heterocyclic" as used herein, means a 4, 5, or 6 membered ring containing at least one heteroatom independently selected from the group consisting of O, N, and S. The 4 membered ring contains 1 heteroatom selected from the group consisting of O, N and S; the 5 and 6 membered rings contain one or two heteroatoms selected from the group consisting of O, N and S. The heterocycle is connected to the parent molecular moiety through any carbon atom or any nitrogen atom contained within the heterocycle. Representative examples of heterocycle include, but are not limited to, azetidinyl, morpholinyl, piperazinyl, piperidinyl, pyranyl, pyrrolidinyl, tetrahydrofuranyl, tetrahydrothienyl, thiomorpholinyl, and thiopyranyl.

The term "$C_1$-$C_2$ alkyl" as used herein, means a methyl or ethyl group.

The term "amino" as used herein, means a —$NH_2$ group.

The term "cyano" or "nitrile" as used herein, means a —CN group.

The term "halo" or "halogen" as used herein, means —Cl, —Br, —I or —F.

The term "hydroxyl" or "hydroxy" as used herein, means —OH.

DETAILED DESCRIPTION OF THE INVENTION

The present invention relates to novel compounds which are SIK modulators useful for the treatment of diseases and conditions associated with dysregulation of SIK, in particular, SIK1, SIK2 and SIK3. The present invention further provides pharmaceutical compositions comprising such SIK enzyme modulators as well as methods of treating and/or preventing such diseases and conditions.

According to a first aspect of the invention there is provided a compound of formula I:

I

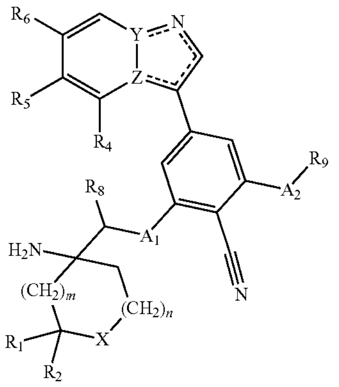

or a pharmaceutically acceptable salt thereof, wherein $A_1$ and $A_2$ are independently O or S;

X is selected from $CH_2$, $CD_2$, $NR_3$, O, and S, where $R_3$ is selected from hydrogen, $C_1$-$C_4$ linear or branched chain alkyl, halo($C_1$-$C_4$)linear or branched chain alkyl, and hydroxyl($C_1$-$C_4$)linear or branched chain alkyl;

Y and Z are selected from C and N, where when Y is C, then Z is N, and when Y is N, then Z is C;

$R_1$ and $R_2$ are independently selected from hydrogen, deuterium, $C_1$-$C_4$ linear or branched chain alkyl, halo ($C_1$-$C_4$)linear or branched chain alkyl, hydroxyl($C_1$-$C_4$)linear or branched chain alkyl, cyano($C_1$-$C_4$)linear or branched chain alkyl, and $C_1$-$C_3$ alkoxy($C_1$-$C_4$) linear or branched chain alkyl; or a $C_1$-$C_2$ alkyl substituted with a $C_3$-$C_5$ cycloalkyl ring; or taken together to form a $C_3$-$C_6$ cycloalkyl ring; or where X is $CH_2$ or $CD_2$, then $R_1$ and $R_2$ are independently selected from hydrogen, deuterium, halogen, hydroxyl, $C_1$-$C_4$ linear or branched chain alkyl, halo($C_1$-$C_4$)linear or branched chain alkyl, hydroxyl($C_1$-$C_4$)linear or branched chain alkyl, cyano($C_1$-$C_4$)linear or branched chain alkyl, and $C_1$-$C_3$ alkoxy($C_1$-$C_4$)linear or branched chain alkyl, and a $C_1$-$C_2$ alkyl substituted with a $C_3$-$C_5$ cycloalkyl ring;

$R_4$ is selected from hydrogen, deuterium, cyano, halogen, ($C_1$-$C_3$) alkoxy, halo($C_1$-$C_3$) alkoxy, $C_1$-$C_3$ alkyl-substituted thiol, $C_1$-$C_4$ linear or branched chain alkyl, halo($C_1$-$C_4$)linear or branched chain alkyl, and a hydroxyl($C_1$-$C_4$)linear or branched chain alkyl;

$R_5$ is selected from hydrogen, deuterium, halogen, $C_1$-$C_3$ alkoxy, amino, ($C_1$-$C_4$ linear or branched chain alkyl) amino, di($C_1$-$C_4$ linear or branched chain alkyl)amino, (4-6 membered)heterocyclic, $C_1$-$C_4$ linear or branched chain alkyl, halo($C_1$-$C_4$)linear or branched chain alkyl, and a hydroxyl($C_1$-$C_4$)linear or branched chain alkyl;

$R_6$ is selected from hydrogen, deuterium, halogen, $C_1$-$C_4$ linear or branched chain alkoxy, $CONH_2$, $C_1$-$C_4$ linear or branched chain alkyl, halo($C_1$-$C_4$)linear or branched chain alkyl, hydroxyl($C_1$-$C_4$)linear or branched chain alkyl, and $CO_2R_7$ where $R_7$ is selected from H and $C_1$-$C_4$ linear or branched chain alkyl;

$R_8$ is selected from hydrogen, deuterium, and $C_1$-$C_3$ linear or branched chain alkyl;

$R_9$ is selected from $C_1$-$C_3$ linear or branched chain alkyl, and a halo($C_1$-$C_3$)linear or branched chain alkyl; and, n and m are independently selected from 0, 1 and 2.

Described below are a number of embodiments (E) of this first aspect of the invention, where for convenience E1 is identical thereto.

E1. A compound of formula I as defined above, or a pharmaceutically acceptable salt thereof.

E2. The compound according to E1 or a pharmaceutically acceptable salt thereof, wherein $A_1$ is O.

E3. The compound according to E1 or a pharmaceutically acceptable salt thereof, wherein $A_2$ is O or S.

E4. The compound according to E1 or a pharmaceutically acceptable salt thereof, wherein $R_1$ and $R_2$ are independently selected from ethyl, methyl, and H.

E5. The compound according to E1 or a pharmaceutically acceptable salt thereof, wherein $R_4$ is cyano or methoxy.

E6. The compound according to E1 or a pharmaceutically acceptable salt thereof, wherein $R_5$ is H.

E7. The compound according to E1 or a pharmaceutically acceptable salt thereof, wherein $R_5$ is azetidine, pyrrolidine, or dimethylamino.

E8. The compound according to E1 or a pharmaceutically acceptable salt thereof, wherein $R_6$ is H.

E9. The compound according to E1 or a pharmaceutically acceptable salt thereof, wherein $R_8$ is H.

E10. The compound according to E1 or a pharmaceutically acceptable salt thereof, wherein $R_9$ is methyl.

E11. The compound according to E1 or a pharmaceutically acceptable salt thereof, wherein X is $CH_2$.

E12. The compound according to E1 or a pharmaceutically acceptable salt thereof, wherein X is O.

E13. The compound according to E1 or a pharmaceutically acceptable salt thereof, wherein m is 0 and n is 1.

E14. The compound according to E1 or a pharmaceutically acceptable salt thereof, wherein m is 1 and n is 1.

E15. A compound of formula IA having the structure:

IA

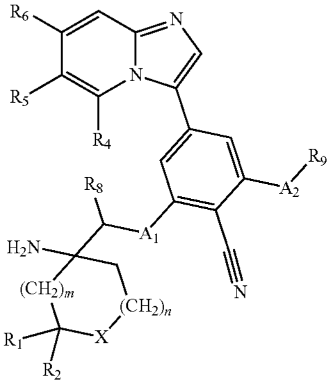

or a pharmaceutically acceptable salt thereof, wherein $A_1$ and $A_2$ are independently O or S;

X is selected from $CH_2$, $CD_2$, $NR_3$, O, and S, where $R_3$ is selected from hydrogen, $C_1$-$C_4$ linear or branched chain alkyl, halo($C_1$-$C_4$)linear or branched chain alkyl, and hydroxyl($C_1$-$C_4$)linear or branched chain alkyl;

$R_1$ and $R_2$ are independently selected from hydrogen, deuterium, $C_1$-$C_4$ linear or branched chain alkyl, halo($C_1$-$C_4$)linear or branched chain alkyl, hydroxyl($C_1$-$C_4$)linear or branched chain alkyl, cyano($C_1$-$C_4$)linear or branched chain alkyl, and $C_1$-$C_3$ alkoxy($C_1$-$C_4$) linear or branched chain alkyl; or a $C_1$-$C_2$ alkyl substituted with a $C_3$-$C_5$ cycloalkyl ring; or taken together to form a $C_3$-$C_6$ cycloalkyl ring; or where X is $CH_2$ or $CD_2$, then $R_1$ and $R_2$ are independently selected from hydrogen, deuterium, halogen, hydroxyl, $C_1$-$C_4$ linear or branched chain alkyl, halo($C_1$-$C_4$)linear or branched chain alkyl, hydroxyl($C_1$-$C_4$)linear or branched chain alkyl, cyano($C_1$-$C_4$)linear or branched chain alkyl, and $C_1$-$C_3$ alkoxy($C_1$-$C_4$)linear or branched chain alkyl, and a $C_1$-$C_2$ alkyl substituted with a $C_3$-$C_5$ cycloalkyl ring;

$R_4$ is selected from hydrogen, deuterium, cyano, halogen, ($C_1$-$C_3$) alkoxy, halo($C_1$-$C_3$) alkoxy, $C_1$-$C_3$ alkyl-substituted thiol, $C_1$-$C_4$ linear or branched chain alkyl, halo($C_1$-$C_4$)linear or branched chain alkyl, and a hydroxyl($C_1$-$C_4$)linear or branched chain alkyl;

$R_5$ is selected from hydrogen, deuterium, halogen, $C_1$-$C_3$ alkoxy, amino, ($C_1$-$C_4$ linear or branched chain alkyl) amino, di($C_1$-$C_4$ linear or branched chain alkyl)amino, (4-6 membered)heterocyclic, $C_1$-$C_4$ linear or branched chain alkyl, halo($C_1$-$C_4$)linear or branched chain alkyl, and a hydroxyl($C_1$-$C_4$)linear or branched chain alkyl;

$R_6$ is selected from hydrogen, deuterium, halogen, $C_1$-$C_4$ linear or branched chain alkoxy, $CONH_2$, $C_1$-$C_4$ linear or branched chain alkyl, halo($C_1$-$C_4$)linear or branched chain alkyl, hydroxyl($C_1$-$C_4$)linear or branched chain alkyl, and $CO_2R_7$ where $R_7$ is selected from H and $C_1$-$C_4$ linear or branched chain alkyl;

$R_8$ is selected from hydrogen, deuterium, and $C_1$-$C_3$ linear or branched chain alkyl;

$R_9$ is selected from $C_1$-$C_3$ linear or branched chain alkyl, and a halo($C_1$-$C_3$)linear or branched chain alkyl; and, n and m are independently selected from 0, 1 and 2.

E16. The compound according to E15 or a pharmaceutically acceptable salt thereof, wherein $A_1$ is O.

E17. The compound according to E15 or a pharmaceutically acceptable salt thereof, wherein $A_2$ is O or S.

E18. The compound according to E15 or a pharmaceutically acceptable salt thereof, wherein $R_1$ and $R_2$ are independently selected from ethyl, methyl, and H.

E19. The compound according to E15 or a pharmaceutically acceptable salt thereof, wherein $R_4$ is cyano or methoxy.

E20. The compound according to E15 or a pharmaceutically acceptable salt thereof, wherein $R_5$ is H.

E21. The compound according to E15 or a pharmaceutically acceptable salt thereof, wherein $R_5$ is azetidine, pyrrolidine, or dimethylamino.

E22. The compound according to E15 or a pharmaceutically acceptable salt thereof, wherein $R_6$ is H.

E23. The compound according to E15 or a pharmaceutically acceptable salt thereof, wherein $R_8$ is H.

E24. The compound according to E15 or a pharmaceutically acceptable salt thereof, wherein $R_9$ is methyl.

E25. The compound according to E15 or a pharmaceutically acceptable salt thereof, wherein X is $CH_2$.

E26. The compound according to E15 or a pharmaceutically acceptable salt thereof, wherein X is O.

E27. The compound according to E15 or a pharmaceutically acceptable salt thereof, wherein m is 0 and n is 1.

E28. The compound according to E15 or a pharmaceutically acceptable salt thereof, wherein m is 1 and n is 1.

E29. A compound of formula IB having the structure:

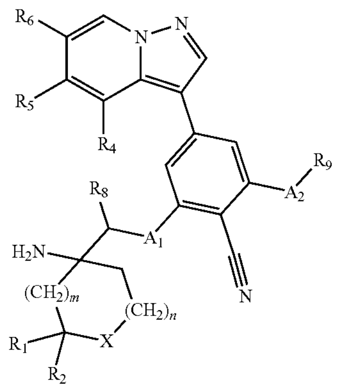

IB or a pharmaceutically acceptable salt thereof, wherein $A_1$ and $A_2$ are independently O or S;

X is selected from $CH_2$, $CD_2$, $NR_3$, O, and S, where $R_3$ is selected from hydrogen, $C_1$-$C_4$ linear or branched chain alkyl, halo($C_1$-$C_4$)linear or branched chain alkyl, and hydroxyl($C_1$-$C_4$)linear or branched chain alkyl;

$R_1$ and $R_2$ are independently selected from hydrogen, deuterium, $C_1$-$C_4$ linear or branched chain alkyl, halo ($C_1$-$C_4$)linear or branched chain alkyl, hydroxyl($C_1$-$C_4$)linear or branched chain alkyl, cyano($C_1$-$C_4$)linear or branched chain alkyl, and $C_1$-$C_3$ alkoxy($C_1$-$C_4$) linear or branched chain alkyl; or a $C_1$-$C_2$ alkyl substituted with a $C_3$-$C_5$ cycloalkyl ring; or taken together to form a $C_3$-$C_6$ cycloalkyl ring; or where X is $CH_2$ or $CD_2$, then $R_1$ and $R_2$ are independently selected from hydrogen, deuterium, halogen, hydroxyl, $C_1$-$C_4$ linear or branched chain alkyl, halo($C_1$-$C_4$)linear or branched chain alkyl, hydroxyl($C_1$-$C_4$)linear or branched chain alkyl, cyano($C_1$-$C_4$)linear or branched chain alkyl, and $C_1$-$C_3$ alkoxy($C_1$-$C_4$)linear or branched chain alkyl, and a $C_1$-$C_2$ alkyl substituted with a $C_3$-$C_5$ cycloalkyl ring;

$R_4$ is selected from hydrogen, deuterium, cyano, halogen, ($C_1$-$C_3$) alkoxy, halo($C_1$-$C_3$) alkoxy, $C_1$-$C_3$ alkyl-substituted thiol, $C_1$-$C_4$ linear or branched chain alkyl, halo($C_1$-$C_4$)linear or branched chain alkyl, and a hydroxyl($C_1$-$C_4$)linear or branched chain alkyl;

$R_5$ is selected from hydrogen, deuterium, halogen, $C_1$-$C_3$ alkoxy, amino, ($C_1$-$C_4$ linear or branched chain alkyl) amino, di($C_1$-$C_4$ linear or branched chain alkyl)amino, (4-6 membered)heterocyclic, $C_1$-$C_4$ linear or branched chain alkyl, halo($C_1$-$C_4$)linear or branched chain alkyl, and a hydroxyl($C_1$-$C_4$)linear or branched chain alkyl;

$R_6$ is selected from hydrogen, deuterium, halogen, $C_1$-$C_4$ linear or branched chain alkoxy, $CONH_2$, $C_1$-$C_4$ linear or branched chain alkyl, halo($C_1$-$C_4$)linear or branched chain alkyl, hydroxyl($C_1$-$C_4$)linear or branched chain alkyl, and $CO_2R_7$ where $R_7$ is selected from H and $C_1$-$C_4$ linear or branched chain alkyl;

$R_8$ is selected from hydrogen, deuterium, and $C_1$-$C_3$ linear or branched chain alkyl;

$R_9$ is selected from $C_1$-$C_3$ linear or branched chain alkyl, and a halo($C_1$-$C_3$)linear or branched chain alkyl; and, n and m are independently selected from 0, 1 and 2.

E30. The compound according to E29 or a pharmaceutically acceptable salt thereof, wherein $A_1$ is O.

E31. The compound according to E29 or a pharmaceutically acceptable salt thereof, wherein $A_2$ is O or S.

E32. The compound according to E29 or a pharmaceutically acceptable salt thereof, wherein $R_1$ and $R_2$ are independently selected from ethyl, methyl, and H.

E33. The compound according to E29 or a pharmaceutically acceptable salt thereof, wherein $R_4$ is cyano or methoxy.

E34. The compound according to E29 or a pharmaceutically acceptable salt thereof, wherein $R_5$ is H.

E35. The compound according to E29 or a pharmaceutically acceptable salt thereof, wherein $R_6$ is H.

E36. The compound according to E29 or a pharmaceutically acceptable salt thereof, wherein $R_8$ is H.

E37. The compound according to E29 or a pharmaceutically acceptable salt thereof, wherein $R_9$ is methyl.

E38. The compound according to E29 or a pharmaceutically acceptable salt thereof, wherein X is $CH_2$.

E39. The compound according to E29 or a pharmaceutically acceptable salt thereof, wherein m is 0 and n is 1.

E40. The compound according to E29 or a pharmaceutically acceptable salt thereof, wherein m is 1 and n is 1.

E41. The compound according to E1 selected from the group consisting of:

2-((1-Aminocyclopentyl)methoxy)-4-(5-methoxyimidazo[1,2-a]pyridin-3-yl)-6-(methylthio)benzonitrile;

2-(((1S,2R)-1-Amino-2-ethylcyclopentyl)methoxy)-6-methoxy-4-(5-methoxyimidazo[1,2-a]pyridin-3-yl)benzonitrile;

2-(((1R,2S)-1-Amino-2-ethylcyclopentyl)methoxy)-6-methoxy-4-(5-methoxyimidazo[1,2-a]pyridin-3-yl)benzonitrile;

2-((1-Amino-3-ethylcyclopentyl)methoxy)-6-methoxy-4-(5-methoxyimidazo[1,2-a]pyridin-3-yl)benzonitrile;

2-(((1R,3R)-1-Amino-3-ethylcyclopentyl)methoxy)-6-methoxy-4-(5-methoxyimidazo[1,2-a]pyridin-3-yl)benzonitrile;

2-(((1S,3S)-1-Amino-3-ethylcyclopentyl)methoxy)-6-methoxy-4-(5-methoxyimidazo[1,2-a]pyridin-3-yl)benzonitrile;

2-(((1R,3S)-1-Amino-3-ethylcyclopentyl)methoxy)-6-methoxy-4-(5-methoxyimidazo[1,2-a]pyridin-3-yl)benzonitrile;

2-(((1S,3R)-1-Amino-3-ethylcyclopentyl)methoxy)-6-methoxy-4-(5-methoxyimidazo[1,2-a]pyridin-3-yl)benzonitrile;

2-(((1S,2S)-1-Amino-2-ethylcyclopentyl)methoxy)-6-methoxy-4-(5-methoxyimidazo[1,2-a]pyridin-3-yl)benzonitrile;

2-(((1R,2R)-1-Amino-2-ethylcyclopentyl)methoxy)-6-methoxy-4-(5-methoxyimidazo[1,2-a]pyridin-3-yl)benzonitrile;

3-(3-(((1S,2R)-1-Amino-2-ethylcyclopentyl)methoxy)-4-cyano-5-(methylthio)phenyl)imidazo[1,2-a]pyridine-5-carbonitrile;

3-(3-(((1R,2S)-1-Amino-2-ethylcyclopentyl)methoxy)-4-cyano-5-(methylthio)phenyl)imidazo[1,2-a]pyridine-5-carbonitrile;

2-((1-Amino-2-ethylcyclopentyl)methoxy)-4-(5-methoxy-imidazo[1,2-a]pyridin-3-yl)-6-(methylthio)benzonitrile;

2-(((1S,2R)-1-Amino-2-ethylcyclopentyl)methoxy)-4-(5-methoxyimidazo[1,2-a]pyridin-3-yl)-6-(methylthio)benzonitrile;

2-(((1R,2S)-1-amino-2-ethylcyclopentyl)methoxy)-4-(5-methoxyimidazo[1,2-a]pyridin-3-yl)-6-(methylthio)benzonitrile;

2-(((2S,3R)-3-Amino-2-ethyltetrahydrofuran-3-yl)methoxy)-4-(5-methoxyimidazo[1,2-a]pyridin-3-yl)-6-(methylthio)benzonitrile;

2-(((2R,3R)-3-Amino-2-ethyltetrahydrofuran-3-yl)methoxy)-4-(5-methoxyimidazo[1,2-a]pyridin-3-yl)-6-(methylthio)benzonitrile;

2-(((2R,3S)-3-Amino-2-ethyltetrahydrofuran-3-yl)methoxy)-4-(5-methoxyimidazo[1,2-a]pyridin-3-yl)-6-(methylthio)-benzonitrile;

2-(((2S,3S)-3-Amino-2-ethyltetrahydrofuran-3-yl)methoxy)-4-(5-methoxyimidazo[1,2-a]pyridin-3-yl)-6-(methylthio)benzonitrile;

(R)-3-(3-((1-Amino-3,3-difluorocyclopentyl)methoxy)-4-cyano-5-(methylthio)phenyl)imidazo[1,2-a]pyridine-5-carbonitrile;

(S)-3-(3-((1-amino-3,3-difluorocyclopentyl)methoxy)-4-cyano-5-(methylthio)phenyl)imidazo[1,2-a]pyridine-5-carbonitrile;

(R)-2-((1-Amino-3,3-difluorocyclopentyl)methoxy)-4-(5-methoxyimidazo[1,2-a]pyridin-3-yl)-6-(methylthio)benzonitrile;

(S)-2-((1-Amino-3,3-difluorocyclopentyl)methoxy)-4-(5-methoxyimidazo[1,2-a]pyridin-3-yl)-6-(methylthio)benzonitrile;

(R)-3-(3-((1-Amino-3,3-dimethylcyclohexyl)methoxy)-4-cyano-5-(methylthio)phenyl)imidazo[1,2-a]pyridine-5-carbonitrile;

(S)-3-(3-((1-amino-3,3-dimethylcyclohexyl)methoxy)-4-cyano-5-(methylthio)phenyl)imidazo[1,2-a]pyridine-5-carbonitrile;

2-(((1R,3R)-1-Amino-3-ethylcyclohexyl)methoxy)-6-methoxy-4-(5-methoxyimidazo[1,2-a]pyridin-3-yl)benzonitrile;

2-(((1S,3S)-1-Amino-3-ethylcyclohexyl)methoxy)-6-methoxy-4-(5-methoxyimidazo[1,2-a]pyridin-3-yl)benzonitrile;

3-(3-(((1S,3S)-1-Amino-3-ethylcyclohexyl)methoxy)-4-cyano-5-(methylthio)phenyl)imidazo[1,2-a]pyridine-5-carbonitrile;

3-(3-(((1R,3R)-1-Amino-3-ethylcyclohexyl)methoxy)-4-cyano-5-(methylthio)phenyl)imidazo[1,2-a]pyridine-5-carbonitrile;

(S)-2-((1-Aminospiro[4.4]nonan-1-yl)methoxy)-6-methoxy-4-(5-methoxyimidazo[1,2-a]pyridin-3-yl)benzonitrile;

(R)-2-((1-Aminospiro[4.4]nonan-1-yl)methoxy)-6-methoxy-4-(5-methoxyimidazo[1,2-a]pyridin-3-yl)benzonitrile;

(S)-2-((3-Amino-1-(2,2,2-trifluoroethyl)piperidin-3-yl)methoxy)-6-methoxy-4-(5-methoxyimidazo[1,2-a]pyridin-3-yl)benzonitrile;

(R)-2-((3-Amino-1-(2,2,2-trifluoroethyl)piperidin-3-yl)methoxy)-6-methoxy-4-(5-methoxyimidazo[1,2-a]pyridin-3-yl)benzonitrile;

(R)-2-((3-Aminotetrahydrothiophen-3-yl)methoxy)-4-(imidazo[1,2-a]pyridin-3-yl)-6-(methylthio)benzonitrile;

(S)-2-((3-Aminotetrahydrothiophen-3-yl)methoxy)-4-(imidazo[1,2-a]pyridin-3-yl)-6-(methylthio)benzonitrile;

(R)-2-((3-Aminotetrahydrofuran-3-yl)methoxy)-4-(5-methoxyimidazo[1,2-a]pyridin-3-yl)-6-(methylthio)benzonitrile;

(S)-2-((3-Aminotetrahydrofuran-3-yl)methoxy)-4-(5-methoxyimidazo[1,2-a]pyridin-3-yl)-6-(methylthio)benzonitrile;

(R)-2-((1-Amino-3,3-difluorocyclopentyl)methoxy)-4-(imidazo[1,2-a]pyridin-3-yl)-6-(methylthio)benzonitrile;

(S)-2-((1-Amino-3,3-difluorocyclopentyl)methoxy)-4-(imidazo[1,2-a]pyridin-3-yl)-6-(methylthio)benzonitrile;

(R)-3-(3-((3-Aminotetrahydrothiophen-3-yl)methoxy)-4-cyano-5-(methylthio)phenyl)imidazo[1,2-a]pyridine-5-carbonitrile;

(S)-3-(3-((3-Aminotetrahydrothiophen-3-yl)methoxy)-4-cyano-5-(methylthio)phenyl)imidazo[1,2-a]pyridine-5-carbonitrile;

2-((1-Aminocyclohexyl)methoxy)-4-(5-methoxyimidazo[1,2-a]pyridin-3-yl)-6-(methylthio)benzonitrile;

(R)-2-((3-Aminotetrahydrothiophen-3-yl)methoxy)-4-(5-methoxyimidazo[1,2-a]pyridin-3-yl)-6-(methylthio)benzonitrile;

(S)-2-((3-Aminotetrahydrothiophen-3-yl)methoxy)-4-(5-methoxyimidazo[1,2-a]pyridin-3-yl)-6-(methylthio)benzonitrile;

2-(((1S)-1-Amino-3-(methoxymethyl)cyclohexyl)methoxy)-4-(imidazo[1,2-a]pyridin-3-yl)-6-(methylthio)benzonitrile;

2-(((1R)-1-Amino-3-(methoxymethyl)-cyclohexyl)methoxy)-4-(imidazo[1,2-a]pyridin-3-yl)-6-(methylthio)benzonitrile;

2-(((1S,2S)-1-Amino-2-(cyclopropylmethyl)cyclopentyl)methoxy)-6-methoxy-4-(5-methoxyimidazo[1,2-a]pyridin-3-yl)benzonitrile;

2-(((1R,2R)-1-Amino-2-(cyclopropylmethyl)cyclopentyl)methoxy)-6-methoxy-4-(5-methoxyimidazo[1,2-a]pyridin-3-yl)benzonitrile;

2-(((1S,2R)-1-Amino-2-(cyclopropylmethyl)cyclopentyl)methoxy)-6-methoxy-4-(5-methoxyimidazo[1,2-a]pyridin-3-yl)benzonitrile;

2-(((1R,2S)-1-Amino-2-(cyclopropylmethyl)cyclopentyl)methoxy)-6-methoxy-4-(5-methoxyimidazo[1,2-a]pyridin-3-yl)benzonitrile;

2-(((1S,3S)-1-Amino-3-(trifluoromethyl)cyclohexyl)methoxy)-4-(imidazo[1,2-a]pyridin-3-yl)-6-(methylthio)benzonitrile;

2-(((1R,3R)-1-Amino-3-(trifluoromethyl)cyclohexyl)methoxy)-4-(imidazo[1,2-a]pyridin-3-yl)-6-(methylthio)benzonitrile;

2-(((1R,3S)-1-Amino-3-(trifluoromethyl)cyclohexyl)methoxy)-4-(imidazo[1,2-a]pyridin-3-yl)-6-(methylthio)benzonitrile;

2-(((1S,3R)-1-Amino-3-(trifluoromethyl)cyclohexyl)methoxy)-4-(imidazo[1,2-a]pyridin-3-yl)-6-(methylthio)benzonitrile;

3-(3-((1-Aminocyclohexyl)methoxy)-4-cyano-5-(methylthio)phenyl)imidazo[1,2-a]pyridine-5-carbonitrile;

3-(3-((1-Aminocyclopentyl)methoxy)-4-cyano-5-(methylthio)phenyl)imidazo[1,2-a]pyridine-5-carbonitrile;

3-(3-((1-Aminocyclopentyl)methoxy)-4-cyano-5-(methylthio)phenyl)pyrazolo[1,5-a]pyridine-4-carbonitrile;

Ethyl 3-(3-((1-aminocyclopentyl)methoxy)-4-cyano-5-(methylthio)phenyl)-5-cyanoimidazo[1,2-a]pyridine-7-carboxylate;

3-(3-((1-Aminocyclopentyl)methoxy)-4-cyano-5-(methylthio)phenyl)-6-methoxyimidazo[1,2-a]pyridine-5-carbonitrile;

3-(3-((1-Aminocyclopentyl)methoxy)-4-cyano-5-(methylthio)phenyl)-7-methylimidazo[1,2-a]pyridine-5-carbonitrile;

3-(3-((1-Aminocyclopentyl)methoxy)-4-cyano-5-(methylthio)phenyl)-6-(dimethylamino)imidazo[1,2-a]pyridine-5-carbonitrile;

3-(3-((1-Aminocyclopentyl)methoxy)-4-cyano-5-(methylthio)phenyl)-6-ethylimidazo[1,2-a]pyridine-5-carbonitrile;

3-(3-((1-Aminocyclopentyl)methoxy)-4-cyano-5-(methylthio)phenyl)-6-methylimidazo[1,2-a]pyridine-5-carbonitrile;

3-(3-((1-Aminocyclopentyl)methoxy)-4-cyano-5-(methylthio)phenyl)-7-chloroimidazo[1,2-a]pyridine-5-carbonitrile;

3-(3-((1-Aminocyclohexyl)methoxy)-4-cyano-5-(methylthio)phenyl)pyrazolo[1,5-a]pyridine-4-carbonitrile;

6-Amino-3-(3-((1-aminocyclopentyl)methoxy)-4-cyano-5-(methylthio)phenyl)imidazo[1,2-a]pyridine-5-carbonitrile;

3-(3-((1-Aminocyclopentyl)methoxy)-4-cyano-5-(methylthio)phenyl)-6-(azetidin-1-yl)imidazo[1,2-a]pyridine-5-carbonitrile;

3-(3-((1-Aminocyclopentyl)methoxy)-4-cyano-5-(methylthio)phenyl)-6-(pyrrolidin-1-yl)imidazo[1,2-a]pyridine-5-carbonitrile;

3-(3-((1-Aminocyclopentyl)methoxy)-4-cyano-5-methoxyphenyl)-6-(dimethylamino)imidazo[1,2-a]pyridine-5-carbonitrile;

3-(3-((1-Aminocyclohexyl)methoxy)-4-cyano-5-(methylthio)phenyl)-6-methoxyimidazo[1,2-a]pyridine-5-carbonitrile;

3-(3-((1-Aminocyclopentyl)methoxy)-4-cyano-5-(methylthio)phenyl)-7-methoxyimidazo[1,2-a]pyridine-5-carbonitrile;

3-(3-((1-Aminocyclohexyl)methoxy)-4-cyano-5-(methylthio)phenyl)-7-methoxyimidazo[1,2-a]pyridine-5-carbonitrile;

3-(3-((1-Aminocyclohexyl)methoxy)-4-cyano-5-methoxyphenyl)-7-methoxyimidazo[1,2-a]pyridine-5-carbonitrile; and 3-(3-((1-Aminocyclopentyl)methoxy)-4-cyano-5-(methylthio)phenyl)-6-(methylamino)imidazo[1,2-a]pyridine-5-carbonitrile;

or, a pharmaceutically acceptable salt thereof.

E42. The compound according to E1 selected from the group consisting of:

3-(3-((1-Aminocyclohexyl)methoxy)-4-cyano-5-(methylthio)phenyl)imidazo[1,2-a]pyridine-5-carbonitrile;

2-(((1S,2R)-1-Amino-2-ethylcyclopentyl)methoxy)-6-methoxy-4-(5-methoxyimidazo[1,2-a]pyridin-3-yl)benzonitrile;

2-(((2S,3R)-3-Amino-2-ethyltetrahydrofuran-3-yl)methoxy)-4-(5-methoxyimidazo[1,2-a]pyridin-3-yl)-6-(methylthio)benzonitrile;

3-(3-(((1S,2R)-1-Amino-2-ethylcyclopentyl)methoxy)-4-cyano-5-(methylthio)phenyl)imidazo[1,2-a]pyridine-5-carbonitrile; and 3-(3-((1-Aminocyclopentyl)methoxy)-4-cyano-5-(methylthio)phenyl)-6-(dimethylamino)imidazo[1,2-a]pyridine-5-carbonitrile; or, a pharmaceutically acceptable salt thereof.

E43. 3-(3-((1-Aminocyclohexyl)methoxy)-4-cyano-5-(methylthio)phenyl)imidazo[1,2-a]pyridine-5-carbonitrile; or, a pharmaceutically acceptable salt thereof.

E44. 2-(((1S,2R)-1-Amino-2-ethylcyclopentyl)methoxy)-6-methoxy-4-(5-methoxyimidazo[1,2-a]pyridin-3-yl)benzonitrile; or, a pharmaceutically acceptable salt thereof.

E45. 2-(((2S,3R)-3-Amino-2-ethyltetrahydrofuran-3-yl)methoxy)-4-(5-methoxyimidazo[1,2-a]pyridin-3-yl)-6-(methylthio)benzonitrile; or, a pharmaceutically acceptable salt thereof.

E46. 3-(3-(((1S,2R)-1-Amino-2-ethylcyclopentyl)methoxy)-4-cyano-5-(methylthio)phenyl)imidazo[1,2-a]pyridine-5-carbonitrile; or, a pharmaceutically acceptable salt thereof.

E47. 3-(3-((1-Aminocyclopentyl)methoxy)-4-cyano-5-(methylthio)phenyl)-6-(dimethylamino)imidazo[1,2-a]pyridine-5-carbonitrile; or, a pharmaceutically acceptable salt thereof.

E48. A pharmaceutical composition comprising a compound according to any of E1 to E47, or a pharmaceutically acceptable salt thereof, or a pharmaceutically acceptable solvate of said compound or salt, and a pharmaceutically acceptable excipient.

E49. A method of treating a disease or condition selected from inflammation, autoimmune disease, neuroinflammation, arthritis, rheumatoid arthritis, spondyloarthropathies, systemic lupus erythematous, lupus nephritis, osteoarthritis, gouty arthritis, pain, fever, pulmonary sarcoidosis, silicosis, cardiovascular disease, atherosclerosis, myocardial infarction, thrombosis, congestive heart failure and cardiac reperfusion injury, cardiomyopathy, stroke, ischemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, diabetes (type 1 and type 2), diabetic neuropathy, viral and bacterial infection, myalgia, endotoxic shock, toxic shock syndrome, osteoporosis, multiple sclerosis, endometriosis, menstrual cramps, vaginitis, candidiasis, cancer, gastrointestinal cancer, fibrosis, obesity, muscular dystrophy, polymyositis, dermatomyositis, autoimmune hepatitis, primary biliary cirrhosis, primary sclerosing cholangitis, vitiligo, Alzheimer's disease, skin flushing, eczema, psoriasis, atopic dermatitis, sunburn, keloid, hypertrophic scar, rheumatic diseases, urticaria, discoid lupus, cutaneous lupus, central nervous system lupus, psoriatic arthritis, asthma, allergic asthma, type I interferonopathies including Aicardi-Goutières syndrome and other mendelian diseases of overexpression of type I interferon, primary progressive multiple sclerosis, relapsing remitting multiple sclerosis, non-alcoholic fatty liver disease, non-alcoholic steatohepatitis, scleroderma, alopecia areata, scarring alopecia, prurigo, prurigo nodularis, CPUO, lichen diseases, lichen planus, Steven's Johnson's syndrome, spondylopathy, myositis, vasculitis, pemphigus, lupus, major depression disorder, allergy, dry eye syndrome, transplant rejection, cancer, septic shock, cardiopulmonary dysfunction, acute respiratory disease, ankylosing spondylitis, cachexia, chronic graft-versus-host disease, acute graft-versus-host disease, Celiac Sprue, idiopathic thrombocytopenic thrombotic purpura, thrombotic thrombocytopenic purpura, myasthenia gravis, Sjogren's syndrome, epidermal hyperplasia, cartilage inflammation, bone degradation, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, reactive arthritis, Reter's Syndrome, myolitis, polymyolitis, dermatomyolitis, polyarteritis nodosa, Wegener's granulomatosis, arteritis, polymyalgia rheumatica, sarcoidosis, sclerosis, primary biliary sclerosis, sclerosing cholangitis, dermatitis, Still's disease, chronic obstructive pulmonary disease, Guillain-Barre disease, Graves' disease, Addison's disease, Raynaud's phenomenon, psoriatic epidermal hyperplasia, plaque psoriasis, guttate psoriasis, inverse psoriasis, pustular psoriasis, erythrodermic psoriasis, an immune disorder associated with or arising from activity of pathogenic lymphocytes, noninfectious uveitis, Behcet's disease and Vogt-Koyanagi-Harada syndrome, comprising administering to a subject in need thereof a compound according to any of E1 to E47, or a pharmaceutically acceptable salt thereof, or a pharmaceutically acceptable solvate of said compound or salt.

E50. A method of treating inflammatory bowel disease, Crohn's disease, ulcerative colitis, or gastrointestinal cancer, comprising administering to the subject a compound of any of E1 to E47 or a pharmaceutically acceptable salt thereof, or a pharmaceutically acceptable solvate of said compound or salt.

E51. The method according to E49, wherein the compound is selected from the group consisting of:

3-(3-((1-Aminocyclohexyl)methoxy)-4-cyano-5-(methylthio)phenyl)imidazo[1,2-a]pyridine-5-carbonitrile;

2-(((1S,2R)-1-Amino-2-ethylcyclopentyl)methoxy)-6-methoxy-4-(5-methoxyimidazo[1,2-a]pyridin-3-yl)benzonitrile;

2-(((2S,3R)-3-Amino-2-ethyltetrahydrofuran-3-yl)methoxy)-4-(5-methoxyimidazo[1,2-a]pyridin-3-yl)-6-(methylthio)benzonitrile;

3-(3-(((1S,2R)-1-Amino-2-ethylcyclopentyl)methoxy)-4-cyano-5-(methylthio)phenyl)imidazo[1,2-a]pyridine-5-carbonitrile; and, 3-(3-((1-Aminocyclopentyl)methoxy)-4-cyano-5-(methylthio)phenyl)-6-(dimethylamino)imidazo[1,2-a]pyridine-5-carbonitrile;

or, a pharmaceutically acceptable salt thereof.

E52. Use of a compound according to any of E1 to E47 for the manufacture of a medicament for the treatment of a disorder for which an SIK inhibitor is indicated.

E53. Use of a compound according to any of E1 to E47 for the manufacture of a medicament for the treatment of inflammatory bowel disease, Crohn's disease, ulcerative colitis, or gastrointestinal cancer.

E54. A compound according to any of E1 to E47 for use in the treatment of a disorder for which an SIK inhibitor is indicated.

Compounds of the invention that have the same molecular formula but differ in the nature or sequence of bonding of their atoms or the arrangement of their atoms in space are termed "isomers". Isomers that differ in the arrangement of their atoms in space are termed "stereoisomers". These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The enantiomers of the present invention indicated by (R), (S), or * are substantially free of the other enantiomer. "Substantially free" means that the enantiomeric excess is greater than about 90%, preferably greater than about 95%, and more preferably greater than about 99%. Within the context of enantiomeric excess, the term "about" means±1.0%. The symbol * designates a chiral carbon atom as either (R) or (S) stereochemistry depending on the configuration of substituents around the chiral carbon atom. The present invention contemplates various stereoisomers and mixtures thereof that are specifically included within the scope of this invention. Stereoisomers include enantiomers and mixtures of enantiomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution include, but are not limited to, (1) attachment of a chiral auxiliary to a mixture of enantiomers, separation of the resulting mixture of diastereomers by recrystallization or chromatography and liberation of the optically pure product from the auxiliary or (2) direct separation of the mixture of optical enantiomers on chiral chromatographic columns. Compounds of the present invention not designated (R), (S), or * may exist as racemates (i.e., 50% (R) and 50% (S)) or as a mixture of two enantiomers wherein one enantiomer is in excess. For example, enantiomeric mixtures may include the (R) enantiomer in 51% and the (S) enantiomer in 49% or vice versa or any combination of (R) and (S) other than the racemic mixture of 50% (R) and 50% (S).

Included within the scope of the described compounds are all isomers (e.g., cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds. Stereoisomeric mixtures, e.g., mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I, IA, or IB itself. Enantiomers may be separated through the formation of diastereomeric salts, for example by salt formation with an enantiomer-pure chiral acid, or by means of chromatography, for example by HPLC, using chromatographic substrates with chiral ligands. The present invention includes all pharmaceutically acceptable isotopically-labelled compounds of formula I, IA, or IB, or a pharmaceutically acceptable salt thereof, wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$,$^{17}O$ and $^{18}O$, phosphorus, such as $^{32}P$, and sulfur, such as $^{35}S$.

Certain isotopically-labelled compounds of formula I, IA, or IB, or a pharmaceutically acceptable salt thereof, for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula I, IA, or IB can generally be prepared by conventional techniques known to those skilled in the art or by processes analogous to those described in the accompanying Examples and Preparations using an appropriate isotopically-labeled reagent in place of the non-labeled reagent previously employed.

In some embodiments, the disclosure provides deuterium-labeled (or deuterated) compounds and salts, where the formula and variables of such compounds and salts are each and independently as described herein. "Deuterated" means that at least one of the atoms in the compound is deuterium in an abundance that is greater than the natural abundance of deuterium (typically approximately 0.015%). A skilled artisan recognized that in chemical compounds with a hydrogen atom, the hydrogen atom actually represents a mixture of H and D, with about 0.015% being D. The concentration of the deuterium incorporated into the deuterium-labeled compounds and salt of the invention may be defined by the deuterium enrichment factor.

"Deuterium enrichment factor" as used herein means the ratio between the deuterium abundance and the natural abundance of deuterium, each relative to hydrogen abundance. An atomic position designated as having deuterium typically has a deuterium enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

It is understood that one or more deuteriums may exchange with hydrogen under physiological conditions.

In some embodiments, the disclosure provides a deuterium compound of Formula I in place of the non-labeled reagent previously employed, or a pharmaceutically acceptable salt thereof.

In some embodiments, R1 is selected from $CH_3$, $CH_2D$, $CHD_2$ and $CD_3$.

In some embodiments, the deuterium compound of Formula I is selected from any one of the compounds set forth in the Examples section.

In some embodiments, metabolically labile sites in the compounds of the invention are deuterated.

Isotopically-labeled compounds of the invention may generally be prepared by conventional techniques known to those skilled in the art or by processes analogous to those described in the accompanying Examples and Preparations using an appropriate isotopically-labeled reagent in place of the non-labeled reagent previously employed. It is also well recognized in the art that some variation of natural isotopic abundance can occur in synthesized compounds, which can depend on the origin of the synthetic materials used in the syntheses of the compounds.

The deuterium enrichment of the compounds provided herein can be determined using conventional analytical methods known to one of ordinary skill in the art, including mass spectrometry, nuclear magnetic resonance spectroscopy, and crystallography.

Pharmaceutically acceptable solvates in accordance with the invention include those wherein the solvent of crystallization may be isotopically substituted, e.g., $D_2O$, $d_6$-acetone, $d_6$-DMSO.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutically acceptable salts of the compound of formula I, IA, or IB include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts. For a review on suitable salts, see *Handbook of Pharmaceutical Salts: Properties, Selection, and Use* by Stahl and Wermuth (Wiley-VCH, 2002).

Pharmaceutically acceptable salts of a compound of formula I, IA, or IB may be prepared, respectively, by one or more of three methods: (i) by reacting the compound of formula I, IA, or IB with the desired acid; (ii) by removing an acid- or base-labile protecting group from a suitable precursor of a compound of formula I, IA, or IB, or by ring-opening a suitable cyclic precursor, for example, a lactone or lactam, using the desired acid or base; or (iii) by converting one salt of a compound of formula I, IA, or IB to another by reaction with an appropriate acid or base or by means of a suitable ion exchange column. All three reactions are typically carried out in solution. The resulting salt may precipitate out and be collected by filtration or may be recovered by evaporation of the solvent. The degree of ionization in the resulting salt may vary from completely ionized to almost non-ionized.

The invention also includes the following embodiments:

a compound of I, IA, or IB, or a pharmaceutically acceptable salt thereof, as defined in any of the embodiments described herein, for use as a medicament;

a compound of I, IA, or IB, or a pharmaceutically acceptable salt thereof, as defined in any of the embodiments described herein, for use in the treatment of selected from inflammation, autoimmune disease, neuroinflammation, arthritis, rheumatoid arthritis, spondyloarthropathies, systemic lupus erythematous, lupus nephritis, osteoarthritis, gouty arthritis, pain, fever, pulmonary sarcoidosis, silicosis, cardiovascular disease, atherosclerosis, myocardial infarction, thrombosis, congestive heart failure and cardiac reperfusion injury, cardiomyopathy, stroke, ischemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, diabetes (type 1 and type 2), diabetic neuropathy, viral and bacterial infection, myalgia, endotoxic shock, toxic shock syndrome, osteoporosis, multiple sclerosis, endometriosis, menstrual cramps, vaginitis, candidiasis, cancer, fibrosis, obesity, muscular dystrophy, polymyositis, dermatomyositis, autoimmune hepatitis, primary biliary cirrhosis, primary sclerosing cholangitis, vitiligo, Alzheimer's disease, skin flushing, eczema, psoriasis, atopic dermatitis, sunburn, keloid, hypertrophic scar, rheumatic diseases, urticaria, discoid lupus, cutaneous lupus, central nervous system lupus, psoriatic arthritis, asthma, allergic asthma, type I interferonopathies including Aicardi-Goutières syndrome and other mendelian diseases of overexpression of type I interferon, primary progressive multiple sclerosis, relapsing remitting multiple sclerosis, non-alcoholic fatty liver disease, non-alcoholic steatohepatitis, scleroderma, alopecia areata, spondylopathy, myositis, vasculitis, pemphigus, lupus, major depression disorder, allergy, dry eye syndrome, transplant rejection, cancer, septic shock, cardiopulmonary dysfunction, acute respiratory disease, ankylosing spondylitis, cachexia, chronic graft-versus-host disease, acute graft-versus-host disease, Celiac Sprue, idiopathic thrombocytopenic thrombotic purpura, myasthenia gravis, Sjogren's syndrome, epidermal hyperplasia, cartilage inflammation, bone degradation, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, reactive arthritis, Reter's Syndrome, myolitis, polymyolitis, dermatomyolitis, polyarteritis nodosa, Wegener's granulomatosis, arteritis, polymyalgia rheumatica, sarcoidosis, sclerosis, primary biliary sclerosis, sclerosing cholangitis, dermatitis, Still's disease, chronic obstructive pulmonary disease, Guillain-Barre disease, Graves' disease, Addison's disease, Raynaud's phenomenon, psoriatic epidermal hyperplasia, plaque psoriasis, guttate psoriasis, inverse psoriasis, pustular psoriasis, erythrodermic psoriasis, an immune disorder associated with or arising from activity of pathogenic lymphocytes, noninfectious uveitis, Behcet's disease or Vogt-Koyanagi-Harada syndrome;

a method of treating a disease for which an inhibitor of SIK is indicated, in a subject in need of such treatment, comprising administering to the subject a therapeutically effective amount of a compound of formula I, IA, or IB, or a pharmaceutically acceptable salt thereof, as defined in any of the embodiments described herein;

the use of a compound of formula I, IA, or IB, or a pharmaceutically acceptable salt thereof, as defined in any of the embodiments described herein, for the manufacture of a medicament for treating a disease or condition for which an inhibitor of SIK is indicated;

a compound of formula I, IA, or IB, or a pharmaceutically acceptable salt thereof, as defined in any of the embodiments described herein, for use in the treatment of a disease or condition for which an inhibitor of SIK is indicated;

a pharmaceutical composition for the treatment of a disease or condition for which an inhibitor of SIK is indicated, comprising a compound of formula I, IA, or IB, or a pharmaceutically acceptable salt thereof, as defined in any of the embodiments described herein.

The present invention also provides any of the uses, methods or compositions as defined above wherein the compound of formula I, IA, or IB, or a pharmaceutically acceptable salt thereof, is used in combination with another pharmacologically active compound, particularly one of the functionally-defined classes or specific compounds listed below. These agents may be administered as part of the same or separate dosage forms, via the same or different routes of administration, and on the same or different administration schedules according to standard pharmaceutical practice known to one skilled in the art.

Suitable agents for use in combination therapy with a compound of formula I, IA, or IB, or a pharmaceutically acceptable salt thereof, sulfasalazine, mesalazine, prednisone, azathioprine, infliximab, adalimumab, belimumab, becertolizumab, natalizumab, vedolizumab, hydrocortisone, budesonide, cyclosporin, tacrolimus, fexofenadine, 6-mercaptopurine, methotrexate, ursodeoxycholic acid, obeticholic acid, anti-histamines, rifampin, prednisone, methotrexate, azathioprine, cyclophosphamide, hydroxychloroquine, mofetil, sodium mycophenolate, tacrolimus, leflunomide, chloroquine and quinacrine, thalidomide, rituxan, NSAIDs, solumedrol, depomedrol and dexamethasone.

Other suitable agents for use in combination therapy with a compound of formula I, IA, or IB, or a pharmaceutically acceptable salt thereof, include: a 5-lipoxygenase activating protein (FLAP) antagonist; a leukotriene antagonist (LTRA) such as an antagonist of $LTB_4$, $LTC_4$, $LTD_4$, $LTE_4$, $CysLT_1$ or $CysLT_2$, e.g., montelukast or zafirlukast; a histamine receptor antagonist, such as a histamine type 1 receptor antagonist or a histamine type 2 receptor antagonist, e.g., loratidine, fexofenadine, desloratidine, levocetirizine, methapyrilene or cetirizine; an al-adrenoceptor agonist or an $\alpha$2-adrenoceptor agonist, e.g., phenylephrine, methoxamine, oxymetazoline or methylnorephrine; a muscarinic M3 receptor antagonist, e.g., tiotropium or ipratropium; a dual muscarinic M3 receptor antagonist/$\beta$2 agonist; a PDE inhibitor, such as a PDE3 inhibitor, a PDE4 inhibitor or a PDE5 inhibitor, e.g., theophylline, sildenafil, vardenafil, tadalafil, ibudilast, cilomilast or roflumilast; sodium cromoglycate or sodium nedocromil; a cyclooxygenase (COX) inhibitor, such as a non-selective inhibitor (e.g., aspirin or ibuprofen) or a selective inhibitor (e.g., celecoxib or valdecoxib); a glucocorticosteroid, e.g., fluticasone, mometasone, dexamethasone, prednisolone, budesonide, ciclesonide or beclamethasone; an anti-inflammatory monoclonal antibody, e.g., infliximab, adalimumab, tanezumab, ranibizumab, bevacizumab or mepolizumab; a β2 agonist, e.g., salmeterol, albuterol, salbutamol, fenoterol or formoterol, particularly a long-acting β2 agonist; an integrin antagonist, e.g., natalizumab; an adhesion molecule inhibitor, such as a VLA-4 antagonist; a kinin $B_1$ or $B_2$ receptor antagonist; an immunosuppressive agent, such as an inhibitor of the IgE pathway (e.g., omalizumab) or cyclosporine; a matrix metalloprotease (MMP) inhibitor, such as an inhibitor of MMP-9 or MMP-12; a tachykinin $NK_1$, $NK_2$ or $NK_3$ receptor antagonist; a protease inhibitor, such as an inhibitor of elastase, chymase or catheopsin G; an adenosine $A_{2a}$ receptor agonist; an adenosine $A_{2b}$ receptor antagonist; a urokinase inhibitor; a dopamine receptor agonist (e.g., ropinirole), particularly a dopamine D2 receptor agonist (e.g., bromocriptine); a modulator of the NFκB pathway, such as an IKK inhibitor; a further modulator of a cytokine signalling pathway such as an inhibitor of syk kinase, p38 kinase, SPHK-1 kinase, Rho kinase, EGF-R or MK-2; a mucolytic, mucokinetic or anti-tussive agent; an antibiotic; an antiviral agent; a vaccine; a chemokine; an epithelial sodium channel (ENaC) blocker or Epithelial sodium channel (ENaC) inhibitor; a nucleotide receptor agonist, such as a P2Y2 agonist; a thromboxane inhibitor; niacin; a 5-lipoxygenase (5-LO) inhibitor, e.g., Zileuton; an adhesion factor, such as VLAM, ICAM or ELAM; a CRTH2 receptor ($DP_2$) antagonist; a prostaglandin $D_2$ receptor ($DP_1$) antagonist; a haematopoietic prostaglandin D2 synthase (HPGDS) inhibitor; interferon-β; a soluble human TNF receptor, e.g., Etanercept; a HDAC inhibitor; a phosphoinositide 3-kinase gamma (PI3Kγ) inhibitor; a phosphoinositide 3-kinase delta (PI3Kδ) inhibitor; a CXCR-1 or a CXCR-2 receptor antagonist; an IRAK-4 inhibitor; and, a TLR-4 or TLR-9 inhibitor, including the pharmaceutically acceptable salts of the specifically named compounds. The agents may be administered with another active agent, wherein the second active agent may be administered either orally or topically.

Accordingly, the invention provides methods of treating or preventing a disease, condition or disorder associated with SIK in a subject, such as a human or non-human mammal, comprising administering an effective amount of one or more compounds described herein to the subject in need thereof. Conditions in which selective targeting of the SIK pathway or modulation of the SIK kinases are contemplated to be therapeutically useful include, inter alia, arthritis, asthma, autoimmune diseases, cancers or tumors, diabetes, certain eye diseases, disorders or conditions, inflammation, intestinal inflammations, allergies or conditions, neurodegenerative diseases, psoriasis, and transplant rejection.

One way of carrying out the invention is to administer a compound of formula I, IA, or IB in the form of a prodrug. Thus, certain derivatives of a compound of formula I, IA, or IB which may have little or no pharmacological activity themselves can, when administered into or onto the body, be converted into a compound of formula I, IA, or IB having the desired activity, for example by hydrolytic cleavage, particularly hydrolytic cleavage promoted by an esterase or peptidase enzyme. Such derivatives are referred to as "prodrugs." Further information on the use of prodrugs may be found in 'Pro-drugs as Novel Delivery Systems', Vol. 14, *ACS Symposium Series* (T. Higuchi and W. Stella) and 'Bioreversible Carriers in Drug Design', Pergamon Press, 1987 (Ed. E. B. Roche, American Pharmaceutical Association). Reference can also be made to *Nature Reviews/Drug Discovery,* 2008, 7, 355 and *Current Opinion in Drug Discovery and Development,* 2007, 10, 550.

Prodrugs in accordance with the invention can, for example, be produced by replacing appropriate functionalities present in the compounds of formula I, IA, or IB with certain moieties known to those skilled in the art as 'pro-moieties' as described, for example, in 'Design of Prodrugs' by H. Bundgaard (Elsevier, 1985).

Thus, a prodrug in accordance with the invention is (a) an ester or amide derivative of a hydroxy group in a compound of formula I, IA, or IB; (b) an ester, carbonate, carbamate, phosphate or ether derivative of a hydroxy group in a compound of formula I, IA, or IB; (c) an amide, imine, carbamate or amine derivative of an amino group in a compound form formula I, IA, or IB; (d) an oxime or imine derivative of a carbonyl group in a compound of formula I, IA, or IB.

Some specific examples of prodrugs in accordance with the invention include:

(i) where the compound of formula I, IA, or IB contains a hydroxyl functionality (ii) where the compound of formula I, IA, or IB contains an alcohol functionality (—OH), an ester thereof, such as a compound wherein the hydrogen of the alcohol functionality of the compound of formula I, IA, or IB is replaced by —CO($C_1$-$C_8$ alkyl) (e.g., methylcarbonyl) or the alcohol is esterified with an amino acid;

(iii) where the compound of formula I, IA, or IB contains an alcohol functionality (—OH), an ether thereof, such as a compound wherein the hydrogen of the alcohol functionality of the compound of formula I, IA, or IB is replaced by ($C_1$-$C_8$ alkyl)C(═O)OCH$_2$— or —CH$_2$OP(═O)(OH)$_2$;

(iv) where the compound of formula I, IA, or IB contains an alcohol functionality (—OH), a phosphate thereof, such as a compound wherein the hydrogen of the alcohol functionality of the compound of formula I, IA, or IB is replaced by —P(═O)(OH)$_2$ or —P(═O)(ONa)$_2$ or —P(═O)(O$^-$)$_2$Ca$^{2+}$;

(v) where the compound of formula I, IA, or IB contains a secondary amino functionality (—NHR where R≠H), an amide thereof, for example, a compound wherein, as the case may be, one or both hydrogens of the amino functionality of the compound of formula I, IA, or IB is/are replaced by ($C_1$-$C_{10}$)alkanoyl, —COCH$_2$NH$_2$ or the amino group is derivatised with an amino acid;

(vi) where the compound of formula I, IA, or IB contains a secondary amino functionality (—NH$_2$ or —NHR where R≠H), an amine thereof, for example, a compound wherein, as the case may be, one or both hydrogens of the amino functionality of the compound of formula I, IA, or IB is/are replaced by —CH$_2$OP(═O)(OH)$_2$.

References to compounds of formula I, IA, or IB are taken to include the compounds themselves and prodrugs thereof. The invention includes such compounds of formula I, IA, or IB as well as pharmaceutically acceptable salts of such compounds.

Also included within the scope of the invention are active metabolites of compounds of formula I, IA, or IB, that is, compounds formed in vivo upon administration of the drug, often by oxidation or dealkylation. Some examples of metabolites in accordance with the invention include (i) where the compound of formula I, IA, or IB contains a methylene group, an hydroxymethylene derivative thereof (—CH$_2$—>—CHOH):

(ii) where the compound of formula I, IA, or IB contains a tertiary amino group, a secondary amino derivative thereof (—NRR'—>—NHR or —NHR'); and, (iii) where the compound of formula I, IA, or IB contains a secondary amino group, a primary derivative thereof (—NHR→—$NH_2$).

In another embodiment, the present invention provides pharmaceutical compositions, or formulations, comprising a therapeutically effective amount of a compound of the present invention and a pharmaceutically acceptable diluent or carrier. The pharmaceutical compositions, or formulations, of this invention may be administered to humans and other mammals topically, orally, parenterally, intracisternally, intravaginally, intraperitoneally, buccally, as an oral spray, as a nasal spray, rectally as a suppository, or in the form of a liposome.

A typical pharmaceutical composition or formulation is prepared by mixing a compound of the present invention and a carrier or diluent. Suitable carriers and diluents include materials such as carbohydrates, waxes, water soluble and/or swellable polymers, hydrophilic or hydrophobic materials, gelatin, oils, solvents, water, and the like. The particular carrier or diluent used will depend upon the means and purpose for which the compound of the present invention is being applied. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., for use in the preparing a medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the carriers described above. The dissolution rate of poorly water-soluble compounds may be enhanced by the use of a spray-dried dispersion, such as those described by Takeuchi, H., et al., in "Enhancement of the dissolution rate of a poorly water-soluble drug (tolbutamide) by a spray-drying solvent deposition method and disintegrants," *J. Pharm. Pharmacol.,* 39, 769-773 (1987); and EP0901786 B1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical composition, or formulation, for application may be packaged in a variety of ways depending upon the method used for administering the drug. Generally, an article for distribution includes a container having deposited therein the pharmaceutical formulation in an appropriate form. Suitable containers include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The term "pharmaceutically acceptable carrier" refers to carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Additional information concerning carriers can be found in Remington: The Science and Practice of Pharmacy, 21st Ed., Lippincott, Williams & Wilkins (2005) which is incorporated herein by reference. Further examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; carriers such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "pharmaceutically acceptable topical carrier" refers to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Compounds that are volatile in may require admixture with special formulating agents or with special packaging materials to assure proper dosage delivery. In addition, compounds of the present invention that have poor human skin permeability may require one or more permeability enhancers whereas compounds rapidly absorbed through the skin may require formulation with absorption-retarding agents or barriers.

The ointments, pastes, creams, lotions, gels, powders, and solutions, for topical administration may contain, in addition to an active compound of the present invention, pharmaceutically acceptable carriers such as animal and vegetable fats, oils, waxes, paraffins, starch, tragacanth, cellulose derivatives, polyethylene glycols, silicones, bentonites, silicic acid, talc, zinc oxide, preservatives, antioxidants, fragrances, emulsifiers, dyes, inert fillers, anti-irritants, tackifiers, fragrances, opacifiers, antioxidants, gelling agents, stabilizers, surfactants, emollients, coloring agents, preservatives, buffering agents, permeation enhancers, or mixtures thereof. Topical carriers should not interfere with the effectiveness of the biological activity of the active agent and not be deleterious to the epithelial cells or their function.

The terms "permeability enhancer," or "permeation enhancer," relates to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal or human skin, nail, hair, claw or hoof using a diffusion cell apparatus. A diffusion cell is described by Merritt et al. Diffusion Apparatus for Skin Penetration, J of Controlled Release, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Solid dosage forms for oral administration include capsules, tablets, pills, powders, and granules. In such solid dosage forms, the active compound is mixed with at least one inert pharmaceutically acceptable carrier such as sodium citrate or calcium phosphate and/or a) fillers or extenders such as starches, lactose, sucrose, glucose, mannitol, and salicylic acid; b) binders such as carboxymethylcellulose, alginates, gelatin, polyvinyl pyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

The term "parenterally," as used herein, refers to modes of administration which include intravenous, intramuscular, intraperitoneal, intrasternal, subcutaneous, intraarticular injection and infusion. Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Pharmaceutical compositions, or formulations, for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Compounds of the present invention may also be administered in the form of liposomes. Liposomes are generally derived from phospholipids or other lipid substances and are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N. Y. (1976), p 33 et seq.

Pharmaceutical compositions, or formulations, of the present invention may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

The pharmaceutical compositions, or formulations, of the invention may be suspensions. Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The pharmaceutical compositions also include solvates and hydrates of the compounds of the present invention. The term "solvate" refers to a molecular complex of a compound represented by Formula I, IA, or IB, including pharmaceutically acceptable salts thereof, with one or more solvent molecules. Such solvent molecules are those commonly used in the pharmaceutical art, which are known to be innocuous to the recipient, e.g., water, ethanol, ethylene glycol, (S)-propylene glycol, (R)-propylene glycol, and the like. The term "hydrate" refers to the complex where the solvent molecule is water. The solvates and/or hydrates preferably exist in crystalline form. Other solvents may be used as intermediate solvates in the preparation of more desirable solvates. Intermediate solvents include, but are not limited to, methanol, methyl t-butyl ether, ethyl acetate, methyl acetate, 1,4-butyne-diol, and the like.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.000001 to about 10 mg/kg/day. For purposes of oral administration, more preferable doses can be in the range of from about 0.001 to about 1 mg/kg/day. For topical administration, more preferable doses can be in the range of 0.00001 mg/kg/day to about 5 mg/kg/day. If desired, the effective daily dose can be divided into multiple doses for purposes of administration, e.g., two to four separate doses per day.

Synthetic Methods

The following schemes and written descriptions provide general details regarding the preparation of the compounds of the invention. The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula I, IA, or IB.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in Greene's *Protective Groups in Organic Synthesis* by Theodora W Greene and Peter G M Wuts, 3rd edition, (John Wiley and Sons, 1999), in particular, chapters 7 ("Protection for the Amino Group") and 5 ("Protection for the Carboxyl Group"), incorporated herein by reference, which also describes methods for the removal of such groups.

All of the derivatives of formula I can be prepared by the procedures described in the general methods presented below or by routine modifications thereof. The present invention also encompasses any one or more of these processes for preparing the derivatives of formula I, IA, or IB, in addition to any novel intermediates used therein. The person skilled in the art will appreciate that the following reactions may be heated thermally or under microwave irradiation. It will be further appreciated that it may be necessary or desirable to carry out the transformations in a different order from that described in the schemes, or to modify one or more of the transformations, to provide the desired compound of the invention.

One skilled in the art will also recognize that some compounds of the invention are chiral and thus may be prepared as racemic or scalemic mixtures of enantiomers. Several methods are available and are well known to those skilled in the art for the separation of enantiomers. A preferred method for the routine separation of enantiomers is supercritical fluid chromatography employing a chiral stationary phase.

Reaction Scheme IA and Reaction Scheme IB outline the general procedures for the synthesis of intermediates that can be used to provide compounds of the present invention having Formula (I). R' and R" represent chemical groups that are described within the scope of the Claims; Boc=tert-butoxycarbonyl; PG=protecting group. Those skilled in the art will recognize that Reaction Scheme IA and Reaction Scheme IB may depict the synthesis of racemic compounds, and that these routes may be adapted to the synthesis of either enantiomer of compounds of Formula (I).

Reaction Scheme IA

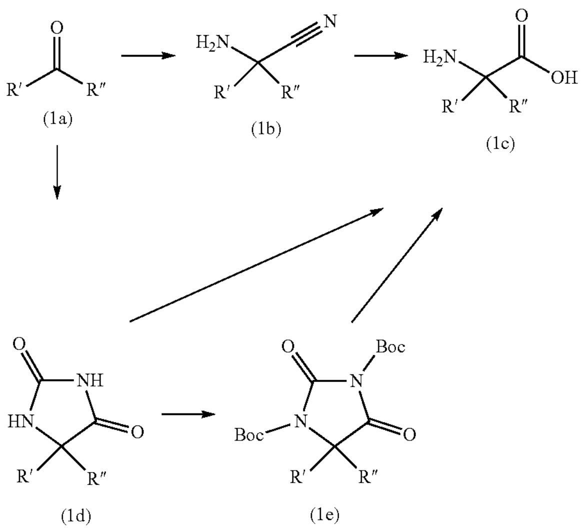

Reaction Scheme IB

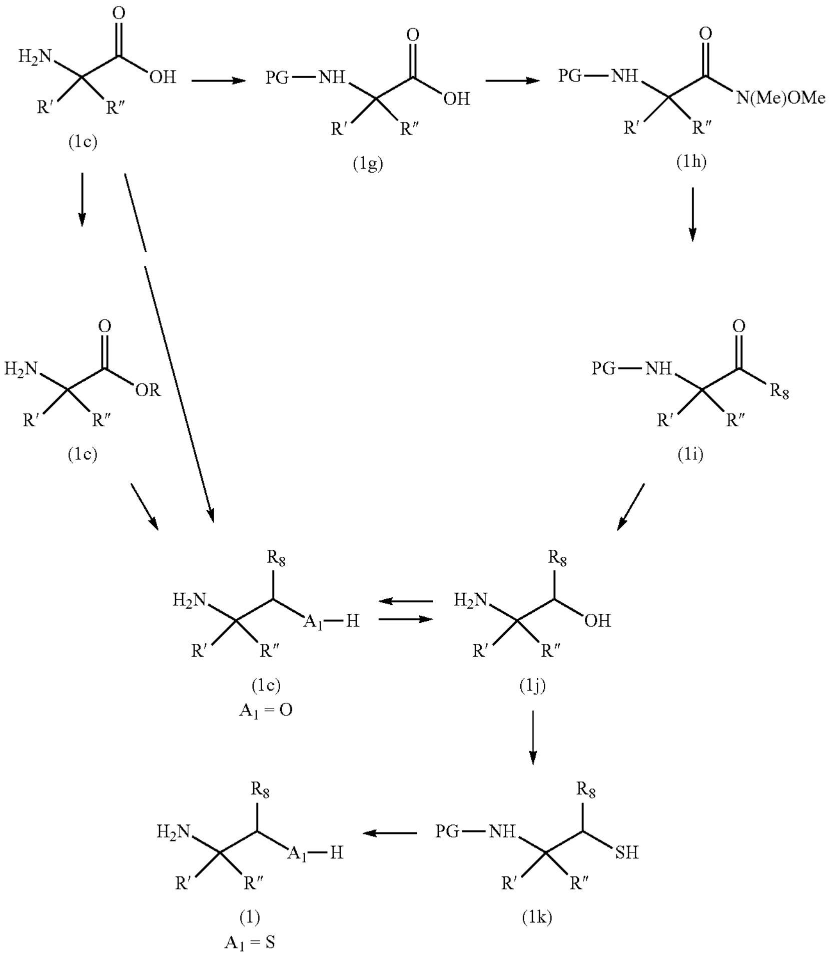

Intermediates of Structure (1) where $A_1$=O, 1,2-aminoalcohols, are well known in the chemical literature, with numerous commercially available derivatives and many reported methods of synthesis. For chiral aminoalcohol Intermediates (1), methods for synthesis of racemic and enantio-enriched compounds are known. Aminoalcohol Intermediates (1) are readily prepared from alpha-aminoacids (1c), which also have broad commercial availability and are extensively reported in the literature. For example, the preparation and conversion of intermediates of Structures (1c) to (1) are described in Chem. Revs 1996, 96, 835; J. Med. Chem. 2020, 63, 10188; J. Org. Chem. 2013, 78, 12726; Tetrahedron 1994, 50, 1539; Chem. Revs 2007, 107, 4584. The preparation of aminoacids (1c) from ketones (1a) is described in Chemical Reviews 2017, 117, 13757; Molecules 2021, 26, 1707. The use of N-protecting groups, including tert-butoxycarbonyl (Boc), is described in T. W. Greene, *Protective Groups in Organic Synthesis*, John Wiley & Sons, New York, 1991.

The conversion of aminoacid Intermediate (1c) to aminoalcohol Intermediate (1) where $A_1$=O and $R_8$=H is well known by direct addition of a suitable hydride source, preferably lithium aluminum hydride. Alternatively, aminoacid Intermediate (1c) can be treated with an anhydrous alcoholic solvent and acid, preferably methanol and hydrogen chloride, to afford an intermediate ester (1f) where preferably R=methyl, followed by reduction with a suitable hydride source, preferably lithium aluminum hydride or lithium borohydride, to provide aminoalcohols Intermediate (1). Where $R_8$=alkyl, the alpha-aminoacid Intermediate (1c) may be transformed to an N-protected derivative Intermediate (1g), where PG=a suitable protecting group, preferably tert-butoxycarbonyl, followed by conversion to an amide derivative Intermediate (1h) that is suitable for the selective addition of appropriate $R_8$ groups. Nucleophilic addition of an appropriate alkyl-organometallic reagent, preferably a Grignard or organolithium reagent, can provide ketone Intermediate (1i). Reduction of ketone Intermediate (1i) by reaction with a hydride reagent, preferably sodium or lithium borohydride, can afford the N-protected 1,2-aminoalcohol Intermediate (1j). Cleavage of the N-protecting group, preferably with trifluoroacetic acid or hydrochloric acid when PG=tert-butoxycarbonyl, can afford aminoalcohol Intermediate (1). Aminoalcohol Intermediate (1) can also be readily converted to N-protected 1,2-aminoalcohol Intermediate (1j) by standard methods; preferably PG=tert-butoxycarbonyl, by reaction with di-tert-butyldicarbonate.

Alternatively, an aminoacid Intermediate (1c) that is not commercially available or known in the literature may be synthesized from an appropriate ketone starting material Intermediate (1a). Conversion of ketone Intermediate (1a) to aminonitrile Intermediate (1b) and then to aminoacid Intermediate (1c) via the Strecker reaction is widely known in the literature. Ketone (1a) can be treated with a source of ammonia, such as ammonium chloride and/or ammonium hydroxide, and with a source of cyanide, preferably sodium or potassium cyanide, or trimethylsilyl cyanide, in a protic solvent such as water or methanol, to afford the aminonitrile Intermediate (1b). The aminonitrile Intermediate (1b) can be hydrolyzed to the aminoacid Intermediate (1c) with an aqueous acid, preferably hydrochloric acid or sulfuric acid, and heat. An alternative route to convert ketone Intermediate (1a) to aminoacid Intermediate (1c) is by treatment with a cyanide source, preferably sodium or potassium cyanide, or trimethylsilylcyanide, and ammonium carbonate to provide the hydantoin Intermediate (1d). Some hydantoin Intermediates (1d) can be cleaved directly to aminoacid Intermediates (1c) by treatment with strong aqueous base, preferably potassium or barium hydroxide, and heat, or by treatment with strong acid, such as hydrobromic acid in phosphoric acid, and heat. Alternatively, hydantoin Intermediate (1d) can first be activated for hydrolysis by treatment with di-tert-butyldicarbonate to afford Intermediate (1e), then treated with strong aqueous base, preferably potassium hydroxide, to afford aminoacid Intermediate (1c).

Intermediates of Structure (1) where $A_1$=S, 1,2-aminothiols, are well known in the chemical literature, with numerous commercially available derivatives and many reported methods of synthesis. Aminothiol Intermediates (1) where $A_1$=S, or the corresponding N-protected aminothiol Intermediates (1k), can be readily prepared from aminoalcohol Intermediates (1) where $A_1$=O, or the corresponding N-protected aminoalcohol Intermediates (1j), by analogy to established synthetic methods, such as those described in Synlett 2000, 908; J. Med. Chem. 2014, 57, 5748; Eur. J. Org. Chem. 2019, 7432.

The conversion of N-protected aminoalcohol Intermediate (1j) to N-protected aminothiol Intermediate (1k) is achieved by activation of the alcohol for displacement by a suitable sulfur-derived nucleophile, followed by protecting group or oxidation state manipulation of the sulfur derivative to provide the aminothiol Intermediate (1k). For example, activation of the alcohol may be achieved by a combination of triphenylphosphine and N-bromosuccinimide, or by a combination of methanesulfonylchloride and triethylamine. Reaction of the activated alcohol with a sulfur-derived nucleophile such as potassium thioacetate, or benzylmercaptan or para-methoxybenzylmercaptan and a base such as potassium tert-butoxide or sodium hydride, followed by deprotection of the protected thiol affords N-protected aminothiol Intermediate (1k). Cleavage of the N-protecting group, preferably with trifluoroacetic acid or hydrochloric acid when PG=tert-butoxycarbonyl, can afford aminothiol Intermediate (1) where $A_1$=S.

Reaction Scheme II outlines general procedures for the synthesis of intermediates that can be used to provide compounds of the present invention having Formula (I). R' and R" represent chemical groups that are described within the scope of the Claims; Boc=tert-butoxycarbonyl. The conversion of commercially available Intermediate (2a) to Intermediate (2) can proceed via well-precedented literature conditions for sequential SNAr reaction and borylation. The conversion of Intermediate (2b) to Intermediate (3b) either via sequential SNAr reaction with Intermediate (1) and N-protecting group introduction, or via SNAr reaction with an N-protected Intermediate (1j/1k) and borylation to Intermediate (3) is also well-precedented. For example, SNAr reactions with appropriate nucleophiles are described in US20140142102; J. Org. Chem. 1983, 48, 3341; J. Heterocyclic Chem. 1988, 25, 1173; Org. Proc. Res. & Dev. 2021, 25, 2351; Org. Proc. Res. & Dev. 2019, 23, 783; WO201912991; Org. Prep. Proc. Int. 2022, 34, 405; Tetrahedron 2013, 69, 1663. Borylation of aromatic bromides to convert Intermediate (2b) to Intermediate (2), or Intermediate (3b) to Intermediate (3), can be conducted as described in WO2011061168; WO2014140078. The use of N-protecting groups, including tert-butoxycarbonyl (Boc), is described in T. W. Greene, *Protective Groups in Organic Synthesis*, John Wiley & Sons, New York, 1991.

Reaction Scheme II
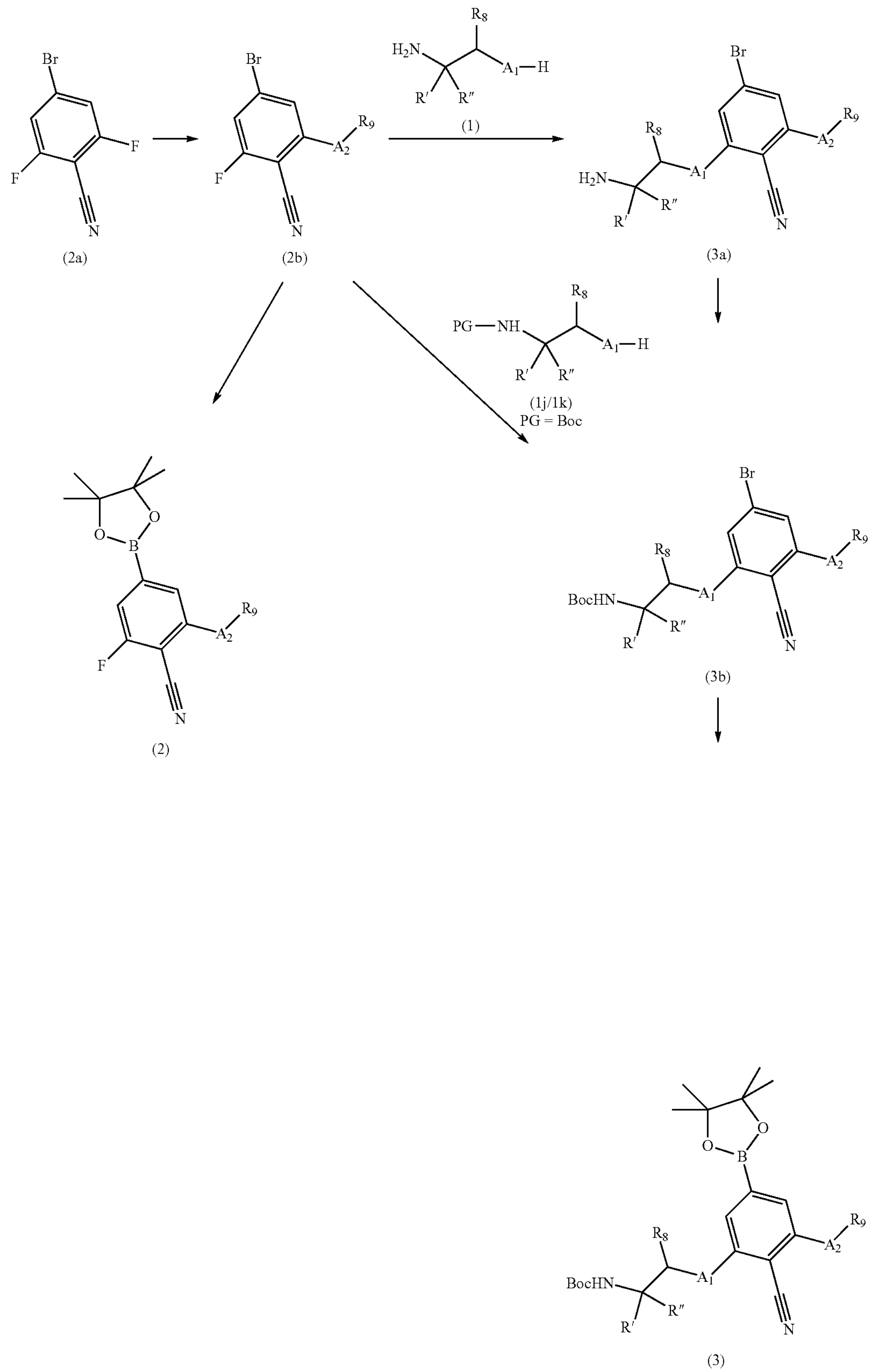
(2a) (2b) (3a) (2) (3b) (3)

The conversion of Intermediate (2a) to (2b) can be readily accomplished by reaction with a suitable nucleophile, such as an alcohol or thiol in the presence of a suitable base such as sodium hydride, or by reaction with a metal salt of an alcohol or thiol, preferably sodium methoxide or sodium thiomethoxide, in an appropriate solvent, preferably methanol or tetrahydrofuran, at a temperature preferably between 0-25° C. Borylation of Intermediate (2b) to afford Intermediate (2) may be effected under standard palladium-catalyzed reaction conditions, using a catalyst such as [1,1'-bis(diphenylphosphino)ferrocene]dichloropalladium(II), a base such as potassium acetate, and a borylating reagent such as bis(pinacolato)diboron, in a suitable solvent such as dioxane, at a temperature preferably between 80-110° C. Alternatively, Intermediate (2b) can be reacted with an aminoalcohol or aminothiol Intermediate (1) under basic conditions in a suitable solvent, preferably potassium hexamethyldisilazide in tetrahydrofuran or sodium tert-butoxide in tert-butanol, to afford Intermediate (3a). N-Protection of Intermediate (3a), preferably as a tert-butyl carbamate by reaction with di-tert-butyldicarbonate, can afford Intermediate (3b). Alternatively, Intermediate (2b) can be reacted with an N-protected aminoalcohol Intermediate (1j), preferably where the N-protecting group is tert-butoxycarbonyl (Boc), and an appropriate base such as potassium hexamethyldisilazide or sodium tert-butoxide, to provide Intermediate (3b). Alternatively, Intermediate (2b) can be reacted with an N-protected aminothiol Intermediate (1k), preferably where the N-protecting group is tert-butoxycarbonyl (Boc), and an appropriate base, such as sodium carbonate or potassium carbonate, to provide Intermediate (3b). Borylation of Intermediate (3b) to provide Intermediate (3) can be effected under standard palladium-catalyzed reaction conditions, using a catalyst such as [1,1'-bis(diphenylphosphino)ferrocene]dichloropalladium(II), a base such as potassium acetate, and a borylating reagent such as bis(pinacolato)diboron, in a suitable solvent such as dioxane, at a temperature preferably between 80-110° C.

Reaction Scheme IIIA and Reaction Scheme IIIB outline general procedures for the synthesis of compounds of the present invention having Formula (I). R' and R" represent chemical groups that are described within the scope of the Claims; Boc=tert-butoxycarbonyl; hal represents a halogen, preferably bromine or iodine. Intermediate (4b) and Intermediate (4e) have many commercially available derivatives. Alternatively, the preparation of substituted pyrazolopyridines such as Intermediate (4b) via precursor pyridines Intermediate (4a) and the preparation of substituted imidazopyridines such as Intermediate (4e) via precursor pyridines Intermediate (4d) are described in the chemical literature. For example, pyrazolopyridines Intermediate (4b) and Intermediate (4c) can be prepared by analogy to procedures in J. Med. Chem. 2015, 58, 8713; WO2014078802. Imidazopyridines Intermediate (4e) and Intermediate (4c) can be prepared by analogy to procedures in Bioorg. Med. Chem. 2020, 28, 115775; J. Med. Chem. 2015, 58, 8713; WO2019105886. Those skilled in the art will recognize that when $R_4$, $R_5$, or $R_6$=halogen on Intermediate (4b) or Intermediate (4e), such a halogen may be converted to other substituents via standard methods. For example, conversion of Intermediate (4b) or Intermediate (4e), $R_5$=bromide to $R_5$=(substituted)amino, can be accomplished by analogy to procedures described in WO2015108490; WO2020150626; WO2021140122; WO2014078802. The reaction of Intermediate (4c) with boronate Intermediate (2) to afford Intermediate (40, or of Intermediate (4c) with Intermediate (3) to afford Intermediate (4g), can be conducted under the general conditions described in Bioorg. Med. Chem. 2020, 28, 115775; J. Med. Chem. 2015, 58, 8713; WO2019105886. The preparation of compounds of Formula (I) from Intermediate (4f) by reaction with Intermediate (1) can be completed by analogy to procedures described in Organic Process Research & Development 2021, 25, 2351; Organic Process Research & Development 2019, 23, 783; Tetrahedron 2013, 69, 1663; Journal of Organic Chemistry 1983, 48, 3341. Alternatively, Intermediate (4f) can be reacted with N-protected aminoalcohols Intermediate (1j) or N-protected aminothiols Intermediate (1k) to afford Intermediate (4g) by analogy to procedures in Tetrahedron 2013, 69, 1663; Organic Preparations and Procedures International 2002, 34, 405; WO2019212991. Alternatively, compounds of Formula (I) may be prepared from Intermediate (4g) by cleavage of the N-tert-butoxycarbonyl (Boc) group as described in T. W. Greene, *Protective Groups in Organic Synthesis*, John Wiley & Sons, New York, 1991.

Reaction Scheme IIIA

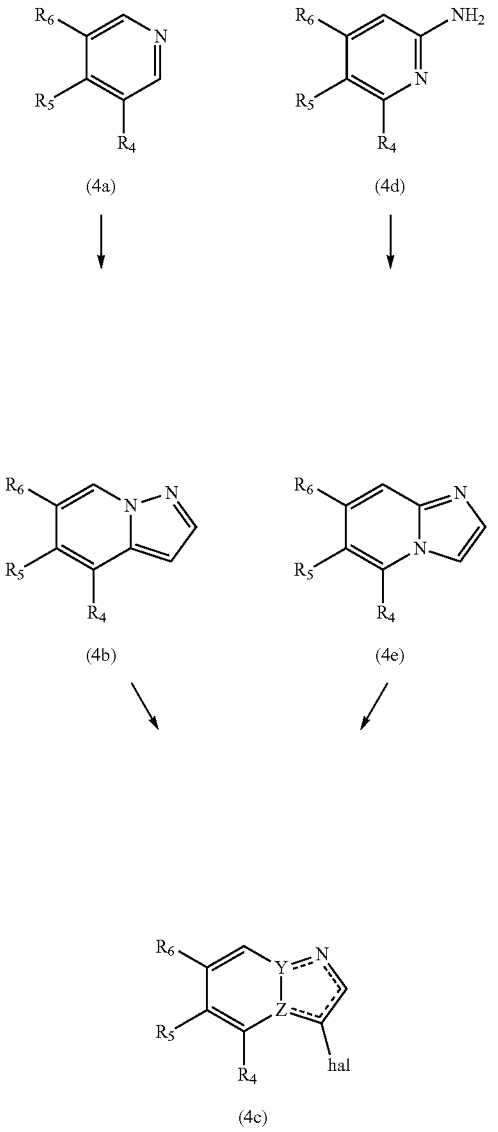

(4a) (4d) (4b) (4e) (4c)

Reaction Scheme IIIB

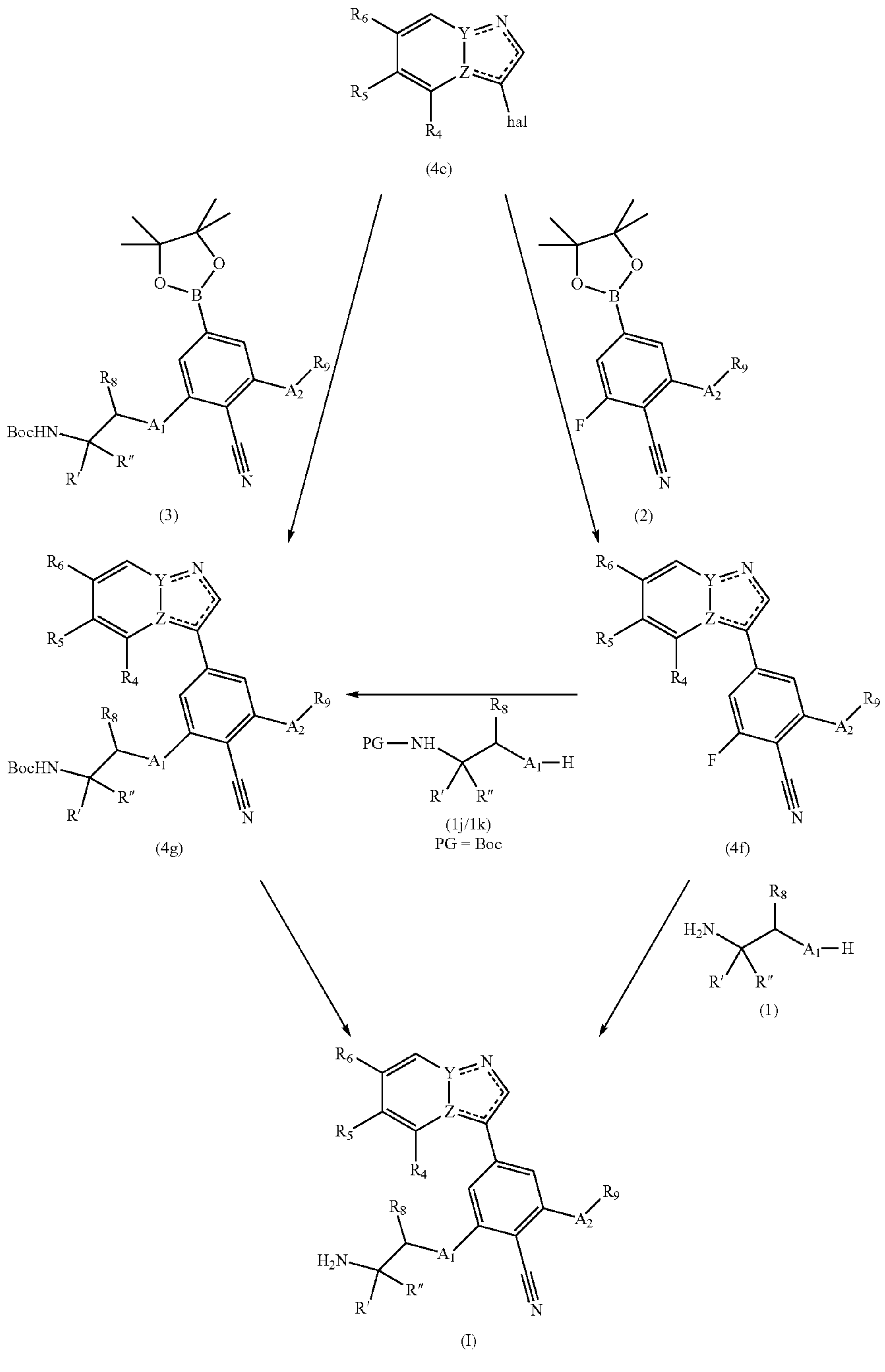

Pyrazolopyridine Intermediate (4b) or imidazopyridine Intermediate (4e) can be reacted with a halogenating reagent, preferably a brominating reagent such as N-bromo-succinimide or an iodinating reagent such as N-iodosuccin-imide, to afford Intermediate (4c). Palladium-catalyzed reaction between Intermediate (4c) and boronate Intermediate (2) or boronate Intermediate (3), using a catalyst such as bis(triphenylphos-phine)palladium(II) dichloride or [1,1'-bis (diphenylphosphino)ferrocene]dichloro-palladium(II), a base such as potassium carbonate or tribasic potassium phosphate, in a suitable solvent such as aqueous dioxane or N,N-dimethylformamide, at an appropriate temperature, preferably between 80-110° C., will afford Intermediate (40 or Intermediate (4g), respectively. Intermediate (40 can be reacted with aminoalcohol or aminothiol Intermediate (1) under basic conditions in a suitable solvent, preferably potassium hexamethyldisilazide in tetrahydrofuran or sodium tert-butoxide in tert-butanol, to afford compounds of Formula (I). Alternatively, Intermediate (40 can be reacted with an N-protected aminoalcohol Intermediate (1j), preferably where the N-protecting group is tert-butoxycarbonyl (Boc), and an appropriate base such as potassium hexamethyldisilazide or sodium tert-butoxide, to provide Intermediate (4g). Alternatively, Intermediate (4f) can be reacted with an N-protected aminothiol Intermediate (1k), preferably where the N-protecting group is tert-butoxycarbonyl (Boc), and an appropriate base such as sodium carbonate or potassium carbonate, to provide Intermediate (4g). Intermediate (4g) can be treated with acid, preferably trifluoroacetic acid or hydrogen chloride, to afford compounds of Formula (I). Compounds of Formula (I) that are chiral may be phase, followed by conversion of each stereoisomer separately to compounds of Formula (I).

Reaction Scheme IV outlines an alternative general procedure for the synthesis of compounds of the present invention having Formula (I), where Y═C and Z═N. R' and R" represent chemical groups that are described within the scope of the Claims; Boc=tert-butoxycarbonyl. The vinyl ether Intermediate (5) can be prepared under a range of conditions analogous to those described in WO2021013864; WO2019148132; Tetrahedron Lett 2000, 41, 4579; Tetrahedron Lett 1999, 40, 6193; Chem. Biol.& Drug Design 2015, 86, 180; J. Amer. Chem. Soc. 2011, 133, 32; Org. Lett 2013, 15, 1838; J. Amer. Chem. Soc. 2018, 140, 126; Org. Lett. 2002, 4, 4399. Intermediate (5) can be reacted with 2-aminopyridine Intermediate (4d) to afford Intermediate (4g) under conditions analogous to those described in WO2021013864; WO2019148132. Compounds of Formula (IA) may be prepared from Intermediate (4g) by cleavage of the N-tert-butoxycarbonyl (Boc) group as described in T. W. Greene, *Protective Groups in Organic Synthesis*, John Wiley & Sons, New York, 1991.

Reaction Scheme IV

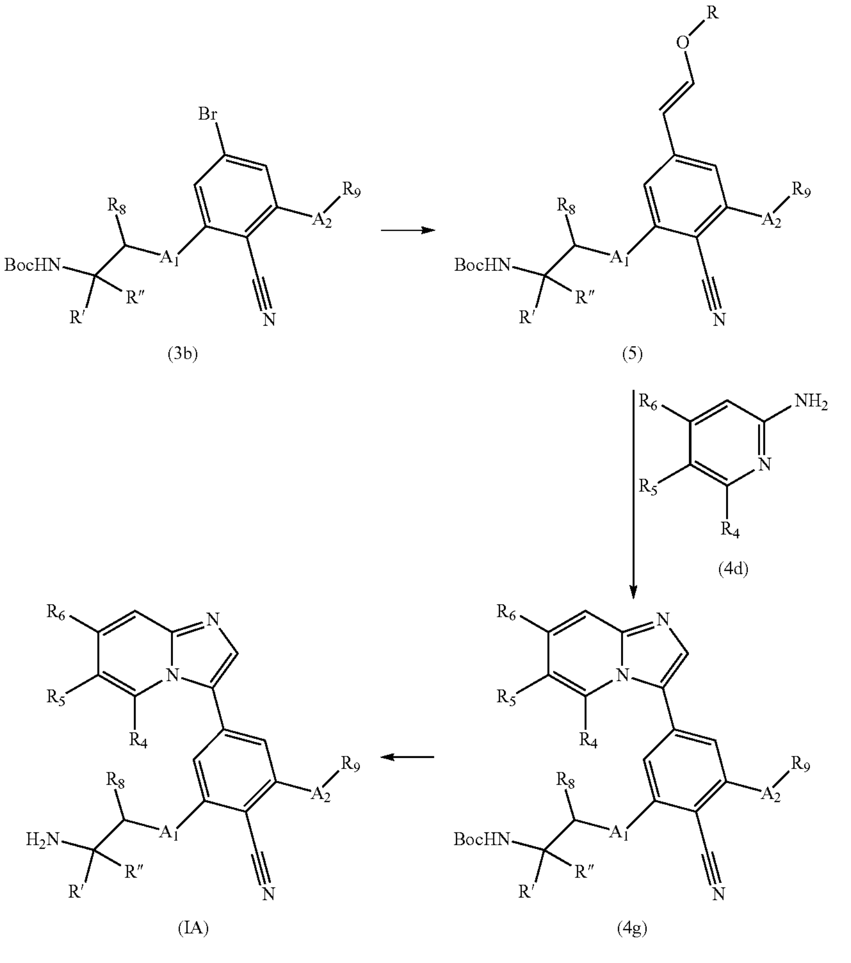

separated to individual stereoisomers by chromatography using a chiral stationary phase to separate racemic and/or diastereomeric compounds of Formula (I). Alternatively, chiral precursors such as Intermediate (3a), Intermediate (3b), or Intermediate (4g) may be separated to individual stereoisomers by chromatography using a chiral stationary phase Intermediate (5) can be prepared from bromide Intermediate (3b) by reaction in a palladium-catalyzed reaction with a suitable coupling partner, preferably [1,1'-bis(diphenylphosphino)ferrocene]di-chloropalladium(II) and (E)-2-(2-ethoxyvinyl)-4,4,5,5-tetramethyl-1,3,2-dioxaborolane, in the presence of a base such as potassium phosphate tribasic, in a suitable solvent such as aqueous dioxane, at a temperature preferably between 80-110° C. Intermediate (4g) can be prepared from Intermediate (5) and Intermediate (4d) by cyclization in the presence of an oxidant, preferably N-bromosuccinimide, in an appropriate solvent such as aqueous dioxane. Intermediate (4g) can be treated with acid, preferably trifluoroacetic acid or hydrogen chloride, to afford compounds of Formula (IA). Compounds of Formula (IA) that are chiral may be separated to individual stereoisomers by chromatography using a chiral stationary phase to separate racemic and/or diastereomeric compounds of Formula (IA). Alternatively, chiral precursors such as Intermediate (4g) may be separated to individual stereoisomers by chromatography using a chiral stationary phase, followed by conversion of each stereoisomer separately to compounds of Formula (IA).

PREPARATIONS AND EXAMPLES

The following non-limiting Preparations and Examples illustrate the preparation of compounds and salts of the present invention. In the Examples and Preparations that are set out below, and in the aforementioned Schemes, the following abbreviations, definitions and analytical procedures may be referred to. Other abbreviations common in the art may also be used. Compounds of the present invention were named using ChemDraw Professional™ version 20 (Perkin Elmer) or were given names which are consistent with IUPAC nomenclature.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g., s, singlet; d, doublet; t, triplet; q, quartet; quin, quintet; m, multiplet; br, broad. The following abbreviations have been used for common NMR solvents: $CD_3CN$, deuteroacetonitrile; $CDCl_3$, deuterochloroform; DMSO-$d_6$, deuterodimethylsulfoxide; and MeOD, deuteromethanol. Where appropriate, tautomers may be recorded within the NMR data; and some exchangeable protons may not be visible. Some resonances in the NMR spectrum appear as complex multiplets because the isolate is a mixture of two conformers.

Mass spectra were recorded using electron impact ionization (EI), electrospray ionization (ESI) or atmospheric pressure chemical ionization (APCI). The observed ions are reported as MS m/z and may be positive ions of the compound $[M]^+$, compound plus a proton $[M+H]^+$, or compound plus a sodium ion $[M+Na]^+$. In some cases the only observed ions may be fragment ions reported as [M+H-(fragment lost)]$^+$. Where relevant, the reported ions are assigned for isotopes of chlorine ($^{35}$Cl and/or $^{37}$Cl), bromine ($^{79}$Br and/or $^{81}$Br) and tin ($^{120}$Sn).

Wherein TLC, chromatography or HPLC has been used to purify compounds, one skilled in the art may choose any appropriate solvent or combination of solvents to purify the desired compound. Chromatographic separations (excluding HPLC) were carried out using silica gel adsorbent unless otherwise noted.

All reactions were carried out using continuous stirring under an atmosphere of nitrogen or argon gas unless otherwise noted. In some cases, reactions were purged with nitrogen or argon gas prior to the start of the reaction. In these cases, the nitrogen or argon gas was bubbled through the liquid phase of the mixture for the approximate specified time. Solvents used were commercial anhydrous grades. All starting materials were commercially available products. In some cases, starting materials were prepared according to reported literature procedures. It will be apparent to one skilled in the art that the word "concentrated" as used herein generally refers to the practice of evaporation of solvent under reduced pressure, typically accomplished by the use of a rotary evaporator.

Chemical structures were named using ChemDraw Professional 20.

Abbreviations $B_2$(pin) 2: bis(pinacolato)diboron
$Boc_2O$: di-tert-butyldicarbonate
$CH_3CN$: acetonitrile
$CDCl_3$: deuterochloroform
DCM: dichloromethane
DMF: N,N-dimethylformamide
DMSO: dimethylsulfoxide
DMSO-$d_6$: hexadeuterodimethylsulfoxide
$Et_2O$: diethylether
EtOAc: ethyl acetate
EtOH: ethanol
HOAc: acetic acid
HPLC: high performance liquid chromatography
$iPr_2NEt$: N,N-diisopropylethylamine
iPrOH: 2-propanol
KHMDS: potassium hexamethyldisilazide
KOAc: potassium acetate
h: hours
M: molar
$Me_2NH$: dimethylamine
MeOH: methanol
MeOD: tetradeuteromethanol
MeTHF: 2-methyl-tetrahydrofuran
mg: milligrams
min: minutes
mL: milliliters
mmol: millimoles
MS: mass spectrometry, (M): molecular mass
MsOH: methanesulfonic acid
MTBE: methyl tert-butyl ether
N: normal
NaHMDS: sodium hexamethyldisilazide
NaOMe: sodium methoxide
NaOtBu: sodium tert-butoxide
NBS: N-bromosuccinimide
NIS: N-iodosuccinimide
NMR: nuclear magnetic resonance; s, singlet; d, doublet; t, triplet; q, quartet; quin, quintet; m, multiplet; br s, broad singlet; app, apparent.
$PdCl_2$(dppf)-DCM: [1,1'-bis(diphenylphosphino)ferrocene]dichloropalladium(II), complex with dichloromethane
$PdCl_2$(dppf): [1,1'-bis(diphenylphosphino)ferrocene]dichloropalladium(II)
$Pd(OAc)_2$: palladium(II) acetate
$Pd(PPh_3)_2Cl_2$: Bis(triphenylphosphine)palladium(II) dichloride
PE: petroleum ether
SFC: supercritical fluid chromatography
TFA: trifluoroacetic acid
THF: tetrahydrofuran
TMSCN: trimethylsilyl cyanide
UPLC: ultra-performance liquid chromatography
Xantphos: 4,5-bis(diphenylphosphino)-9,9-dimethylxanthene XPhos: 2-dicyclohexylphosphino-2',4',6'-triisopropylbiphenyl XPhos-G3-Palladacycle: (2-dicyclohexylphosphino-2',4',6'-triisopropyl-1,1'-biphenyl)[2-(2'-amino-1,1'-biphenyl)]palladium(II) methanesulfonate Preparation A 4-Bromo-2-fluoro-6-methoxybenzonitrile. A solution of NaOMe in MeOH (5.4 M, 688 mL, 3.72 mol) was added to a solution of 4-bromo-2,6-difluorobenzonitrile (900 g, 4.13 mol) in MeOH (3.81 L) at 0° C., and the reaction was stirred for 60 h at 0° C. $H_2O$ (2.61 L) was added, and the resulting mixture was stirred for 2 h at 25° C., then the solids were collected by filtration and were dried to afford 4-bromo-2-fluoro-6-methoxybenzonitrile (894 g). $^1H$ NMR (400 MHz, $CDCl_3$) δ 7.00 (dd, 1H), 6.94 (app t, 1H), 3.95 (s, 3H).

Preparation B

4-Bromo-2-fluoro-6-(methylthio)benzonitrile. $CH_3SNa$ (6.21 g, 88.6 mol) was added slowly to a solution of 4-bromo-2,6-difluorobenzonitrile (20.0 g, 91.7 mmol) in THF (300 mL) at 0° C. The resulting mixture was allowed to warm slowly to 15° C. and was stirred for 3 days, then was diluted with aqueous $NH_4Cl$ solution and was extracted with EtOAc (3×). The combined organics were washed with brine (2×), dried over $Na_2SO_4$, filtered, and concentrated. The resulting residue was purified by silica gel chromatography (4-95% EtOAc/PE) to afford 4-bromo-2-fluoro-6-(methylthio)benzonitrile as a white solid (18.3 g). $^1H$ NMR (400 MHz, DMSO-$d_6$) δ 7.68 (dd, 1H), 7.48 (d, 1H), 2.67 (s, 3H).

Preparation C

2-Fluoro-6-(methylthio)-4-(4,4,5,5-tetramethyl-1,3,2-dioxaborolan-2-yl)benzonitrile. $PdCl_2$(dppf) (1.19 g, 1.63 mmol) was added to a solution of 4-bromo-2-fluoro-6-(methylthio)benzonitrile (8.00 g, 32.5 mmol), $B_2(pin)_2$ (8.25 g, 32.5 mmol), and KOAc (7.98 g, 81.3 mmol) in dioxane (140 mL) under $N_2$. The resulting mixture was stirred at 90° C. for 16 h, then was concentrated. The resulting residue was purified by silica gel chromatography to afford 2-fluoro-6-(methylthio)-4-(4,4,5,5-tetramethyl-1,3,2-dioxaborolan-2-yl)benzonitrile as a yellow solid (6.5 g). $^1H$ NMR (400 MHz, $CDCl_3$) δ 7.44 (s, 1H), 7.33 (d, 1H), 2.61 (s, 3H), 1.35 (5, 12H).

Preparation D

2-Fluoro-4-(5-methoxyimidazo[1,2-a]pyridin-3-yl)-6-(methylthio)benzonitrile. A solution of dioxane (100 mL) and $H_2O$ (10 mL) was sparged with $N_2$ for 10 min, then was charged to a flask containing $K_3PO_4$ (22.2 g, 105 mmol), 3-bromo-5-methoxyimidazo[1,2-a]pyridine (10.0 g, 42.0 mmol), 2-fluoro-6-(methylthio)-4-(4,4,5,5-tetramethyl-1,3,2-dioxaborolan-2-yl)benzonitrile (12.9 g, 43.9 mmol), and $PdCl_2$(dppf)-DCM, (1.76 g, 2.09 mmol) under an atmosphere of $N_2$. The resulting mixture was heated at 80° C. for 20 h, then was concentrated to remove dioxane. The resulting suspension was diluted with water and was filtered. The collected solids purified by silica gel chromatography (2-10% MeOH/DCM) to afford 2-fluoro-4-(5-methoxyimidazo[1,2-a]pyridin-3-yl)-6-(methylthio)benzonitrile (6.30 g). $^1H$ NMR (400 MHz, $CDCl_3$) δ 7.62 (s, 1H), 7.37 (dd, 1H), 7.30 (dd, 1H), 7.12 (d, 1H), 7.00 (dd, 1H), 6.16 (dd, 1H), 3.93 (s, 3H), 2.60 (s, 3H). MS $(M+H)^+$ 314.0.

Example 1

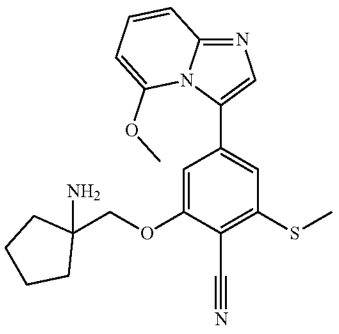 [SMILES: COc1cccc2ncc(-c3cc(OCC4(N)CCCC4)c(C#N)c(SC)c3)n12]

2-((1-Aminocyclopentyl)methoxy)-4-(5-methoxyimidazo[1,2-a]pyridin-3-yl)-6-(methylthio)benzonitrile. A solution of NaHMDS in THF (1.0 M, 26.8 mL, 26.8 mmol) was added dropwise to a solution of 2-fluoro-4-(5-methoxyimidazo[1,2-a]pyridin-3-yl)-6-(methylthio)benzonitrile (6.00 g, 19 mmol) and (1-aminocyclopentyl)methanol (2.67 g, 23.2 mmol) in THF (12 mL). The resulting mixture was stirred at ambient temperature for 16 h. Aqueous phosphate buffer (pH 7, 100 mL) was added and the resulting mixture was concentrated to remove the THF, then was extracted with MeTHF (3×). The combined organic layers were washed with brine, dried over $Na_2SO_4$, and concentrated. Silica gel chromatography (50% MeOH-DCM) afforded 2-((1-aminocyclopentyl)meth-oxy)-4-(5-methoxyimidazo[1,2-a]pyridin-3-yl)-6-(methylthio)benzonitrile as a solid (3.4 g). $^1H$ NMR (600 MHz, DMSO-$d_6$) δ 7.76 (s, 1H), 7.39 (dd, 1H), 7.29 (d, 1H), 7.08 (s, 1H), 7.05 (s, 1H), 6.45 (d, 1H), 3.99 (s, 2H), 3.93 (s, 3H), 2.61 (s, 3H), 1.82-1.72 (m, 2H), 1.72-1.55 (m, 4H), 1.48-1.41 (m, 2H). MS $(M+H)^+$ 409.4.

The following examples were synthesized by analogous methods and starting materials as described for 2-((1-aminocyclopentyl)methoxy)-4-(5-methoxyimidazo[1,2-a]pyridin-3-yl)-6-(methylthio)benzonitrile.

Example 2

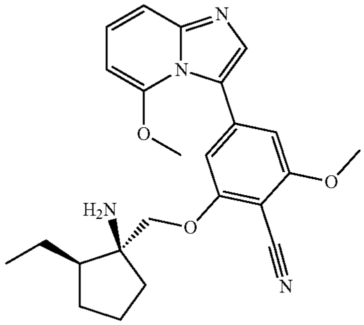

-continued

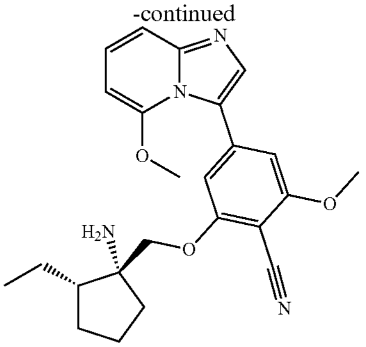

2-(((1S,2R)-1-Amino-2-ethylcyclopentyl)methoxy)-6-methoxy-4-(5-methoxyimidazo[1,2-a]pyridin-3-yl)benzonitrile and 2-(((1R,2S)-1-Amino-2-ethylcyclopentyl)methoxy)-6-methoxy-4-(5-methoxyimidazo[1,2-a]pyridin-3-yl)benzonitrile. Synthesized from 1-amino-2-ethylcyclopentane-1-carboxylic acid (Tetrahedron: Asymmetry 2000, 11, 3231-3252). Enantiomers (absolute stereochemistry not determined) were separated by chiral SFC: Chiral SFC: Phenomenex-Cellulose-2, 100 mm×4.6 mm, 3μ; A: $CO_2$, B: 0.05% Diethylamine/EtOH 60:40 A:B, 2.8 mL/min, 35° C.; retention times, 3.5 min (Peak 1), 4.7 min (Peak 2). 2B Peak 1: $^1$H NMR (400 MHz, MeOD) δ 7.62 (s, 1H), 7.43 (dd, 1H), 7.26 (d, 1H), 6.84 (app s, 2H), 6.41 (d, 1H), 4.01 (s, 2H), 3.97 (s, 3H), 3.96 (s, 3H), 2.1-1.9 (m, 2H), 1.9-1.7 (m, 3H), 1.7-1.6 (m, 2H), 1.6-1.4 (m, 1H), 1.4-1.2 (m, 1H), 0.97 (t, 3H). MS $(M+H)^+$ 421.4. Enantiomeric ratio, 100:0. 2A Peak 2: $^1$H NMR (400 MHz, MeOD) δ 7.62 (s, 1H), 7.43 (dd, 1H), 7.26 (d, 1H), 6.84 (s, 1H), 6.84 (s, 1H), 6.41 (d, 1H), 4.01 (s, 2H), 3.97 (s, 3H), 3.96 (s, 3H), 2.1-1.9 (m, 2H), 1.9-1.6 (m, 5H), 1.6-1.4 (m, 1H), 1.3-1.2 (m, 1H), 0.97 (t, 3H), MS $(M+H)^+$ 421.4. Enantiomeric ratio, 1:99.

Example 3

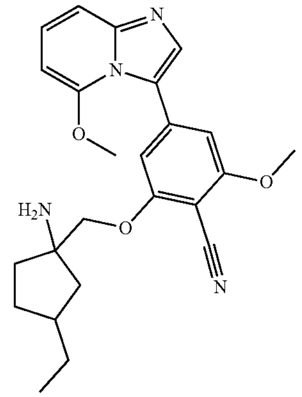 [SMILES: CCC1CCC(N)(COc2cc(-c3cnc4cccc(OC)n34)cc(OC)c2C#N)C1]

2-((1-Amino-3-ethylcyclopentyl)methoxy)-6-methoxy-4-(5-methoxyimidazo[1,2-a]pyridin-3-yl)benzonitrile (Racemic, cis/trans mixture). Synthesized from (1-amino-3-ethylcyclopentyl)methanol. $^1$H NMR (400 MHz, MeOD) δ 7.63-7.62 (m, 1H), 7.45-7.41 (m, 1H), 7.27-7.25 (m, 1H), 6.87-6.83 (m, 2H), 6.42-6.40 (m, 1H), 4.04-3.91 (m, 8H), 2.21-2.10 (m, 1H), 2.04-1.77 (m, 3H), 1.75-1.54 (m, 1H), 1.53-1.17 (m, 4H), 0.97-0.89 (m, 3H). MS (M+H)+421.4.

Example 4

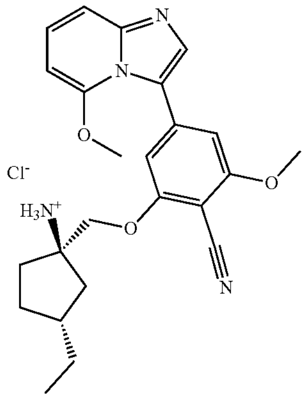

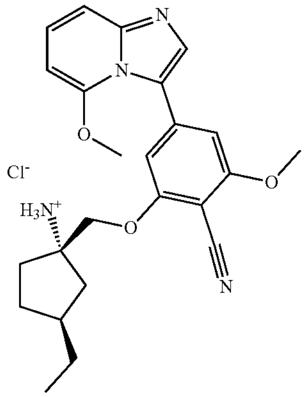

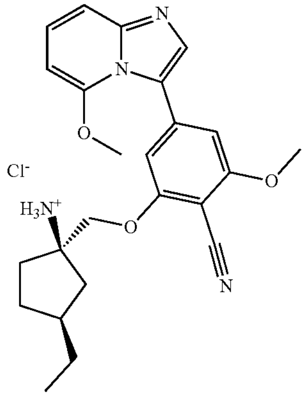

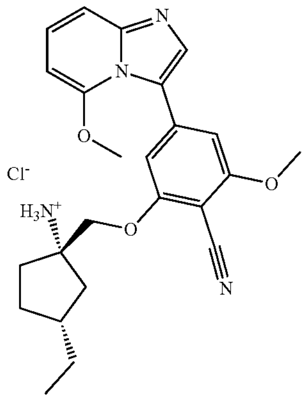

2-(((1R,3R)-1-Amino-3-ethylcyclopentyl)methoxy)-6-methoxy-4-(5-methoxyimidazo[1,2-a]pyridin-3-yl) benzonitrile hydrochloride and 2-(((1S,3S)-1-Amino-3-ethylcyclopentyl)methoxy)-6-methoxy-4-(5-methoxyimidazo[1,2-a]pyridin-3-yl)benzonitrile hydrochloride and 2-(((1R,3S)-1-Amino-3-ethylcyclopentyl)methoxy)-6-methoxy-4-(5-methoxyimidazo[1,2-a]pyridin-3-yl)benzonitrile hydrochloride and 2-(((1S,3R)-1-Amino-3-ethylcyclopentyl)methoxy)-6-methoxy-4-(5-methoxyimidazo[1,2-a]pyridin-3-yl)benzonitrile hydrochloride. Prepared from 2-((1-amino-3-ethylcyclopentyl)methoxy)-6-methoxy-4-(5-methoxyimidazo[1,2-a]pyridin-3-yl)benzonitrile (racemic, cis/trans mixture) by N-Boc protection ($Boc_2O$, $Na_2CO_3$, $H_2O$-THF) to afford tert-butyl (1-((2-cyano-3-methoxy-5-(5-methoxyimidazo[1,2-a]pyridin-3-yl)phenoxy)methyl)-3-ethylcyclopentyl)carbamate, then separation of stereoisomers by chiral SFC, then deprotection of the N-Boc group. The four individual stereoisomers of tert-butyl (1-((2-cyano-3-methoxy-5-(5-methoxyimidazo[1,2-a]pyridin-3-yl)phenoxy)methyl)-3-ethylcyclopentyl)carbamate were separated by chiral SFC: Chiralpak AD-3 150 mm×4.6 mm, 3μ; A: $CO_2$, B: 0.05% diethylamine/iPrOH, Gradient: 5%-40% B over 4 min, then 40% B; 2.5 mL/min. Intermediate Stereoisomer 1, retention time 4.6 min; Intermediate Stereoisomer 2, retention time 4.9 min; Intermediate Stereoisomer 3, retention time 5.3 min; Intermediate Stereoisomer 4, retention time 5.5 min. The separated individual Intermediate Stereoisomers (25 mg each) were then independently treated with 2M aqueous HCl solution (2 mL) and MeOH (1 mL) for 16 h to afford the individual stereoisomers of 2-((1-amino-3-ethylcyclopentyl) methoxy)-6-methoxy-4-(5-methoxyimidazo[1,2-a]pyridin-3-yl)benzonitrile (absolute stereochemistry not determined) as hydrochloride salts after lyophilization.

Chiral SFC of separated stereoisomers of 2-((1-amino-3-ethylcyclopentyl)methoxy)-6-methoxy-4-(5-methoxyimidazo[1,2-a]pyridin-3-yl)benzonitrile: Phenomenex-Cellulose-4, 100 mm×4.6 mm, 3μ; A: $CO_2$, B: 0.05% Diethylamine/MeOH, 60:40 A:B, 2.8 mL/min, 40° C.; retention times, 2.62 min (4A), 2.97 min (4B), 2.71 min (4C), 3.49 min (4D). 4A (from Intermediate Stereoisomer 1): $^1$H NMR (400 MHz, DMSO-$d_6$) δ 8.59 (br s, 3H), 8.32 (s, 1H), 8.02-7.96 (m, 1H), 7.61 (d, 1H), 7.14 (s, 1H), 7.13 (s, 1H), 6.99 (d, 1H), 4.27 (s, 2H), 4.03 (s, 3H), 3.94 (s, 3H), 2.20-2.00 (m, 3H), 2.00-1.90 (m, 1H), 1.89-1.79 (m, 1H), 1.49 (dd, 1H), 1.40-1.29 (m, 3H), 0.87 (t, 3H). MS $(M+H)^+$ 421.4. Stereochemical purity by chiral SFC>99%. 4B (from Intermediate Stereoisomer 3): $^1$H NMR (400 MHz, DMSO-$d_6$) δ 8.61 (br s, 3H), 8.34 (s, 1H), 8.04-7.97 (m, 1H), 7.62 (d, 1H), 7.15 (br s, 1H), 7.14 (br s, 1H), 7.00 (d, 1H), 4.27 (s, 2H), 4.03 (s, 3H), 3.94 (s, 3H), 2.22-2.00 (m, 3H), 1.99-1.79 (m, 2H), 1.49 (dd, 1H), 1.41-1.28 (m, 3H), 0.87 (t, 3H). MS $(M+H)^+$ 421.4. Stereochemical purity by chiral SFC>99%. 4C (from Intermediate Stereoisomer 2): $^1$H NMR (400 MHz, DMSO-$d_6$) δ 8.61 (br s, 3H), 8.32 (s, 1H), 7.99 (t, 1H), 7.61 (d, 1H), 7.15 (s, 1H), 7.14 (s, 1H), 6.99 (d, 1H), 4.23 (m, 2H), 4.03 (s, 3H), 3.94 (s, 3H), 2.20 (m, 1H), 2.01-1.78 (m, 4H), 1.56-1.33 (m, 4H), 0.87 (t, 3H). MS $(M+H)^+$ 421.4. Stereochemical purity by chiral SFC>99%. 4D (from Intermediate Stereoisomer 4): $^1$H NMR (400 MHz, DMSO-$d_6$) δ 8.61 (br s, 3H), 8.32 (s, 1H), 7.99 (t, 1H), 7.61 (d, 1H), 7.15 (s, 1H), 7.14 (s, 1H), 6.99 (d, 1H), 4.24 (m, 2H), 4.03 (s, 3H), 3.94 (s, 3H), 2.20 (m, 1H), 2.03-1.76 (m, 4H), 1.60-1.32 (m, 4H), 0.87 (t, 3H). MS $(M+H)^+$ 421.4. Stereochemical purity by chiral SFC 97%.

Example 5

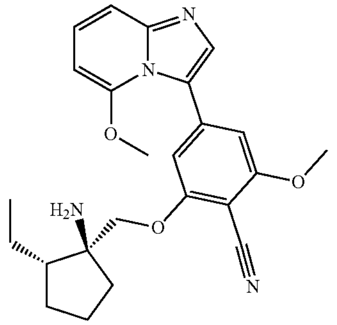

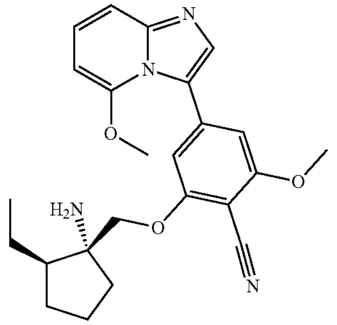

2-(((16,26)-1-Amino-2-ethylcyclopentyl)methoxy)-6-methoxy-4-(5-methoxyimidazo[1,2-a]pyridin-3-yl)benzonitrile and 2-(((1R,2R)-1-Amino-2-ethylcyclopentyl) methoxy)-6-methoxy-4-(5-methoxyimidazo[1,2-a]pyridin-3-yl)benzonitrile. Synthesized from 1-amino-2-ethylcyclopentane-1-carboxylic acid (Tetrahedron: Asymmetry 2000, 11, 3231-3252). Enantiomers (absolute stereochemistry not determined) were separated by chiral SFC: Chiral SFC: Phenomenex-Cellulose-2, 100 mm×4.6 mm, 3μ; A: $CO_2$, B: 0.05% Diethylamine/EtOH 60:40 A:B, 2.8 mL/min, 35° C.; retention times, 3.99 min (Peak 1), 6.64 min (Peak 2). 5A Peak 1: $^1$H NMR (400 MHz, MeOD) δ 7.63 (s, 1H), 7.48-7.41 (m, 1H), 7.26 (d, 1H), 6.86 (s, 1H), 6.86 (s, 1H), 6.42 (d, 1H), 4.07-3.99 (m, 2H), 3.97 (s, 6H), 2.13-1.96 (m, 2H), 1.82-1.65 (m, 5H), 1.53-1.42 (m, 1H), 1.23-1.10 (m, 1H), 0.96 (t, 3H). MS $(M+H)^+$ 421.4. Enantiomeric ratio, 100:0. 5B Peak 2: $^1$H NMR $^1$H NMR (400 MHz, MeOD) δ 7.63 (s, 1H), 7.46-7.41 (m, 1H), 7.26 (d, 1H), 6.86 (s, 1H), 6.86 (s, 1H), 6.42 (d, 1H), 4.06-3.99 (m, 2H), 3.97 (s, 6H), 2.13-1.95 (m, 2H), 1.81-1.64 (m, 5H), 1.55-1.41 (m, 1H), 1.23-1.10 (m, 1H), 0.96 (t, 3H). MS $(M+H)^+$ 421.4. Enantiomeric ratio, 0.8:99.2.

Example 6

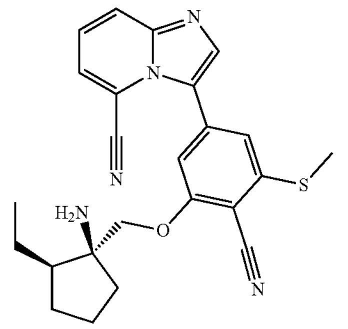

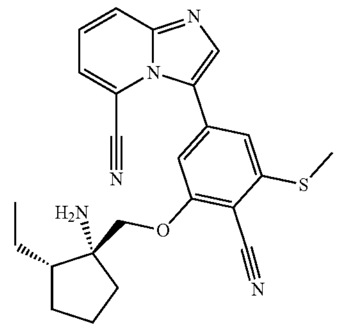

3-(3-(((1S,2R)-1-Amino-2-ethylcyclopentyl)methoxy)-4-cyano-5-(methylthio)phenyl)imidazo[1,2-a]pyridine-5-carbonitrile and 3-(3-(((1R,2S)-1-Amino-2-ethylcyclopentyl)methoxy)-4-cyano-5-(methylthio)phenyl)imidazo[1,2-a]pyridine-5-carbonitrile. Synthesized from 1-amino-2-ethylcyclopentane-1-carboxylic acid (Tetrahedron: Asymmetry 2000, 11, 3231-3252). Enantiomers (absolute stereochemistry not determined) were separated by chiral SFC: Chiral SFC: Phenomenex-Cellulose-2, 100 mm×4.6 mm, 3μ; A: $CO_2$, B: 0.05% Diethylamine/EtOH 50:50 A:B, 2.8 mL/min, 35° C.; retention times, 2.32 min (Peak 1), 3.09 min (Peak 2). 6A Peak 1: $^1$H NMR (400 MHz, $CDCl_3$) δ 8.02 (d 1H), 7.82 (s, 1H), 7.49 (d, 1H), 7.33 (dd, 1H), 6.96 (s, 1H), 6.84 (s, 1H), 4.02-3.93 (m, 2H), 2.59 (s, 3H), 2.08-1.74 (m, 6H), 1.53-1.42 (m, 2H), 1.33-1.22 (m, 1H), 1.01-0.94 (m, 3H). MS $(M+H)^+$ 432.3. Enantiomeric ratio, 99.6:0.4. 6B Peak 2: $^1$H NMR (400 MHz, $CDCl_3$) δ 8.02 (d, 1H), 7.82 (s, 1H), 7.49 (d, 1H), 7.36-7.29 (m, 1H), 6.96 (s, 1H), 6.84 (s, 1H), 4.04-3.93 (m, 2H), 2.59 (s, 3H), 2.06-1.73 (m, 5H), 1.52-1.40 (m, 2H), 1.35-1.20 (m, 2H), 0.96 (t, 3H). MS $(M+H)^+$ 432.3. Enantiomeric ratio, 0.7:99.3.

Example 7

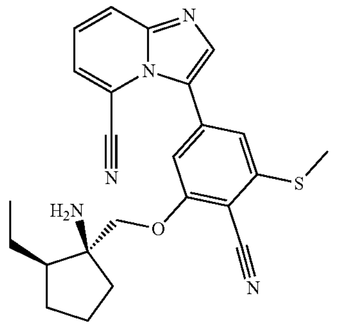

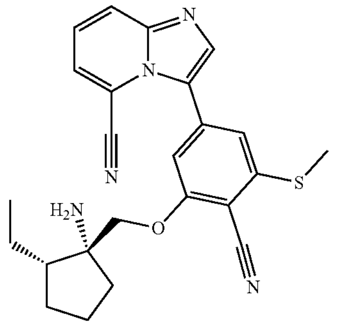

3-(3-(((1S,2R)-1-Amino-2-ethylcyclopentyl)methoxy)-4-cyano-5-(methylthio)phenyl)imidazo[1,2-a]pyridine-5-carbonitrile and 3-(3-(((1R,2S)-1-amino-2-ethylcyclopentyl)methoxy)-4-cyano-5-(methylthio)phenyl)imidazo[1,2-a]pyridine-5-carbonitrile (Racemate). Synthesized from 1-amino-2-ethylcyclopentane-1-carboxylic acid (Tetrahedron: Asymmetry 2000, 11, 3231-3252). $^1$H NMR (400 MHz, MeOD) δ 8.00 (dd, 1H), 7.88 (s, 1H), 7.72 (dd, 1H), 7.48 (dd, 1H), 7.21 (s, 1H), 7.20 (s, 1H), 4.10-4.05 (m, 2H), 2.61 (s, 3H), 2.09-1.92 (m, 2H), 1.88-1.71 (m, 3H), 1.70-1.60 (m, 2H), 1.54-1.42 (m, 1H), 1.34-1.20 (m, 1H), 1.02-0.93 (m, 3H). MS $(M+H)^+$ 432.3.

Example 8

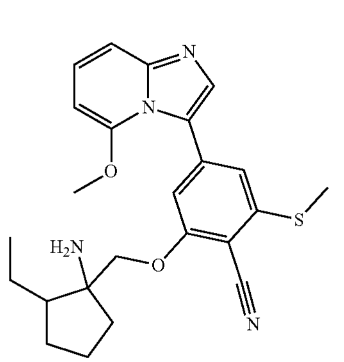 [SMILES: CCC1CCCC1(N)COc1cc(-c2cnc3cccc(OC)n23)cc(SC)c1C#N]

2-((1-Amino-2-ethylcyclopentyl)methoxy)-4-(5-methoxyimidazo[1,2-a]pyridin-3-yl)-6-(methylthio)benzonitrile (Racemic cis/trans mix). Synthesized from 1-amino-2-ethylcyclopentane-1-carboxylic acid (Tetrahedron: Asymmetry 2000, 11, 3231-3252). $^1$H NMR (400 MHz, MeOD) δ 7.66-7.63 (m, 1H), 7.47-7.40 (m, 1H), 7.29-7.24

(m, 1H), 7.08-7.01 (m, 2H), 6.46-6.39 (m, 1H), 4.07-3.99 (m, 2H), 3.96 (s, 3H), 2.59 (s, 3H), 2.12-1.94 (m, 2H), 1.83-1.62 (m, 5H), 1.54-1.40 (m, 1H), 1.23-1.10 (m, 1H), 1.00-0.92 (m, 3H). MS $(M+H)^+$ 437.3.

Example 9

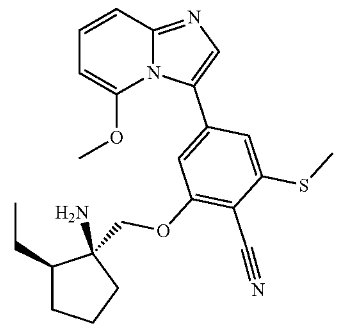

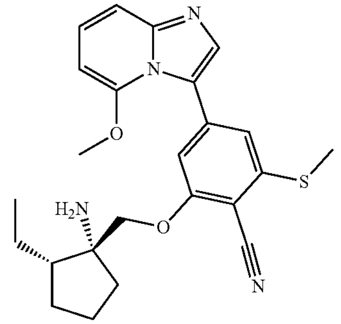

2-(((1S,2R)-1-Amino-2-ethylcyclopentyl)methoxy)-4-(5-methoxyimidazo[1,2-a]pyridin-3-yl)-6-(methylthio)benzonitrile and 2-(((1R,2S)-1-amino-2-ethylcyclopentyl)methoxy)-4-(5-methoxyimidazo[1,2-a]pyridin-3-yl)-6-(methylthio)benzonitrile (Racemate). Synthesized from 1-amino-2-ethylcyclopentane-1-carboxylic acid (Tetrahedron: Asymmetry 2000, 11, 3231-3252). $^1H$ NMR (400 MHz, MeOD) δ 7.64 (s, 1H), 7.44 (dd, 1H), 7.28 (d, 1H), 7.06 (s, 1H), 7.03 (s, 1H), 6.42 (d, 1H), 4.03 (s, 2H), 3.97 (s, 3H), 2.60 (s, 3H), 2.09-1.93 (m, 2H), 1.89-1.72 (m, 3H), 1.70-1.59 (m, 2H), 1.56-1.42 (m, 1H), 1.34-1.22 (m, 1H), 1.03-0.95 (m, 3H). MS $(M+H)^+$ 437.3.

Example 10

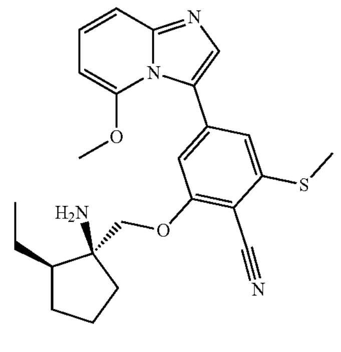

-continued

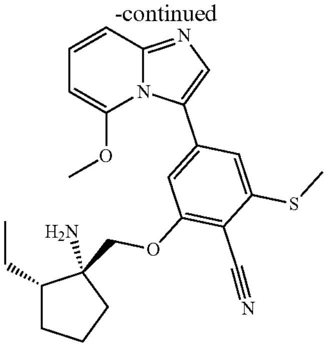

2-(((1S,2R)-1-Amino-2-ethylcyclopentyl)methoxy)-4-(5-methoxyimidazo[1,2-a]pyridin-3-yl)-6-(methylthio)benzonitrile and 2-(((1R,2S)-1-Amino-2-ethylcyclopentyl)methoxy)-4-(5-methoxyimidazo[1,2-a]pyridin-3-yl)-6-(methylthio)benzonitrile. Synthesized from 1-amino-2-ethylcyclopentane-1-carboxylic acid (Tetrahedron: Asymmetry 2000, 11, 3231-3252). Enantiomers (absolute stereochemistry not determined) were separated by chiral SFC: Chiral SFC: Phenomenex-Cellulose-2, 100 mm×4.6 mm, 3μ; A: $CO_2$, B: 0.05% Diethylamine/EtOH 60:40 A:B, 2.8 mL/min, 35° C.; retention times, 4.43 min (Peak 1), 6.27 min (Peak 2). 10A Peak 1: $^1H$ NMR (400 MHz, MeOD) δ 7.64 (s, 1H), 7.48-7.41 (m, 1H), 7.27 (d, 1H), 7.06 (s, 1H), 7.02 (s, 1H), 6.42 (d, 1H), 4.02 (s, 2H), 3.97 (s, 3H), 2.60 (s, 3H), 2.08-1.91 (m, 2H), 1.86-1.72 (m, 3H), 1.69-1.60 (m, 2H), 1.54-1.42 (m, 1H), 1.33-1.21 (m, 1H), 1.02-0.94 (m, 3H). MS (M+H)+437.4. Enantiomeric Ratio: 99.8:0.2. 10B Peak 2: $^1H$ NMR (400 MHz, MeOD) δ 7.64 (s, 1H), 7.44 (dd, 1H), 7.27 (d, 1H), 7.05 (s, 1H), 7.02 (s, 1H), 6.42 (d, 1H), 4.02 (s, 2H), 3.96 (s, 3H), 2.59 (s, 3H), 2.07-1.91 (m, 2H), 1.86-1.72 (m, 3H), 1.69-1.58 (m, 2H), 1.53-1.42 (m, 1H), 1.32-1.20 (m, 1H), 1.01-0.94 (m, 3H). MS $(M+H)^+$ 437.4. Enantiomeric Ratio: 0.3:99.7.

Example 11

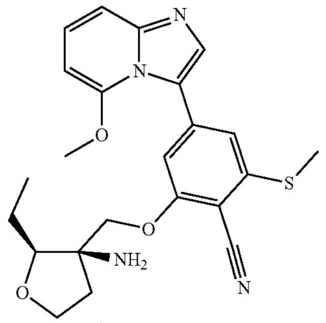

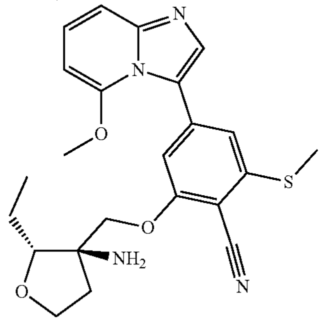

-continued

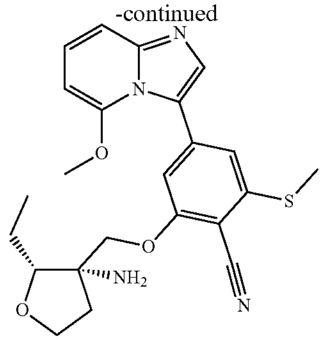

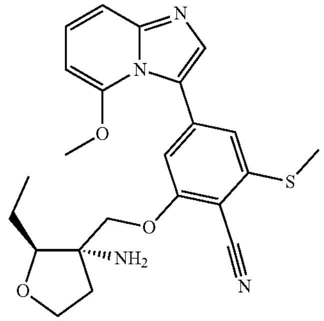

2-(((2S,3R)-3-Amino-2-ethyltetrahydrofuran-3-yl)methoxy)-4-(5-methoxyimidazo[1,2-a]pyridin-3-yl)-6-(methylthio)benzonitrile, 2-(((2R,3R)-3-Amino-2-ethyltetrahydrofuran-3-yl)methoxy)-4-(5-methoxyimidazo[1,2-a]pyridin-3-yl)-6-(methylthio)benzonitrile and 2-(((2R,3S)-3-Amino-2-ethyltetrahydrofuran-3-yl)methoxy)-4-(5-methoxyimidazo[1,2-a]pyridin-3-yl)-6-(methylthio)-benzonitrile and 2-(((25,35)-3-Amino-2-ethyltetrahydrofuran-3-yl)methoxy)-4-(5-methoxyimidazo[1,2-a]pyridin-3-yl)-6-(methylthio)benzonitrile.

Synthesized from propionaldehyde by analogy to Beilstein Journal of Organic Chemistry 2009, 5, No. 5. doi:10.3762/bjoc.5.5. Diastereomers and Enantiomers (absolute stereochemistry not determined) were separated by chiral SFC: Chiral SFC: Chiralpak IG-3, 50 mm×4.6 mm, 3μ; A: $CO_2$, B: 0.05% Diethylamine/MeOH, 60:40 A:B, 4 mL/min, 40° C.; retention times: 1.69 min (Peak 1), 2.05 min (Peak 2), 2.78 min (Peak 3), 3.84 min (Peak 4). 11A Peak 1: $^1H$ NMR (400 MHz, DMSO-$d_6$) δ 7.76 (s, 1H), 7.43-7.37 (m, 1H), 7.32-7.27 (m, 1H), 7.09 (s, 1H), 7.07 (s, 1H), 6.45 (d, 1H), 4.08 (s, 2H), 3.94 (s, 3H), 3.87 (q, 1H), 3.68-3.59 (m, 1H), 3.48 (dd, 1H), 2.61 (s, 3H), 2.14-2.04 (m, 1H), 1.79-1.70 (m, 1H), 1.68-1.56 (m, 2H), 1.54-1.40 (m, 1H), 0.94 (t, 3H). MS $(M+H)^+$ 439.4. Stereoisomeric Ratio: 99.47:0:0.15:0.39. 11B Peak 2: $^1H$ NMR (400 MHz, DMSO-$d_6$) δ 7.78 (s, 1H), 7.43-7.38 (m, 1H), 7.34-7.28 (m, 1H), 7.18 (s, 1H), 7.08 (s, 1H), 6.46 (d, 1H), 4.10-4.00 (m, 2H), 3.94 (s, 3H), 3.83-3.76 (m, 2H), 3.40-3.37 (m, 1H, partially obscured by residual solvent), 2.62 (s, 3H), 2.12-2.03 (m, 1H), 1.85-1.76 (m, 3H), 1.67-1.56 (m, 1H), 1.38-1.28 (m, 1H), 0.93 (t, 3H). MS $(M+H)^+$ 439.4. Stereoisomeric Ratio: 1.56:98.44:0:0. 11C Peak 3: $^1H$ NMR (400 MHz, DMSO-$d_6$) δ 7.77 (s, 1H), 7.43-7.37 (m, 1H), 7.32-7.27 (m, 1H), 7.10 (s, 1H), 7.08 (s, 1H), 6.46 (d, 1H), 4.09 (s, 2H), 3.94 (s, 3H), 3.91-3.84 (m, 1H), 3.68-3.60 (m, 1H), 3.48 (dd, 1H), 2.61 (s, 3H), 2.14-2.04 (m, 1H), 1.79-1.71 (m, 1H), 1.69-1.56 (m, 2H), 1.54-1.42 (m, 1H), 0.95 (t, 3H). MS $(M+H)^+$ 439.4. Stereoisomeric Ratio: 0.25:1.06:98.57:0.12. 11D Peak 4: $^1H$ NMR (400 MHz, DMSO-$d_6$) δ 7.78 (s, 1H), 7.43-7.37 (m, 1H), 7.33-7.27 (m, 1H), 7.18 (s, 1H), 7.07 (s, 1H), 6.46 (d, 1H), 4.10-4.00 (m, 2H), 3.94 (s, 3H), 3.83-3.75 (m, 2H), 3.37 (m, 1H, partially obscured by residual solvent), 2.62 (s, 3H), 2.11-2.01 (m, 1H), 1.86-1.75 (m, 3H), 1.67-1.56 (m, 1H), 1.38-1.27 (m, 1H), 0.93 (t, 3H). MS (M+H)+439.4. Stereoisomeric Ratio: 0.03:0.14:1.20:98.62.

Example 12

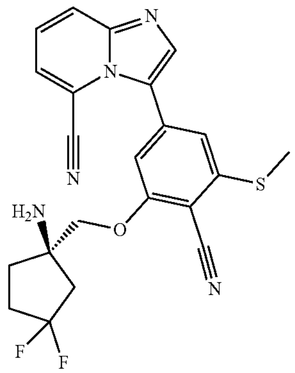

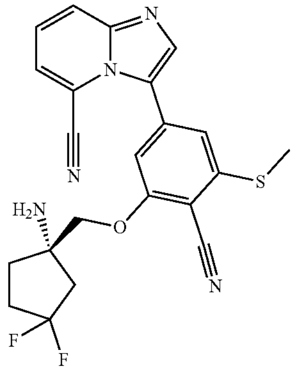

(R)-3-(3-((1-Amino-3,3-difluorocyclopentyl)methoxy)-4-cyano-5-(methylthio)phenyl)imidazo[1,2-a]pyridine-5-carbonitrile and (S)-3-(3-((1-amino-3,3-difluorocyclopentyl)methoxy)-4-cyano-5-(methylthio)phenyl)imidazo[1,2-a]pyridine-5-carbonitrile (Racemate). $^1H$ NMR (400 MHz, $CDCl_3$) δ 8.03 (d, 1H), 7.83 (s, 1H), 7.50 (d, 1H), 7.34 (dd, 1H), 7.00 (s, 1H), 6.84 (s, 1H), 4.02 (s, 2H), 2.6 (s, 3H), 2.5-2.3 (m, 2H), 2.3-2.2 (m, 2H), 2.2-2.1 (m, 1H), 1.9-1.8 (m, 3H). MS $(M+H)^+$ 440.1.

Example 13

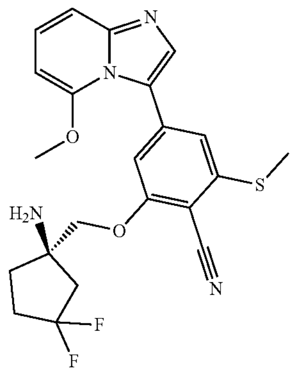

-continued

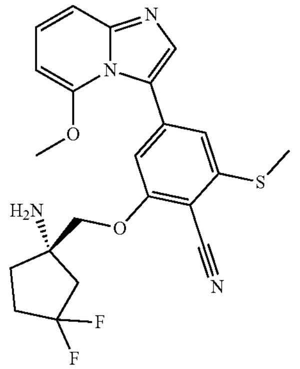

(R)-2-((1-Amino-3,3-difluorocyclopentyl)methoxy)-4-(5-methoxyimidazo[1,2-a]pyridin-3-yl)-6-(methylthio)benzonitrile and (S)-2-((1-Amino-3,3-difluorocyclopentyl)methoxy)-4-(5-methoxyimidazo[1,2-a]pyridin-3-yl)-6-(methylthio)benzonitrile. Enantiomers (absolute stereochemistry not determined) were separated by chiral SFC: Chiral SFC: Chiralpak IG-3, 50 mm×4.6 mm, 3μ; A: $CO_2$, B: 0.05% Diethylamine/MeOH 60:40 A:B, 4 mL/min, 35° C.; retention times, 1.13 min (Peak 1), 2.58 min (Peak 2). 13A Peak 1: $^1$H NMR (400 MHz, MeOD) δ 7.63 (s, 1H), 7.43 (dd, 1H), 7.29-7.24 (m, 1H), 7.08 (s, 1H), 7.03 (s, 1H), 6.41 (d, 1H), 4.04 (s, 2H), 3.95 (s, 3H), 2.59 (s, 3H), 2.52-2.35 (m, 2H), 2.33-2.19 (m, 1H), 2.18-2.07 (m, 2H), 1.90-1.80 (m, 1H). MS $(M+H)^+$ 445.2. Enantiomeric Ratio: 100:0. 13B Peak 2: $^1$H NMR (400 MHz, MeOD) δ 7.65 (s, 1H), 7.46 (dd, 1H), 7.28 (d, 1H), 7.13 (s, 1H), 7.07 (s, 1H), 6.44 (d, 1H), 4.17 (s, 2H), 3.96 (s, 3H), 2.61 (s, 3H), 2.46-2.23 (m, 5H), 2.06-1.97 (m, 1H). MS $(M+H)^+$ 445.3. Enantiomeric Ratio: 99.9:0.1.

Example 14

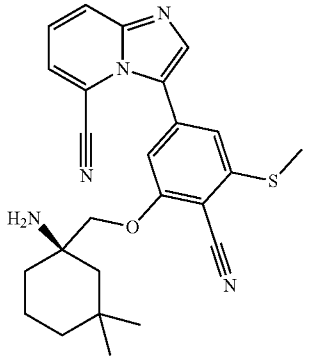

-continued

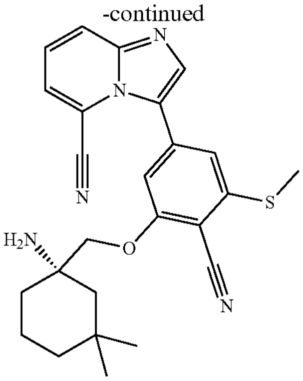

(R)-3-(3-((1-Amino-3,3-dimethylcyclohexyl)methoxy)-4-cyano-5-(methylthio)phenyl)imidazo[1,2-a]pyridine-5-carbonitrile and (S)-3-(3-((1-amino-3,3-dimethylcyclohexyl)methoxy)-4-cyano-5-(methylthio)phenyl)imidazo[1,2-a]pyridine-5-carbonitrile (Racemate). $^1$H NMR (400 MHz, DMSO-$d_6$) δ 8.12 (d, 1H), 7.98 (s, 1H), 7.88 (d, 1H), 7.50-7.43 (m, 1H), 7.30 (s, 1H), 7.25 (s, 1H), 3.89-3.78 (m, 2H), 2.62 (s, 3H), 1.85-1.73 (m, 1H), 1.47-1.21 (m, 7H), 1.12 (s, 3H), 0.86 (s, 3H). MS $(M+H)^+$ 446.3.

Example 15

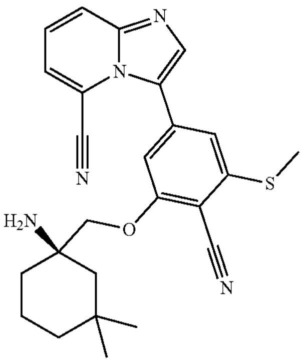

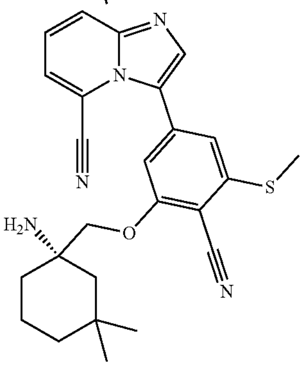

(R)-3-(3-((1-Amino-3,3-dimethylcyclohexyl)methoxy)-4-cyano-5-(methylthio)phenyl)imidazo[1,2-a]pyridine-5-carbonitrile and (S)-3-(3-((1-Amino-3,3-dimethylcyclohexyl)methoxy)-4-cyano-5-(methylthio)phenyl)imidazo[1,2-a]pyridine-5-carbonitrile. Enantiomers (absolute stereochemistry not determined) were separated by chiral SFC: Chiral SFC: Phenomenex-Cellulose-4, 100 mm×4.6 mm, 3μ; A: $CO_2$, B: 0.05% Diethylamine/EtOH 50:50 A:B, 2.8 mL/min, 40° C.; retention times, 1.65 min (Peak 1), 1.97 min (Peak 2). 15A Peak 1: $^{1}H$ NMR (400 MHz, MeOD) δ 8.01 (dd, 1H), 7.89 (s, 1H), 7.73 (dd, 1H), 7.49 (dd, 1H), 7.21 (s, 1H), 7.20 (s, 1H), 4.06-3.95 (m, 2H), 2.63 (s, 3H), 1.81-1.70 (m, 1H), 1.70-1.62 (m, 2H), 1.62-1.51 (m, 2H), 1.43-1.34 (m, 2H), 1.34-1.25 (m, 1H), 1.09 (s, 3H), 0.95 (s, 3H). MS $(M+H)^{+}$ 446.3. Enantiomeric Ratio: 100:0. 15B Peak 2: $^{1}H$ NMR (400 MHz, MeOD) δ 8.00 (dd, 1H), 7.88 (s, 1H), 7.74-7.69 (m, 1H), 7.48 (dd, 1H), 7.20 (s, 1H), 7.19 (s, 1H), 4.05-3.90 (m, 2H), 2.61 (s, 3H), 1.79-1.71 (m, 1H), 1.69-1.60 (m, 2H), 1.60-1.50 (m, 2H), 1.42-1.33 (m, 2H), 1.32-1.24 (m, 1H), 1.08 (s, 3H), 0.94 (s, 3H). MS $(M+H)^{+}$ 446.3. Enantiomeric Ratio: 0:100.

Example 16

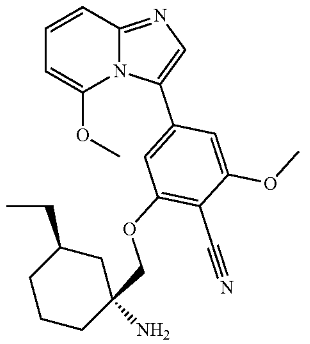

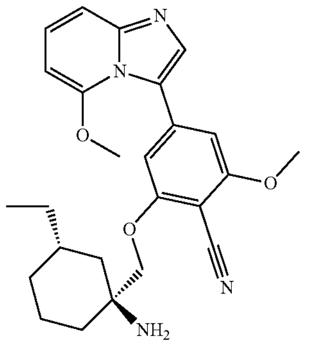

2-(((1R,3R)-1-Amino-3-ethylcyclohexyl)methoxy)-6-methoxy-4-(5-methoxyimidazo[1,2-a]pyridin-3-yl)benzonitrile and 2-(((16,36)-1-Amino-3-ethylcyclohexyl)methoxy)-6-methoxy-4-(5-methoxyimidazo[1,2-a]pyridin-3-yl) benzonitrile (Racemate). Synthesized starting from 3-ethylcyclohexan-1-one by procedures analogous to Tetrahedron 2015, 71, 2409-2420. $^{1}H$ NMR (400 MHz, MeOD) δ 7.61 (s, 1H), 7.42 (dd, 1H), 7.25 (dd, 1H), 6.83 (s, 1H), 6.82 (s, 1H), 6.40 (d, 1H), 3.96 (s, 3H), 3.95 (s, 3H), 3.87 (s, 2H), 1.87-1.62 (m, 4H), 1.62-1.41 (m, 3H), 1.27 (m, 2H), 1.13 (t, 1H), 0.92 (t, 3H), 0.86 (m, 1H). MS $(M+H)^{+}$ 435.5.

Example 17

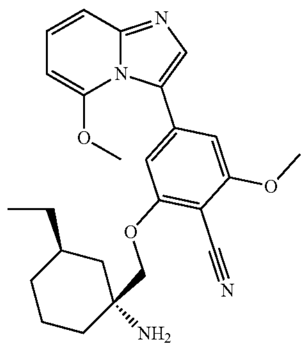

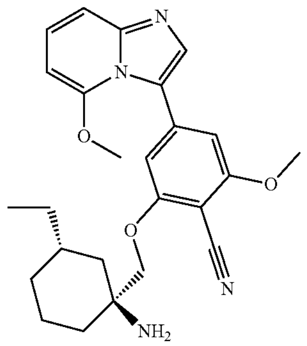

2-(((1R,3R)-1-Amino-3-ethylcyclohexyl)methoxy)-6-methoxy-4-(5-methoxyimidazo[1,2-a]pyridin-3-yl)benzonitrile and 2-(((16,36)-1-Amino-3-ethylcyclohexyl)methoxy)-6-methoxy-4-(5-methoxyimidazo[1,2-a]pyridin-3-yl) benzonitrile. Synthesized starting from 3-ethylcyclohexan-1-one by procedures analogous to Tetrahedron 2015, 71, 2409-2420. Enantiomers (absolute stereochemistry not determined) were separated by chiral HPLC: Chiral HPLC: ChiralPak IG, 50 mm×4.6 mm, 3μ; A: 0.1% diethylamine/hexane, B: 0.05% diethylamine/ethanol, 60:40 A:B, 1 mL/min, 35° C.; retention times, 5.0 min (Peak 1), 6.2 min (Peak 2). 17A Peak 1: $^{1}H$ NMR (400 MHz, MeOD) δ 7.62 (s, 1H), 7.43 (dd, 1H), 7.26 (dd, 1H), 6.84 (s, 1H), 6.82 (s, 1H), 6.40 (d, 1H), 3.96 (s, 3H), 3.95 (s, 3H), 3.87 (s, 2H), 1.89-1.42 (m, 7H), 1.33-1.19 (m, 3H), 1.14 (t, 1H), 0.93 (t, 3H), 0.88 (m, 1H). MS $(M+H)^{+}$ 435.3. Enantiomeric ratio, 98.8:1.2. 17B Peak 2: $^{1}H$ NMR (400 MHz, MeOD) δ 7.62 (s, 1H), 7.43 (dd, 1H), 7.26 (dd, 1H), 6.84 (s, 1H), 6.82 (s, 1H), 6.41 (d, 1H), 3.96 (s, 3H), 3.95 (s, 3H), 3.87 (s, 2H), 1.90-1.42 (m, 7H), 1.33-1.20 (m, 2H), 1.14 (t, 1H), 0.93 (t, 3H), 0.89 (m, 1H). MS $(M+H)^{+}$ 435.3. Enantiomeric ratio, 0.4:99.6.

Example 18

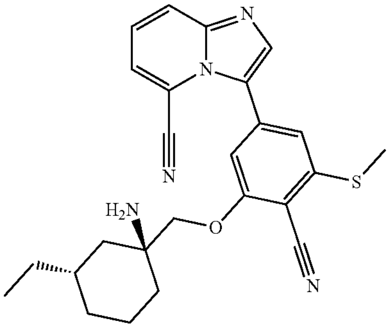

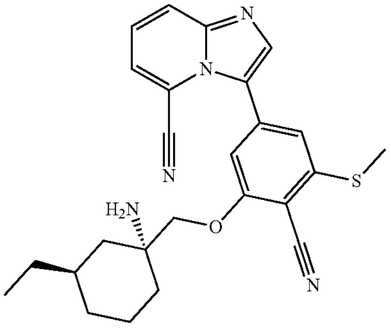

3-(3-(((1S,3S)-1-Amino-3-ethylcyclohexyl)methoxy)-4-cyano-5-(methylthio)phenyl)imidazo[1,2-a]pyridine-5-carbonitrile and 3-(3-(((1R,3R)-1-amino-3-ethylcyclohexyl)methoxy)-4-cyano-5-(methylthio)phenyl)imidazo[1,2-a]pyridine-5-carbonitrile (Racemate). Synthesized starting from 3-ethylcyclohexan-1-one by procedures analogous to Tetrahedron 2015, 71, 2409-2420. $^1$H NMR (400 MHz, MeOD) δ 8.02-7.97 (m, 1H), 7.88 (s, 1H), 7.72 (d, 1H), 7.48 (dd, 1H), 7.20 (s, 1H), 7.18 (s, 1H), 3.93 (s, 2H), 2.62 (s, 3H), 1.86-1.78 (m, 1H), 1.77-1.63 (m, 4H), 1.62-1.43 (m, 2H), 1.34-1.21 (m, 2H), 1.18-1.08 (m, 1H), 0.93 (t, 3H), 0.90-0.78 (m, 1H). MS $(M+H)^+$ 446.3.

Example 19

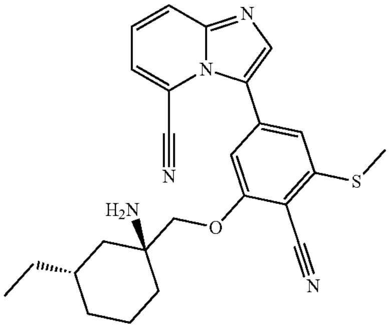

-continued

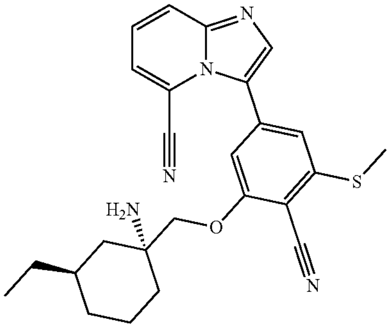

3-(3-(((1S,3S)-1-Amino-3-ethylcyclohexyl)methoxy)-4-cyano-5-(methylthio)phenyl)imidazo[1,2-a]pyridine-5-carbonitrile and 3-(3-(((1R,3R)-1-Amino-3-ethylcyclohexyl)methoxy)-4-cyano-5-(methylthio)-phenyl)imidazo[1,2-a]pyridine-5-carbonitrile. Synthesized starting from 3-ethylcyclohexan-1-one by procedures analogous to Tetrahedron 2015, 71, 2409-2420. Enantiomers (absolute stereochemistry not determined) were separated by chiral SFC: Chiral SFC: Chiralpak IG-3, 150 mm×4.6 mm, 3μ; A: $CO_2$, B: 0.05% Diethylamine/iPrOH, Gradient: from 5% to 40% B in 4 min and hold for 2 min. 2.5 mL/min, 35° C.; retention times, 4.98 min (Peak 1), 5.28 min (Peak 2). 19A Peak 1: $^1$H NMR (400 MHz, MeOD) δ 8.00 (dd, 1H), 7.89 (s, 1H), 7.73 (dd, 1H), 7.49 (dd, 1H), 7.21 (s, 1H), 7.18 (s, 1H), 3.93 (s, 2H), 2.62 (s, 3H), 1.87-1.78 (m, 1H), 1.78-1.64 (m, 4H), 1.62-1.42 (m, 2H), 1.33-1.22 (m, 2H), 1.17-1.09 (m, 1H), 0.93 (t, 3H), 0.90-0.80 (m, 1H). MS $(M+H)^+$ 446.3. Enantiomeric Ratio: 99.1:0.90. 19B Peak 2: $^1$H NMR (400 MHz, MeOD) δ 8.00 (dd, 1H), 7.89 (s, 1H), 7.75-7.70 (m, 1H), 7.49 (dd, 1H), 7.20 (s, 1H), 7.18 (s, 1H), 3.93 (s, 2H), 2.62 (s, 3H), 1.87-1.78 (m, 1H), 1.78-1.64 (m, 4H), 1.61-1.44 (m, 2H), 1.34-1.21 (m, 2H), 1.19-1.08 (m, 1H), 0.93 (t, 3H), 0.90-0.79 (m, 1H). MS $(M+H)^+$ 446.3. Enantiomeric Ratio 1.65:98.35.

Example 20

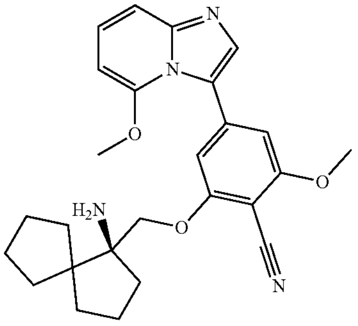

-continued

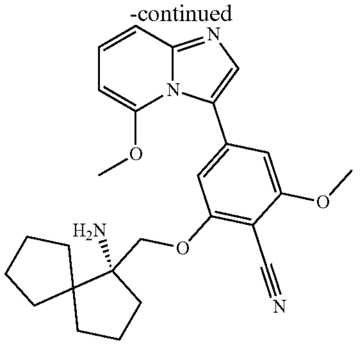

(S)-2-((1-Aminospiro[4.4]nonan-1-yl)methoxy)-6-methoxy-4-(5-methoxyimidazo[1,2-a]pyridin-3-yl)benzonitrile and (R)-2-((1-Aminospiro[4.4]nonan-1-yl)methoxy)-6-methoxy-4-(5-methoxyimidazo[1,2-a]pyridin-3-yl)benzonitrile. Enantiomers (absolute stereochemistry not determined) were separated by chiral SFC: Chiral SFC: Phenomenex-Cellulose-2, 150 mm×4.6 mm, 5μ; A: $CO_2$, B: 0.05% Diethylamine/EtOH 40:60 A:B, 2.5 mL/min, 35° C.; retention times, 2.86 min (Peak 1), 4.42 min (Peak 2). 20A Peak 1: $^1$H NMR (400 MHz, MeOD) δ 7.63 (s, 1H), 7.43 (dd, 1H), 7.26 (d, 1H), 6.85 (s, 1H), 6.85 (s, 1H), 6.41 (d, 1H), 4.21-4.02 (m, 2H), 3.96 (s, 3H), 3.96 (s, 3H), 2.12-2.00 (m, 1H), 1.98-1.89 (m, 1H), 1.85-1.75 (m, 2H), 1.74-1.59 (m, 8H), 1.54-1.44 (m, 1H), 1.41-1.32 (m, 1H). MS $(M+H)^+$ 447.3. Enantiomeric Ratio: 99.35:0.65. 20B Peak 2: $^1$H NMR (400 MHz, MeOD) δ 7.63 (s, 1H), 7.45-7.40 (m, 1H), 7.25 (d, 1H), 6.85 (s, 1H), 6.84 (s, 1H), 6.40 (d, 1H), 4.18-4.03 (m, 2H), 3.96 (s, 3H), 3.96 (s, 3H), 2.09-2.00 (m, 1H), 1.97-1.89 (m, 1H), 1.87-1.77 (m, 2H), 1.74-1.59 (m, 8H), 1.52-1.44 (m, 1H), 1.39-1.31 (m, 1H). MS $(M+H)^+$ 447.4. Enantiomeric Ratio: 0.5:99.5.

Example 21

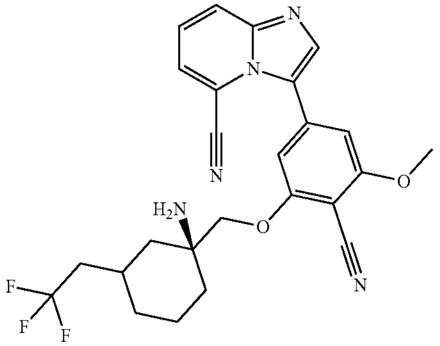

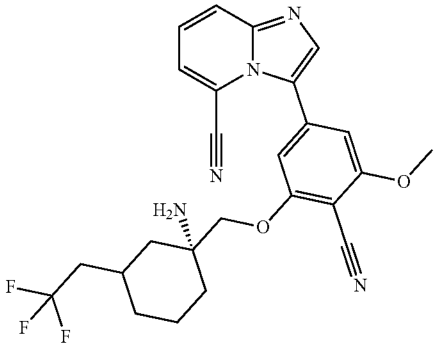

(S)-2-((3-Amino-1-(2,2,2-trifluoroethyl)piperidin-3-yl)methoxy)-6-methoxy-4-(5-methoxyimidazo[1,2-a]pyridin-3-yl)benzonitrile and (R)-2-((3-Amino-1-(2,2,2-trifluoroethyl)piperidin-3-yl)methoxy)-6-methoxy-4-(5-methoxyimidazo[1,2-a]pyridin-3-yl)benzonitrile. Synthesized from (3-amino-1-(2,2,2-trifluoroethyl)piperidin-3-yl)methanol. Enantiomers (absolute stereochemistry not determined) were separated by chiral SFC: Chiral SFC: Chiralpak IG-3, 100 mm×4.6 mm, 3μ; A: $CO_2$, B: 0.05% Diethylamine/EtOH, 60:40 A:B, 2.5 mL/min, 40° C.; retention times, 2.03 min (Peak 1), 2.70 min (Peak 2). 21A Peak 1: $^1$H NMR (400 MHz, DMSO-$d_6$) δ 7.74 (s, 1H), 7.43-7.36 (m, 1H), 7.32-7.27 (m, 1H), 6.90 (s, 1H), 6.89 (s, 1H), 6.45 (d, 1H), 4.16-4.09 (m, 1H), 3.95-3.89 (m, 7H), 3.22-3.10 (m, 2H), 2.75 (d, 1H), 2.61-2.54 (m, 2H), 2.40 (d, 1H), 1.70-1.50 (m, 3H), 1.39-1.28 (m, 1H). MS $(M+H)^+$ 490.4. Enantiomeric Ratio 100:0. 21B Peak 2: $^1$H NMR (400 MHz, DMSO-$d_6$) δ 7.74 (s, 1H), 7.39 (dd, 1H), 7.31-7.27 (m, 1H), 6.90 (s, 1H), 6.89 (s, 1H), 6.45 (d, 1H), 4.15-4.09 (m, 1H), 3.95-3.90 (m, 7H), 3.20-3.11 (m, 2H), 2.75 (d, 1H), 2.60-2.54 (m, 2H), 2.40 (d, 1H), 1.69-1.50 (m, 3H), 1.38-1.28 (m, 1H). MS $(M+H)^+$ 490.4. Enantiomeric Ratio 0.6:99.4.

Example 22

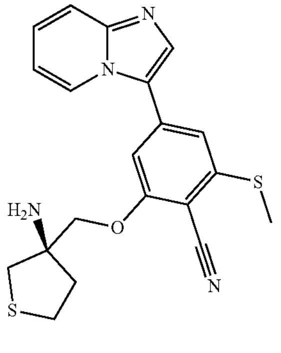

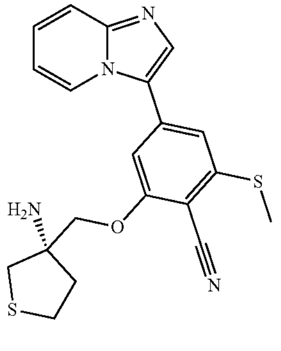

(R)-2-((3-Aminotetrahydrothiophen-3-yl)methoxy)-4-(imidazo[1,2-a]pyridin-3-yl)-6-(methylthio)benzonitrile and (S)-2-((3-Aminotetrahydrothiophen-3-yl)methoxy)-4-(imidazo[1,2-a]pyridin-3-yl)-6-(methylthio)benzonitrile (Racemate). $^1$H NMR (400 MHz, MeOD) δ 8.67 (d, 1H), 7.90 (s, 1H), 7.67 (d, 1H), 7.44 (dd, 1H), 7.27-7.20 (m, 2H), 7.07 (dd, 1H), 4.33 (app q, 2H), 3.05-2.82 (m, 4H), 2.65 (s, 3H), 2.22-2.12 (m, 2H). MS $(M+H)^+$ 397.2.

Example 23

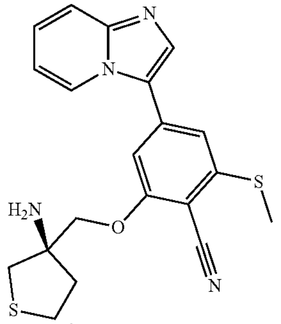

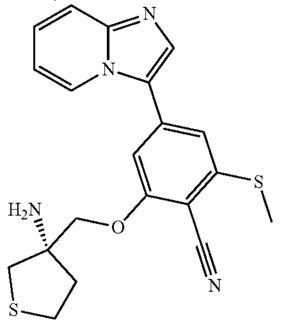

(R)-2-((3-Aminotetrahydrothiophen-3-yl)methoxy)-4-(imidazo[1,2-a]pyridin-3-yl)-6-(methylthio)benzonitrile and (S)-2-((3-Aminotetrahydrothiophen-3-yl)methoxy)-4-(imidazo[1,2-a]pyridin-3-yl)-6-(methylthio)benzonitrile. Enantiomers (absolute stereochemistry not determined) were separated by chiral HPLC: Chiral HPLC: ChiralPak IE, 100 mm×4.6 mm, 3μ; A: 0.1% diethylamine/hexane, B: 0.1% diethylamine/ethanol, 20:80 A:B, 1 mL/min, 35° C.; retention times, 5.9 min (Peak 1), 7.0 min (Peak 2). 23A Peak 1: $^1$H NMR (400 MHz, MeOD) δ 8.66 (d, 1H), 7.89 (s, 1H), 7.66 (d, 1H), 7.44 (dd, 1H), 7.24-7.19 (m, 2H), 7.07 (dd, 1H), 4.32-4.19 (m, 2H), 3.12-3.01 (m, 2H), 2.99-2.89 (m, 1H), 2.75 (d, 1H), 2.65 (s, 3H), 2.20-2.00 (m, 2H). MS $(M+H)^+$ 397.4. Enantiomeric ratio, 100:0. 23B Peak 2: 1H NMR (400 MHz, MeOD) δ 8.67 (d, 1H), 7.89 (s, 1H), 7.67 (d, 1H), 7.44 (m, 1H), 7.25-7.19 (m, 2H), 7.07 (m, 1H), 4.33-4.19 (m, 2H), 3.11-3.02 (m, 2H), 2.99-2.90 (m, 1H), 2.76 (d, 1H), 2.65 (s, 3H), 2.19-2.02 (m, 2H). MS $(M+H)^+$ 397.2. Enantiomeric ratio, 0.4:99.6.

Example 24

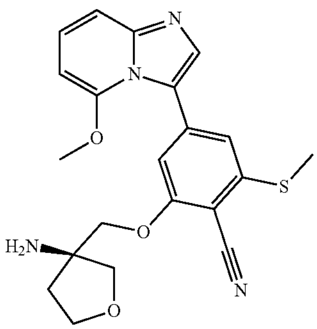

-continued

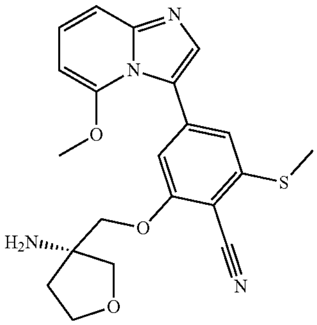

(R)-2-((3-Aminotetrahydrofuran-3-yl)methoxy)-4-(5-methoxyimidazo[1,2-a]pyridin-3-yl)-6-(methylthio)benzonitrile and (S)-2-((3-Aminotetrahydrofuran-3-yl)methoxy)-4-(5-methoxyimidazo[1,2-a]pyridin-3-yl)-6-(methylthio)benzonitrile. Enantiomers (absolute stereochemistry not determined) were separated by chiral SFC: Chiral SFC: Lux Amylose 1, 4.6 mm×100 mm, 5μ; A: 0.2% $NH_4OH$/MeOH, B: $CO_2$, 40:60 A:B, 1.5 mL/min, 120 Bar, room temperature; retention times, 2.47 min (Peak 1), 2.57 min (Peak 2). 24A Peak 1: MS $(M+Na)^+$ 433.3. 24B Peak 2: MS $(M+Na)^+$ 433.3.

Example 25

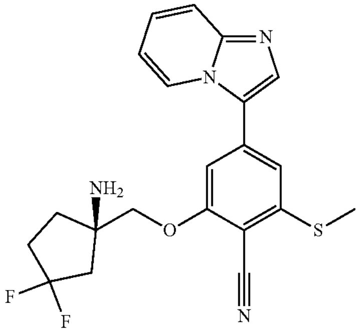

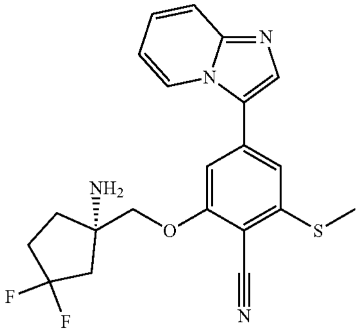

(R)-2-((1-Amino-3,3-difluorocyclopentyl)methoxy)-4-(imidazo[1,2-a]pyridin-3-yl)-6-(methylthio)benzonitrile and (S)-2-((1-amino-3,3-difluorocyclopentyl)methoxy)-4-(imidazo[1,2-a]pyridin-3-yl)-6-(methylthio)benzonitrile (Racemate). The compound was purified by preparative HPLC. MS $(M+H)^+$ 415.4.

Example 26

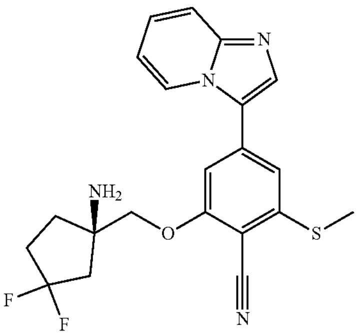

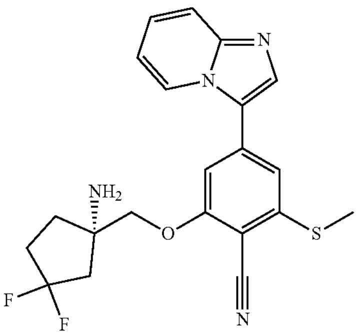

(R)-2-((1-amino-3,3-difluorocyclopentyl)methoxy)-4-(imidazo[1,2-a]pyridin-3-yl)-6-(methylthio)benzonitrile and (S)-2-((1-amino-3,3-difluorocyclopentyl)methoxy)-4-(imidazo[1,2-a]pyridin-3-yl)-6-(methylthio)benzonitrile. Enantiomers (absolute stereochemistry not determined) were separated by chiral SFC: Chiral SFC: Chiralpak IG-3, 4.6 mm×50 mm, 3μ; A: $CO_2$, B: 0.05% diethylamine/MeOH, 60:40 A:B, 4 mL/min, 1500 psi, 35° C.; retention times, 1.82 min (Peak 1), 2.49 min (Peak 2). 26B Peak 1: MS $(M+H)^+$ 415.2. Enantiomeric ratio, 100:0. 26A Peak 2: MS $(M+H)^+$ 415.2. Enantiomeric ratio, 0.4:99.6.

Example 27

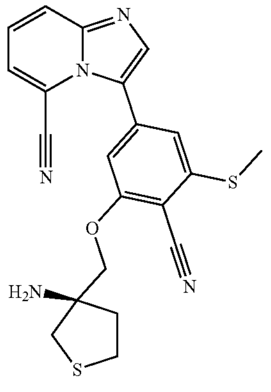

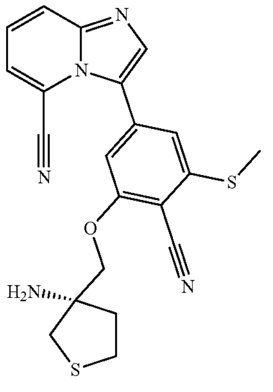

(R)-3-(3-((3-aminotetrahydrothiophen-3-yl)methoxy)-4-cyano-5-(methylthio)phenyl)imidazo[1,2-a]pyridine-5-carbonitrile and (6)-3-(3-(((3-aminotetrahydrothiophen-3-yl) methoxy)-4-cyano-5-(methylthio)phenyl)imidazo[1,2-a] pyridine-5-carbonitrile (Racemate). The compound was purified by preparative HPLC. MS $(M+H)^+$ 422.2.

Example 28

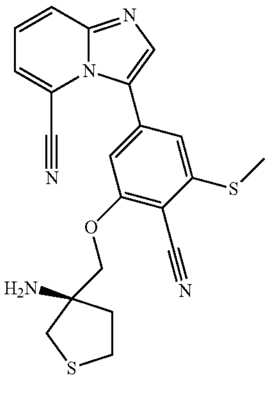

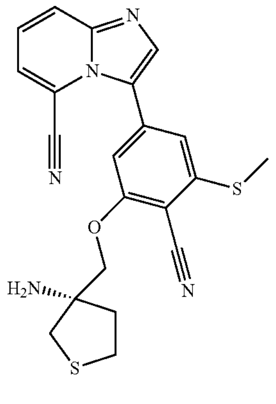

(R)-3-(3-((3-aminotetrahydrothiophen-3-yl)methoxy)-4-cyano-5-(methylthio)phenyl)imidazo[1,2-a]pyridine-5-carbonitrile and (S)-3-(3-((3-aminotetrahydrothiophen-3-yl) methoxy)-4-cyano-5-(methylthio)phenyl)imidazo[1,2-a] pyridine-5-carbonitrile. The enantiomers (absolute stereochemistry not determined) of intermediate tert-butyl (R)-(3-((2-cyano-5-(5-cyanoimidazo[1,2-a]pyridin-3-yl)-3-(methylthio)phenoxy)methyl)tetrahydrothiophen-3-yl)carbamate and tert-butyl (S)-(3-((2-cyano-5-(5-cyanoimidazo [1,2-a]pyridin-3-yl)-3-(methylthio)phenoxy)methyl) tetrahydrothiophen-3-yl)carbamate were separated by chiral SFC. Chiral SFC: Chiral Tech AD-H 250 mm×30.0 mm, 5μ; A: $CO_2$; B: EtOH (0.2% 7N $NH_3$ in MeOH). Gradient: 95% A: 5% B 0.5 min, then linear to 20% A and 80% B at 5.5 min and hold; 3 mL/min. Intermediate Enantiomer 1, retention time, 4.7 min; Intermediate Enantiomer 2, 4.9 min. The separated individual intermediate enantiomers were then independently converted to (R)-3-(3-((3-aminotetrahydrothiophen-3-yl)methoxy)-4-cyano-5-(methylthio)phenyl) imidazo[1,2-a]pyridine-5-carbonitrile and (S)-3-(34(3-aminotetrahydrothiophen-3-yl)methoxy)-4-cyano-5-(methylthio)phenyl)imid-azo[1,2-a]pyridine-5-carbonitrile (absolute stereochemistry not determined). HPLC: Atlantis dC18 4.6×50 mm 5μ; A: 0.05% TFA in $H_2O$, B: 0.05% TFA in $CH_3CN$; 95:5 A:B to 5:95 A:B over 4 min; 2 mL/min. 28A Enantiomer 1 (derived from Intermediate Enantiomer 1), retention time, 1.88 min. MS $(M+H)^+$ 422.2. 28B Enantiomer 2 (derived from Intermediate Enantiomer 2), retention time, 1.87 min; MS $(M+H)^+$ 422.2.

Example 29

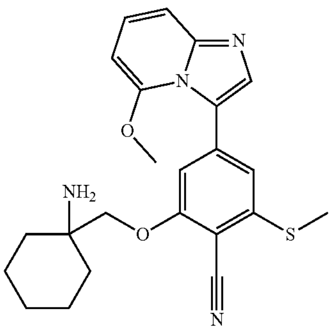 [SMILES: COc1cccc2ncc(-c3cc(OCC4(N)CCCCC4)c(C#N)c(SC)c3)n12]

2-((1-Aminocyclohexyl)methoxy)-4-(5-methoxyimidazo[1,2-a]pyridin-3-yl)-6 (methylthio)benzonitrile. $^1$H NMR (400 MHz, $CDCl_3$) δ 7.59 (s, 1H), 7.38-7.25 (m, 2H), 6.91 (s, 1H), 6.77 (d, 1H), 6.13 (d, 1H), 3.90 (s, 3H), 3.85 (s, 2H), 2.55 (s, 3H), 1.68-1.47 (m, 10H). MS $(M+H)^+$ 423.5.

Example 30

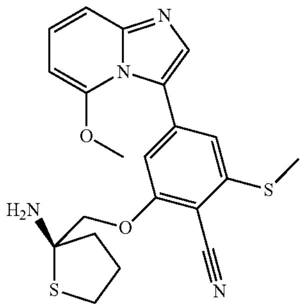

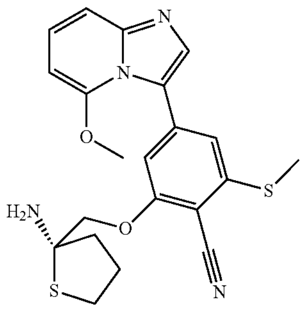

(R)-2-((3-aminotetrahydrothiophen-3-yl)methoxy)-4-(5-methoxyimidazo[1,2-a]pyridin-3-yl)-6-(methylthio)benzonitrile and (S)-2-((3-aminotetrahydrothiophen-3-yl)methoxy)-4-(5-methoxyimidazo[1,2-a]pyridin-3-yl)-6-(methylthio)benzonitrile. Enantiomers (absolute stereochemistry not determined; separated by chiral chromato-graphy): Chiral SFC: ChiralTech OX-H 100 mm×4.6 mm, 3μ; A: $CO_2$, B: MeOH+0.2% TFA; 5:95 A:B to 30:70 A:B over 2.5 min, then hold. 30A Peak 1: retention time, 2.47 min; MS $(M+H)^+$ 427.3. 30B Peak 2, retention time, 2.63 min; MS $(M+H)^+$ 427.3.

Example 31

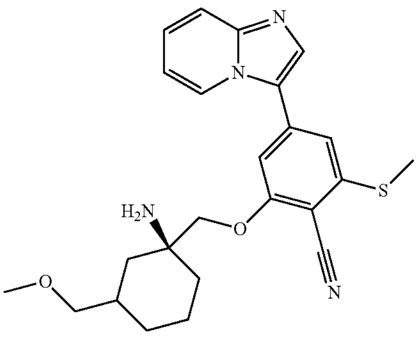

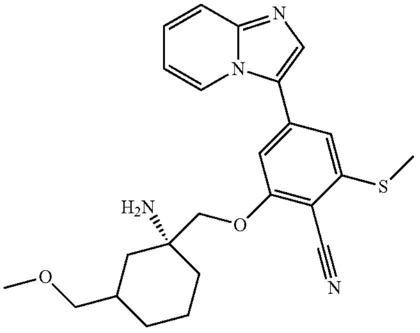

2-(((1S)-1-Amino-3-(methoxymethyl)cyclohexyl)methoxy)-4-(imidazo[1,2-a]pyridin-3-yl)-6-(methylthio)benzonitrile and 2-(((1R)-1-amino-3-(methoxymethyl)-cyclohexyl)methoxy)-4-(imidazo[1,2-a]pyridin-3-yl)-6-(methylthio)benzonitrile (Mixture of diastereomers). $^1$H NMR (400 MHz, MeOD) δ 8.66 (d, 1H), 7.89 (s, 1H), 7.67 (d, 1H), 7.45 (m, 1H), 7.21 (d, 1H), 7.17 (d, 1H), 7.08 (m, 1H), 3.96 (s, 2H), 3.33 (s, 3H), 3.30-3.20 (m, 2H), 2.65 (s, 3H), 2.10-1.96 (m, 1H), 1.86-1.67 (m, 5H), 1.58-1.46 (m, 1H), 1.25 (t, 1H), 1.05-0.90 (m, 1H). MS $(M+H)^+$ 437.2.

Example 32

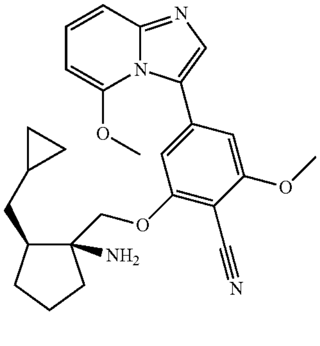

-continued

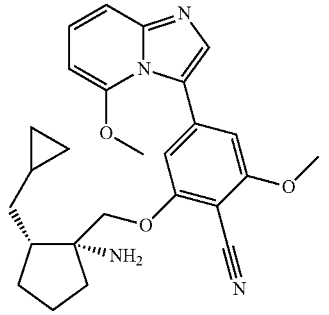

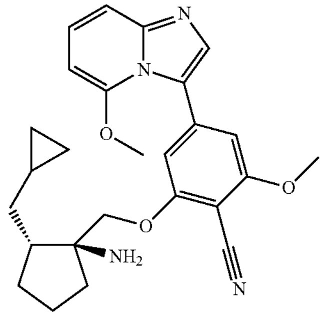

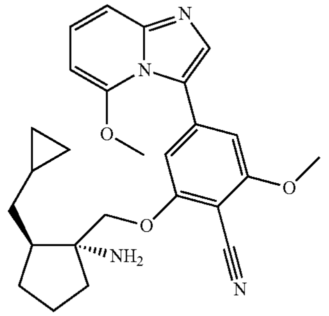

2-(((1S,2S)-1-Amino-2-(cyclopropylmethyl)cyclopentyl)methoxy)-6-methoxy-4-(5-methoxyimidazo[1,2-a]pyridin-3-yl)benzonitrile and 2-(((1R,2R)-1-amino-2-(cyclopropylmethyl)cyclopentyl)methoxy)-6-methoxy-4-(5-methoxyimidazo[1,2-a]pyridin-3-yl)benzonitrile (cis enantiomers); 2-(((1S,2R)-1-amino-2-(cyclopropylmethyl)cyclopentyl)methoxy)-6-methoxy-4-(5-methoxyimidazo[1,2-a]pyridin-3-yl)benzonitrile and 2-(((1R,2S)-1-amino-2-(cyclopropylmethyl)cyclopentyl)methoxy)-6-methoxy-4-(5-methoxyimidazo[1,2-a]pyridin-3-yl)benzonitrile (trans enantiomers). Stereoisomers (absolute stereochemistry not determined) were separated by chiral SFC. Chiral SFC: Chiralpak IC-3, 4.6 mm×100 mm, 3μ; A: $CO_2$, B: 0.05% $iPr_2NEt$/EtOH, 50:50 A:B, 2.8 mL/min, 1500 psi, 35° C.; retention times, 3.72 min (Peak 1), 4.55 min (Peak 2), 5.62 min (Peak 3), 6.01 min (Peak 4). 32A Peak 1 (cis): $^1H$ NMR (400 MHz, MeOD) δ 7.63 (s, 1H), 7.44 (dd, 1H), 7.27 (dd, 1H), 6.85 (app s, 2H), 6.42 (d, 1H), 4.02 (s, 2H), 3.97 (s, 3H), 3.97 (s, 3H), 2.18-1.75 (m, 4H), 1.71-1.53 (m, 3H), 1.51-1.40 (m, 1H), 1.39-1.26 (m, 1H), 0.80-0.64 (m, 1H), 0.52-0.32 (m, 2H), 0.17-0.08 (m, 1H), 0.00 (m, 1H). MS $(M+H)^+$ 447.4. Stereoisomeric ratio, 100:0:0:0. 32B Peak 2 (trans): $^1H$ NMR (400 MHz, MeOD) δ 7.64 (s, 1H), 7.45 (dd, 1H), 7.28 (d, 1H), 6.87 (app s, 2H), 6.43 (d, 1H), 4.07-3.99 (m, 2H), 3.97 (app s, 6H), 2.25-2.11 (m, 1H), 2.07-1.96 (m, 2H), 1.86-1.69 (m, 2H), 1.67-1.55 (m, 1H), 1.50-1.41 (m, 1H), 1.32-1.19 (m, 1H), 0.96-0.83 (m, 1H), 0.79-0.67 (m, 1H), 0.52-0.37 (m, 2H), 0.17-0.01 (m, 2H). MS $(M+H)^+$ 447.3. Stereoisomeric ratio, 5.0:95.0:0:0. 32C Peak 3 (cis): $^1H$ NMR (400 MHz, MeOD) δ 7.63 (s, 1H), 7.44 (dd, 1H), 7.27 (dd, 1H), 6.85 (s, 1H), 6.85 (s, 1H), 6.42 (d, 1H), 4.02 (s, 2H), 3.97 (s, 3H), 3.97 (s, 3H), 2.17-2.08 (m, 1H), 2.06-1.98 (m, 1H), 1.98-1.91 (m, 1H), 1.89-1.76 (m, 1H), 1.70-1.53 (m, 3H), 1.51-1.41 (m, 1H), 1.39-1.27 (m, 1H), 0.79-0.67 (m, 1H), 0.51-0.35 (m, 2H), 0.17-0.09 (m, 1H), 0.0 (m, 1H). MS $(M+H)^+$ 447.3. Stereoisomeric ratio, 0:0:100:0. 32D Peak 4 (trans): $^1H$ NMR (400 MHz, MeOD) δ 7.65 (s, 1H), 7.45 (dd, 1H), 7.31-7.24 (m, 1H), 6.89 (app s, 2H), 6.43 (d, 1H), 4.11-4.03 (m, 2H), 3.97 (app s, 6H), 2.26-2.15 (m, 1H), 2.11-2.01 (m, 2H), 1.86-1.72 (m, 2H), 1.69-1.55 (m, 1H), 1.51-1.42 (m, 1H), 1.39-1.22 (m, 1H), 0.97-0.87 (m, 1H), 0.79-0.68 (m, 1H), 0.54-0.38 (m, 2H), 0.16-0.00 (m, 2H). MS $(M+H)^+$ 447.3. Stereoisomeric ratio, 0:0:0.9:99.1.

Example 33

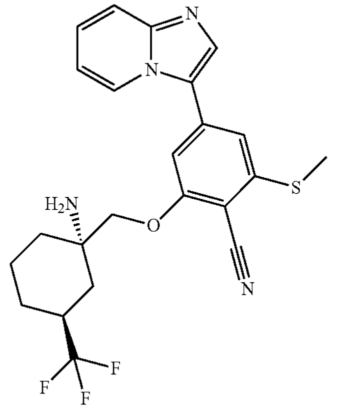

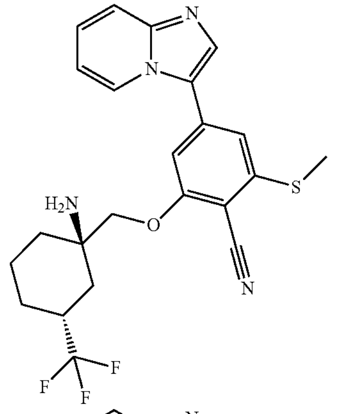

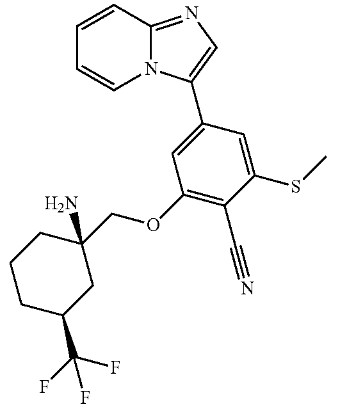

-continued

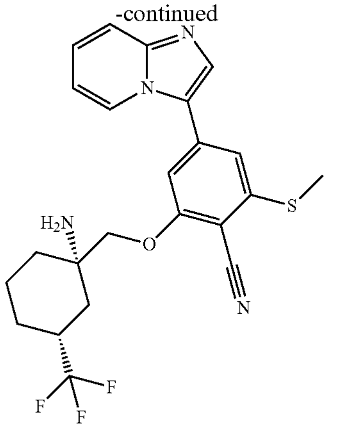

2-(((1S,3S)-1-Amino-3-(trifluoromethyl)cyclohexyl) methoxy)-4-(imidazo[1,2-a]pyridin-3-yl)-6-(methylthio) benzonitrile and 2-(((1R,3R)-1-amino-3-(trifluoromethyl) cyclohexyl)methoxy)-4-(imidazo[1,2-a]pyridin-3-yl)-6-(methylthio)benzonitrile (racemic trans); and 2-(((1R,3S)-1-Amino-3-(trifluoromethyl)cyclohexyl)methoxy)-4-(imidazo [1,2-a]pyridin-3-yl)-6-(methylthio)benzonitrile and 2-(((1S, 3R)-1-amino-3-(trifluoromethyl)cyclohexyl)methoxy)-4-(imidazo[1,2-a]pyridin-3-yl)-6-(methylthio)benzonitrile (racemic cis). Diastereomers were separated by HPLC. 33A Racemic trans: $^1$H NMR (400 MHz, DMSO-$d_6$) δ 8.79-8.70 (m, 1H), 8.01 (s, 1H), 7.71-7.64 (m, 1H), 7.38 (m, 1H), 7.22 (d, 1H), 7.20 (d, 1H), 7.03 (m, 1H), 3.98 (s, 2H), 2.66 (s, 3H), 1.89-1.68 (m, 3H), 1.65-1.38 (m, 5H), 1.21-1.07 (m, 1H). MS $(M+H)^+$ 461.3. 33B Racemate (cis): $^1$H NMR (400 MHz, DMSO-$d_6$) δ 8.81-8.69 (m, 1H), 8.01 (s, 1H), 7.72 (d, 1H), 7.38 (m, 1H), 7.31 (d, 1H), 7.20 (d, 1H), 7.05 (m, 1H), 4.15 (s, 2H), 2.66 (s, 3H), 2.06-1.98 (m, 1H), 1.89-1.62 (m, 4H), 1.54-1.38 (m, 1H), 1.32-1.09 (m, 3H). MS $(M+H)^+$ 461.3

Preparation E

3-Iodopyrazolo[1,5-a]pyridine-4-carbonitrile. N-Iodosuccinimide (443 mg, 1.97 mmol) was added to a solution of pyrazolo[1,5-a]pyridine-4-carbonitrile (282 mg, 1.97 mmol) in MeCN (10 mL). The resulting mixture was stirred for 2 h, then the solids were collected by filtration to afford 3-iodopyrazolo[1,5-a]pyridine-4-carbonitrile (530 mg). $^1$H NMR (400 MHz, DMSO) δ 9.10 (dd, 1H), 8.33 (s, 1H), 8.04 (dd, 1H), 7.08 (t, 1H). MS $(M+H)^+$ 269.9.

Preparation F

3-Iodoimidazo[1,2-a]pyridine-5-carbonitrile. NIS (1184 g, 5.26 mol) was added to a solution of imidazo[1,2-a] pyridine-5-carbonitrile (579.5 g, 4.05 mol) in DMF (5.795 L), then the reaction vessel was purged with 2 cycles of vacuum and $N_2$ gas. The mixture was heated at 65-75° C. for 0.5 h, then was cooled to 15-20° C. and an aqueous solution of $Na_2SO_3$ (10.3 wt %, 5.795 L) was added. After stirring for 0.5 h, the solids were collected by filtration, rinsing with $H_2O$. The collected solids were dissolved in dioxane (11.59 L) at 60-70° C., then the resulting solution was cooled to 20-25° C., $H_2O$ (11.59 L) was added, and the mixture was stirred for an additional 0.5 h. The solids were collected and dried to afford 3-iodoimidazo[1,2-a]pyridine-5-carbonitrile (932 g). $^1$H NMR (400 MHz, DMSO-$d_6$) δ 8.01 (dd, 1H), 7.89 (s, 1H), 7.86 (dd, 1H), 7.36 (dd, 1H). MS $(M+H)^+$ 269.9

Preparation G 2-((1-Aminocyclohexyl)methoxy)-4-bromo-6-(methylthio)benzonitrile. A solution of KHMDS in THF (1M, 754 mL, 754 mmol) was added dropwise to a solution of 4-bromo-2-fluoro-6-(methylthio)-benzonitrile (186 g, 754 mmol) and (1-aminocyclohexyl)methanol (104 g, 754 mmol) in THF (1.856 L) at 10° C. under an atmosphere of $N_2$. The resulting mixture was stirred at 25° C. for 9 h, then was added to an aqueous solution of 25% $NH_4Cl$. The mixture was extracted with EtOAc and the organic layer was concentrated. The residue was purified by silica gel chromatography (10:1 DCM:MeOH) to afford 2-((1-aminocyclohexyl)methoxy)-4-bromo-6-(methylthio)benzonitrile (165 g). $^1$H NMR (400 MHz, $CDCl_3$) δ 6.98 (s, 1H), 6.95 (s, 1H), 3.95 (s, 2H), 2.56 (s, 3H), 1.72-1.39 (m, 10H). MS $(M+H)^+$ 357.0

Preparation H tert-Butyl (1-((5-bromo-2-cyano-3-(methylthio)phenoxy) methyl)cyclohexyl)-carbamate. $Boc_2O$ (94.6 g, 433 mmol) was added to a solution of 2-((1-aminocyclo-hexyl) methoxy)-4-bromo-6-(methylthio)benzonitrile (140 g, 394 mmol) in THF (1.68 L) and EtOH (0.28 L) at 15° C. The mixture was stirred for 40 h, then was concentrated. The residue was concentrated from EtOAc (2×), then was treated with EtOAc (0.70 L) and was stirred at 20° C. for 1 h. The resulting solids were collected, rinsing with EtOAc, and were combined with the solids from another reaction that was run under analogous conditions (from 280 g 2-((1-aminocyclohexyl)methoxy)-4-bromo-6-(methylthio)benzonitrile and 189 g $Boc_2O$). The combined solids were dried to afford tert-butyl (1-((5-bromo-2-cyano-3-(methylthio)phenoxy)methyl)cyclohexyl)carbamate as a solid (493 g). $^1$H NMR (400 MHz, DMSO-$d_6$) δ 7.27 (s, 1H), 7.13 (s, 1H), 6.44 (br s, 1H), 4.22 (s, 2H), 2.59 (s, 3H), 2.02 (m, 2H), 1.44 (m, 7H), 1.34 (s, 9H), 1.21 (m, 1H). MS $(M+H)^+$ 457.2

Preparation I tert-Butyl (1-((2-cyano-3-(methylthio)-5-(4,4,5,5-tetramethyl-1,3,2-dioxaborolan-2-yl)phenoxy)methyl)cyclohexyl) carbamate. $PdCl_2$(dppf)-DCM (17.9 g, 22.0 mmol) was added to a mixture of tert-butyl (1-((5-bromo-2-cyano-3-(methylthio)phenoxy)methyl)-cyclohexyl)carbamate (200 g, 439 mmol), $B_2(pin)_2$ (134 g, 527 mmol) and KOAc (129 g, 1.32 mol) in dioxane (2.20 L) at 20° C. The reaction mixture was purged with $N_2$, then was stirred at 100° C. for 18 h. The mixture was concentrated, then was suspended in MeTHF-DCM (3.0 L each). The mixture was filtered through Celite™, and the filtrate was washed with water. The organic layer was concentrated and the residue was suspended in heptane (1.0 L) and the resulting mixture was stirred at 20° C. for 1 h. The solids were collected by filtration, rinsing with heptane, then were purified by silica gel chromatography (10:1-3:1 heptane:EtOAc) to afford tert-butyl (1-((2-cyano-3-(methylthio)-5-(4,4,5,5-tetramethyl-1,3,2-dioxaborolan-2-yl)phenoxy)methyl)cyclohexyl)-carbamate (166 g). $^1$H NMR (400 MHz, DMSO-$d_6$) δ 7.13 (s, 1H), 7.09 (s, 1H), 6.42 (br s, 1H), 4.22 (s, 2H), 2.58 (s, 3H), 2.09-1.97 (m, 2H), 1.62-1.39 (m, 7H), 1.32 (s, 9H), 1.31 (s, 12H), 1.26-1.10 (m, 1H). MS $(M+H)^+$ 503.2.

Preparation J tert-Butyl (1-((2-cyano-5-(5-cyanoimidazo[1,2-a]pyridin-3-yl)-3-(methylthio)phenoxy)methyl)cyclohexyl)carbamate. Dioxane (23.35 mL) and $H_2O$ (7.75 mL) were added to a solid mixture of 3-iodoimidazo[1,2-a]pyridine-5-carbonitrile (2.50 g, 9.29 mmol), tert-butyl (1-((2-cyano-3-(methylthio)-5-(4,4,5,5-tetramethyl-1,3,2-dioxaborolan-2-yl)phenoxy)methyl)cyclohexyl)carbamate (4.90 g, 9.76 mmol), and $K_3PO_4$ (5.92 g, 27.9 mmol). The reaction vessel was purged with 4 cycles of vacuum and $N_2$ gas, then $Pd(PPh_3)_2Cl_2$ (65 mg, 0.093 mmol) was added. The reaction vessel was purged with 3 cycles of vacuum and $N_2$ gas and then was heated in a block at 95° C. for 17 h, then was cooled to ambient temperature. The mixture was diluted with MeTHF (24 mL) and $H_2O$ (7 mL), then N-acetylcysteine (758 mg, 4.65 mmol) was added, and the resulting mixture was stirred vigorously at 65° C. for 1 h. The layers were separated, and the aqueous layer was further extracted with MeTHF (2×12 mL). The combined organics were washed with 75% saturated aqueous brine solution (12 mL), then were dried over $Na_2SO_4$, filtered through Celite™, and concentrated. The resulting solid was suspended in 1-chlorobutane (69 mL) and the mixture was heated at 65° C. for 4 h, then was cooled to ambient temperature and stirred for 18 h. The solids were collected and dried to afford tert-butyl (1-((2-cyano-5-(5-cyanoimidazo[1,2-a]pyridin-3-yl)-3-(methylthio)phenoxy)methyl)cyclohexyl)carbamate as a pale yellow solid (4.83 g), contaminated with 1-chlorobutane and pinacol, which was used in the next step without further purification. $^1H$ NMR (400 MHz, DMSO-$d_6$) δ 8.12 (d, 1H), 7.99 (s, 1H), 7.89 (d, 1H), 7.47 (dd, 1H), 7.33 (s, 1H), 7.27 (s, 1H), 6.49 (br s, 1H), 4.26 (s, 2H), 2.63 (s, 3H), 2.06 (m, 2H), 1.58-1.43 (m, 7H), 1.30 (s, 9H), 1.24 (m, 1H). MS $(M+H)^+$ 518.3.

Example 34

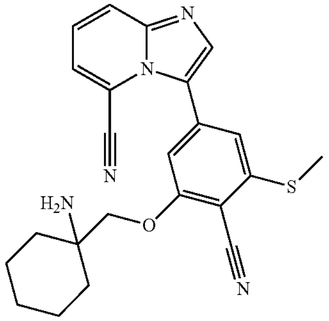 [SMILES: CSc1cc(-c2cnc3cccc(C#N)n23)cc(OCC2(N)CCCCC2)c1C#N]

3-(3-((1-Aminocyclohexyl)methoxy)-4-cyano-5-(methylthio)phenyl)imidazo[1,2-a]pyridine-5-carbonitrile. HCl solution (4M in dioxane, 21.0 mL, 84.4 mmol) was added over a period of 5 min to a solution of tert-butyl (1-((2-cyano-5-(5-cyanoimidazo[1,2-a]pyridin-3-yl)-3-(methylthio)phenoxy)methyl)cyclohexyl)carbamate (4.82 g, 8.44 mmol) in MeOH (42.2 mL) at 0° C. The mixture was warmed to ambient temperature and was stirred for 16 h. The mixture was concentrated, and the resulting solid was suspended in 10% 2-butanol-DCM (25 mL), then $H_2O$ (20 mL) was added. Concentrated aqueous ammonium hydroxide solution (2 mL) was added and the biphasic mixture was stirred for 20 min. The layers were separated, and the aqueous layer was extracted with 10% 2-butanol-DCM (2×10 mL). The combined organics were dried over $Na_2SO_4$, filtered, and concentrated. The resulting solid was suspended in 10% $H_2O$-EtOH and the mixture was heated at 60° C. for 3 h, then was stirred at ambient temperature for 19 h. The solids were collected by filtration and were dried to afford 3-(3-((1-aminocyclohexyl)methoxy)-4-cyano-5-(methylthio)phenyl)imidazo[1,2-a]pyridine-5-carbonitrile as a white solid (3.07 g). $^1H$ NMR (400 MHz, DMSO-$d_6$) δ 8.11 (d, 1H), 7.98 (s, 1H), 7.88 (d, 1H), 7.46 (dd, 1H), 7.33 (s, 1H), 7.25 (s, 1H), 3.92 (s, 2H), 2.62 (s, 3H), 1.70-1.32 (m, 9H), 1.29-1.17 (m, 1H). MS $(M+H)^+$ 418.1.

The following examples were synthesized by analogous methods and starting materials as described for 3-(3-((1-aminocyclohexyl)methoxy)-4-cyano-5-(methylthio)phenyl) imid-azo[1,2-a]pyridine-5-carbonitrile.

Example 35

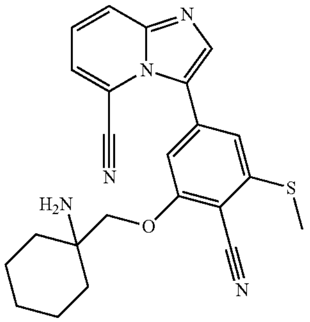 [SMILES: CSc1cc(-c2cnc3cccc(C#N)n23)cc(OCC2(N)CCCCC2)c1C#N]

3-(3-((1-Aminocyclohexyl)methoxy)-4-cyano-5-(methylthio)phenyl)pyrazolo[1,5-a]pyridine-4-carbonitrile. $^1H$ NMR (400 MHz, MeOD) δ 8.93 (dd, 1H), 8.37 (s, 1H), 7.91-7.97 (m, 1H), 7.15 (app d, 2H), 7.10 (t, 1H), 4.11 (s, 2H), 2.65 (s, 3H), 1.45-1.80 (m, 10H). MS $(M+H)^+$ 418.4.

Example 36

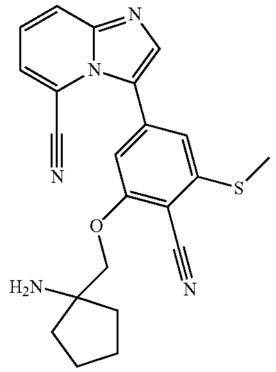 [SMILES: CSc1cc(-c2cnc3cccc(C#N)n23)cc(OCC2(N)CCCC2)c1C#N]

3-(3-((1-Aminocyclopentyl)methoxy)-4-cyano-5-(methylthio)phenyl)imidazo[1,2-a]pyridine-5-carbonitrile. $^1H$ NMR (400 MHz, DMSO-$d_6$) δ 8.11 (d, 1H), 7.98 (s, 1H), 7.88 (d, 1H), 7.46 (dd, 1H), 7.32 (s, 1H), 7.26 (s, 1H), 4.01 (s, 2H), 2.62 (s, 3H), 1.81-1.54 (m, 6H), 1.45 (t, 2H). MS $(M+H)^+$ 404.2.

Example 37

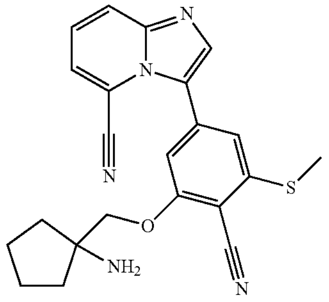 [SMILES: CSc1cc(-c2cnc3cccc(C#N)n23)cc(OCC2(N)CCCC2)c1C#N]

3-(3-((1-Aminocyclopentyl)methoxy)-4-cyano-5-(methylthio)phenyl)pyrazolo[1,5-a]pyridine-4-carbonitrile. $^1$H NMR (400 MHz, MeOD) δ 8.93 (d, 1H), 8.36 (s, 1H), 7.93 (d, 1H), 7.19-7.03 (m, 3H), 4.11 (s, 2H), 2.65 (s, 3H), 1.92-1.83 (m, 5H), 1.79-1.70 (m, 2H), 1.64 (m, 2H). MS $(M+H)^+$ 404.3.

Example 38

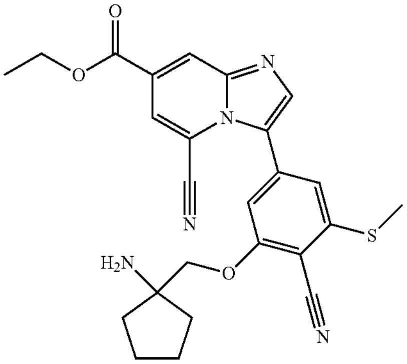 [SMILES: CCOC(=O)c1cc(C#N)n2c(-c3cc(OCC4(N)CCCC4)c(C#N)c(SC)c3)cnc2c1]

Ethyl 3-(3-((1-aminocyclopentyl)methoxy)-4-cyano-5-(methylthio)phenyl)-5-cyanoimidazo[1,2-a]pyridine-7-carboxylate. Synthesized from ethyl 5-cyanoimidazo[1,2-a]pyridine-7-carboxylate which was prepared from 7-bromoimidazo[1,2-a]pyridine-5-carbonitrile via Pd-catalyzed carbonylation. $^1$H NMR (400 MHz, MeOD) δ 8.58 (d, 1H), 8.16 (d, 1H), 8.06 (s, 1H), 7.25 (s, 1H), 7.24 (s, 1H), 4.47 (q, 2H), 4.08 (s, 2H), 2.63 (s, 3H), 1.93-1.81 (m, 4H), 1.77-1.69 (m, 2H), 1.69-1.60 (m, 2H), 1.44 (t, 3H). MS $(M+H)^+$ 476.3.

Preparation K tert-Butyl (E)-(1-((2-cyano-5-(2-ethoxyvinyl)-3-(methylthio)phenoxy)methyl)-cyclopentyl)carbamate. tert-Butyl (1-((5-bromo-2-cyano-3-(methylthio)phenoxy)- methyl)cyclopentyl)carbamate was synthesized by procedures analogous to tert-butyl (1-((5-bromo-2-cyano-3-(methylthio)phenoxy)methyl)-cyclo-hexyl)carbamate. To a solution of tert-butyl (1-((5-bromo-2-cyano-3-(methylthio)phenoxy)methyl)cyclopentyl)carbamate (4.4 g, 8.0 mmol) and (E)-2-(2-ethoxyvinyl)-4,4,5,5-tetramethyl-1,3,2-dioxaborolane (1.9 g, 9.57 mmol) in dioxane (50 mL) and water (5 mL) was added $K_3PO_4$ (5.08 g, 23.9 mmol) and $Pd(dppf)Cl_2$-DCM. The reaction was stirred under an atmosphere of $N_2$ at 90° C. for 2. The reaction was cooled to room temperature and partitioned between EtOAc (150 mL) and $H_2O$ (20 mL). The organic phase was dried over anhydrous $Na_2SO_4$, filtered, and concentrated. The residue was purified via silica gel chromatography (0-12% EtOAc/PE) to afford tert-butyl (E)-(1-((2-cyano-5-(2-ethoxyvinyl)-3-(methylthio)phenoxy)methyl)cyclopentyl)carbamate (3.1 g). $^1$H NMR (400 MHz, DMSO-$d_6$) δ 7.57 (d, 1H), 6.89 (s, 1H), 6.84 (s, 1H), 6.80 (br s, 1H), 5.86 (d, 1H), 4.20 (s, 2H), 3.94 (q, 2H), 2.54 (s, 3H), 1.97-1.86 (m, 2H), 1.77-1.57 (m, 6H), 1.34 (s, 9H), 1.26 (t, 3H). MS $(M+H\text{-}Boc)^+$ 333.3.

Example 39

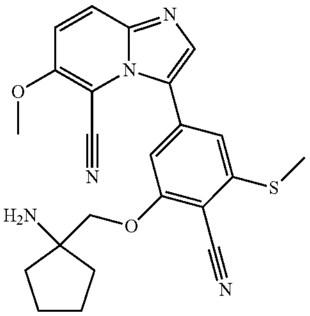 [SMILES: COc1ccc2ncc(-c3cc(OCC4(N)CCCC4)c(C#N)c(SC)c3)n2c1C#N]

3-(3-((1-Aminocyclopentyl)methoxy)-4-cyano-5-(methylthio)phenyl)-6-methoxyimidazo[1,2-a]pyridine-5-carbonitrile. To a solution of tert-butyl (E)-(1-((2-cyano-5-(2-ethoxyvinyl)-3-(methylthio)phenoxy)methyl)cyclopentyl)carbamate (100 mg, 0.231 mmol) in dioxane (2.0 mL) and $H_2O$ (1.0 mL) at 15° C. was added NBS (45.3 mg, 0.254 mmol). The mixture was stirred at 15° C. for 50 min. To this was added 6-amino-3-methoxy-2-pyridinecarbonitrile (34.5 mg, 0.231 mmol) and the reaction was stirred at 100° C. for 16 h. The reaction was concentrated and purified via preparative HPLC (affording 12 mg). HPLC: Boston Prime C18, 150 mm×30 mm, 5μ; A: $H_2O$ (0.2% $NH_4OH$), B: $CH_3CN$, Gradient: 19%-59% B over 9 min, then 100% B; 25 mL/min. $^1$H NMR (400 MHz, DMSO-$d_6$) δ 8.12 (d, 1H), 7.91 (s, 1H), 7.60 (d, 1H), 7.24 (s, 1H), 7.19 (s, 1H), 4.05 (s, 3H), 4.00 (s, 2H), 2.61 (s, 3H), 1.79-1.71 (m, 2H), 1.71-1.56 (m, 4H), 1.50-1.40 (m, 2H). MS $(M+H)^+$ 434.3.

The following examples were synthesized by analogous methods and starting materials as described for 3-(3-((1-aminocyclopentyl)methoxy)-4-cyano-5-(methylthio)phenyl)-6-methoxyimidazo[1,2-a]pyridine-5-carbonitrile.

Example 40

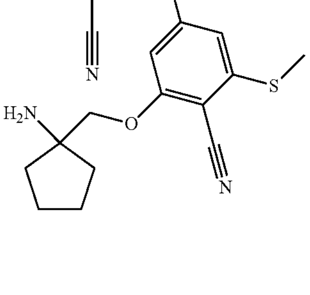

3-(3-((1-Aminocyclopentyl)methoxy)-4-cyano-5-(methylthio)phenyl)-6-methylimidazo[1,2-a]pyridine-5-carbonitrile. $^1H$ NMR (400 MHz, DMSO-$d_6$) δ 8.02 (d, 1H), 7.91 (s, 1H), 7.44 (d, 1H), 7.29 (s, 1H), 7.22 (s, 1H), 4.00 (s, 2H), 2.62 (s, 3H), 2.54 (s, 3H), 1.8-1.7 (m, 2H), 1.7-1.6 (m, 6H), 1.5-1.4 (m, 2H). MS $(M+H)^+$ 418.4.

Example 41

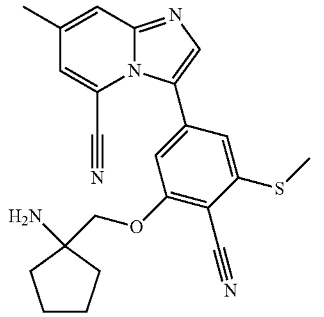

3-(3-((1-Aminocyclopentyl)methoxy)-4-cyano-5-(methylthio)phenyl)-7-methylimidazo[1,2-a]pyridine-5-carbonitrile. $^1H$ NMR (400 MHz, DMSO-$d_6$) δ 7.90 (br s, 1H), 7.89 (br s, 1H), 7.80 (s, 1H), 7.29 (s, 1H), 7.23 (s, 1H), 4.01 (s, 2H), 2.62 (s, 3H), 2.43 (s, 3H), 1.8-1.5 (m, 8H), 1.5-1.4 (m, 2H). MS $(M+H)^+$ 418.4.

Example 42

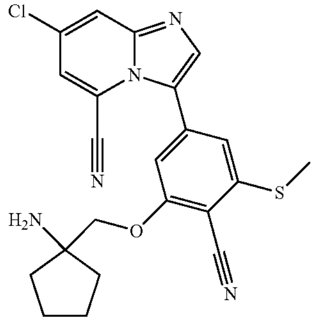 [SMILES: CSc1cc(-c2cnc3cc(Cl)cc(C#N)n23)cc(OCC2(N)CCCC2)c1C#N]

3-(3-((1-Aminocyclopentyl)methoxy)-4-cyano-5-(methylthio)phenyl)-7-chloroimidazo[1,2-a]pyridine-5-carbonitrile. $^1H$ NMR (400 MHz, MeOD) δ 8.07 (d, 1H), 7.89 (s, 1H), 7.84 (d, 1H), 7.21 (s, 1H), 7.21 (s, 1H), 4.06 (s, 2H), 2.61 (s, 3H), 1.92-1.81 (m, 4H), 1.77-1.68 (m, 2H), 1.68-1.59 (m, 2H). MS $(M+H)^+$ 438.1.

Example 44

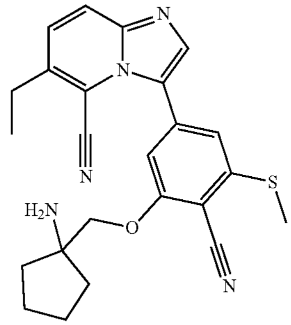 [SMILES: CCc1ccc2ncc(-c3cc(OCC4(N)CCCC4)c(C#N)c(SC)c3)n2c1C#N]

3-(3-((1-Aminocyclopentyl)methoxy)-4-cyano-5-(methylthio)phenyl)-6-ethylimidazo[1,2-a]pyridine-5-carbonitrile. Synthesized from 6-amino-3-bromopicolinonitrile and triethylborane by analogy to 6-amino-3-methylpicolinonitrile (WO2018071794). $^1H$ NMR (400 MHz, $CDCl_3$) δ 7.91 (d, 1H), 7.74 (s, 1H), 7.24 (d, 1H), 6.95 (d, 1H), 6.84 (d, 1H), 4.00 (s, 2H), 2.96-2.85 (m, 2H), 2.58 (s, 3H), 2.01-1.74 (m, 4H), 1.74-1.61 (m, 4H), 1.34 (t, 3H). MS $(M+H)^+$ 432.3.

Example 45

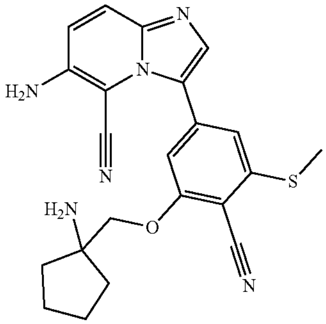 [SMILES: CSc1cc(-c2cnc3ccc(N)c(C#N)n23)cc(OCC2(N)CCCC2)c1C#N]

6-Amino-3-(3-((1-aminocyclopentyl)methoxy)-4-cyano-5-(methylthio)phenyl)imidazo[1,2-a]pyridine-5-carbonitrile. $^1H$ NMR (400 MHz, DMSO-$d_6$) δ 7.75 (d, 1H), 7.66 (s, 1H), 7.17 (s, 1H), 7.11 (s, 1H), 7.01 (d, 1H), 6.54 (s, 2H), 4.02 (s, 2H), 2.63 (s, 3H). MS $(M+H)^+$ 419.1.

Example 46

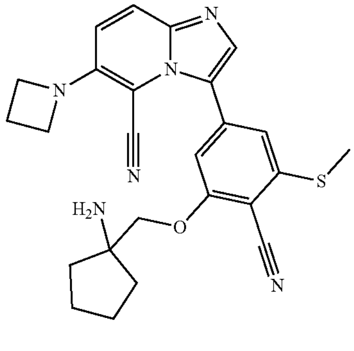 [SMILES: CSc1cc(-c2cnc3ccc(N4CCC4)c(C#N)n23)cc(OCC2(N)CCCC2)c1C#N]

3-(3-((1-Aminocyclopentyl)methoxy)-4-cyano-5-(methylthio)phenyl)-6-(azetidin-1-yl)imidazo[1,2-a]pyridine-5-carbonitrile. $^1$H NMR (500 MHz, MeOD) δ 7.68 (d, 1H), 7.64 (s, 1H), 7.12 (s, 1H), 7.09 (s, 1H), 6.92 (d, 1H), 4.31 (t, 4H), 4.06 (s, 2H), 2.63 (s, 3H), 2.46 (quin, 2H), 1.82-1.90 (m, 4H), 1.70-1.78 (m, 2H), 1.63 (br dd, 2H). MS (M+H)$^+$ 459.3.

Example 47

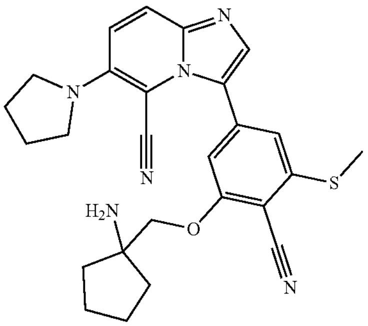 [SMILES: CSc1cc(-c2cnc3ccc(N4CCCC4)c(C#N)n23)cc(OCC2(N)CCCC2)c1C#N]

3-(3-((1-Aminocyclopentyl)methoxy)-4-cyano-5-(methylthio)phenyl)-6-(pyrrolidin-1-yl)imidazo[1,2-a]pyridine-5-carbonitrile. $^1$H NMR (400 MHz, MeOD) δ 7.64-7.70 (m, 2H), 7.29 (d, 1H), 7.15 (s, 1H), 7.12 (s, 1H), 4.07 (s, 2H), 3.62-3.69 (m, 4H), 2.64 (s, 3H), 2.04-2.11 (m, 4H), 1.81-1.92 (m, 4H), 1.60-1.78 (m, 4H). MS (M+H)$^+$ 473.1.

Example 48

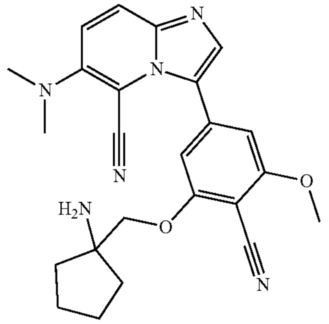

3-(3-((1-Aminocyclopentyl)methoxy)-4-cyano-5-methoxyphenyl)-6-(dimethylamino)imidazo[1,2-a]pyridine-5-carbonitrile. $^1$H NMR (400 MHz, DMSO-$d_6$) δ 7.84 (d, 1H), 7.81 (s, 1H), 7.38 (d, 1H), 7.05 (app d, 2H), 4.01 (s, 2H), 3.96 (s, 3H), 3.16 (s, 6H), 1.40-1.85 (m, 8H). MS (M+H)$^+$ 431.2.

Example 49

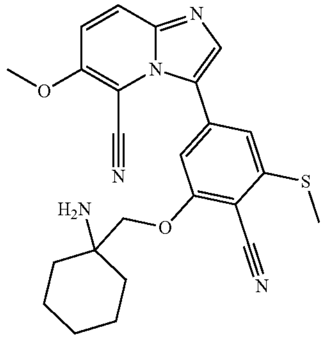

3-(3-((1-Aminocyclohexyl)methoxy)-4-cyano-5-(methylthio)phenyl)-6-methoxyimidazo[1,2-a]pyridine-5-carbonitrile. $^1$H NMR (400 MHz, MeOD) δ 7.98 (d, 1H), 7.83 (s, 1H), 7.59 (d, 1H), 7.16 (app d, 2H), 4.10 (s, 3H), 4.04 (s, 2H), 2.62 (s, 3H), 1.61-1.77 (m, 4H), 1.40-1.60 (m, 6H). MS (M+H)$^+$ 448.4.

Example 50

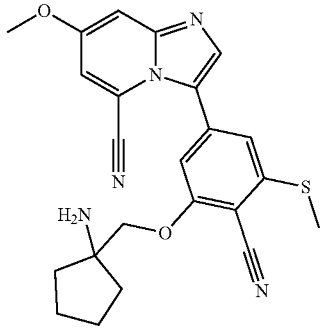

3-(3-((1-Aminocyclopentyl)methoxy)-4-cyano-5-(methylthio)phenyl)-7-methoxyimidazo[1,2-a]pyridine-5-carbonitrile. $^1$H NMR (400 MHz, MeOD) δ 7.70 (s, 1H), 7.49 (d, 1H), 7.32 (d, 1H), 7.18 (app d, 2H), 4.07 (s, 2H), 3.97 (s, 3H), 2.62 (s, 3H), 1.82-1.91 (m, 4H), 1.60-1.77 (m, 4H). MS (M+H)$^+$ 434.3.

Example 51

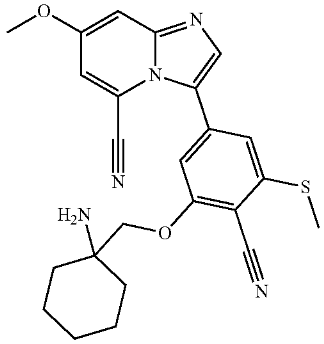

3-(3-((1-Aminocyclohexyl)methoxy)-4-cyano-5-(methylthio)phenyl)-7-methoxyimidazo[1,2-a]pyridine-5-carbonitrile. $^1$H NMR (400 MHz, MeOD) δ 7.70 (s, 1H), 7.49 (d, 1H), 7.32 (d, 1H), 7.19 (s, 1H), 7.18 (s, 1H), 4.04 (s, 2H), 3.98 (s, 3H), 2.62 (s, 3H), 1.62-1.79 (m, 4H), 1.49-1.60 (m, 6H). MS $(M+H)^+$ 448.4.

Example 52

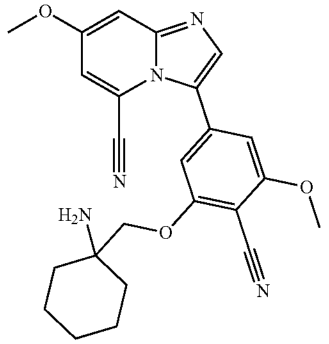

3-(3-((1-Aminocyclohexyl)methoxy)-4-cyano-5-methoxyphenyl)-7-methoxyimidazo[1,2-a]pyridine-5-carbonitrile. $^1$H NMR (400 MHz, MeOD) δ 7.68 (s, 1H), 7.45 (d, 1H), 7.28 (d, 1H), 6.99 (s, 1H), 6.97 (s, 1H), 4.02 (s, 2H), 3.98 (s, 3H), 3.96 (s, 3H), 1.60-1.75 (m, 4H), 1.49-1.58 (m, 6H). MS $(M+H)^+$ 432.3.

Preparation L 2-((1-Aminocyclopentyl)methoxy)-4-bromo-6-(methylthio)benzonitrile. A solution of KHMDS in THF (1M, 1.0 L, 1.00 mol) was added dropwise to a solution of 4-bromo-2-fluoro-6-(methylthio)benzonitrile (240 g, 975 mmol) and (1-aminocyclopentyl)methanol (101 g, 878 mmol) in THF (2.5 L) at 10° C. The mixture was stirred at 25° C. for 1 h. Five reactions on this scale were poured together into saturated aqueous $NH_4Cl$ solution (1 L) and were stirred for 10 min. The aqueous phase was extracted with EtOAc (3×1.5 L). The combined organic phase was washed with brine (2×1.5 L), dried over $Na_2SO_4$, filtered and concentrated. The residue was purified by silica gel chromatography (10:1 EtOAc:MeOH) to afford 2-((1-aminocyclopentyl)methoxy)-4-bromo-6-(methylthio)benzonitrile as a brown solid (700 g). $^1$H NMR (400 MHz, DMSO-$d_6$) δ 7.27 (d, 1H), 7.15 (d, 1H), 3.98 (s, 2H), 2.60 (s, 3H,) 1.69-1.82 (m, 2H), 1.56-1.68 (m, 4H), 1.39-1.50 (m, 2H).

Preparation M tert-Butyl (1-((5-bromo-2-cyano-3-(methylthio)phenoxy)methyl)cyclopentyl)-carbamate. To a solution of 2-((1-aminocyclopentyl)methoxy)-4-bromo-6-(methylthio)benzonitrile (347 g, 1.02 mol) in THF (2.9 L) and EtOH (580 mL) was added $Boc_2O$ (444 g, 2.03 mol). The mixture was stirred at 20° C. for 12 h. Two reactions on this scale were combined and were concentrated. The crude product was triturated with petroleum ether (1 L) at 25° C. for 2 h to give tert-butyl (1-((5-bromo-2-cyano-3-(methylthio)phenoxy)methyl)cyclopentyl)carbamate as a brown solid (820 g) that was used without further purification. $^1$H NMR (400 MHz, $CDCl_3$) δ 6.94 (d, 1H), 6.92 (d, 1H), 4.73 (br s, 1H), 4.24 (s, 2H), 2.54 (s, 3H), 1.85-2.00 (m, 4H), 1.67-1.84 (m, 4H,) 1.40 (s, 9H).

Preparation N tert-Butyl (1-((2-cyano-3-(methylthio)-5-(4,4,5,5-tetramethyl-1,3,2-dioxaborolan-2-yl)phenoxy)methyl)cyclopentyl)carbamate. To a suspension of tert-butyl (1-((5-bromo-2-cyano-3-(methylthio)phenoxy)methyl)cyclopentyl) carbamate (205 g, 464 mmol) and $B_2Pin_2$ (130 g, 511 mmol) in MeTHF (3 L) was added sequentially KOAc (137 g, 1.39 mol), XPhos (11.1 g, 23.2 mmol), and Pd(OAc) 2 (2.61 g, 11.6 mmol) at 25° C. The mixture was stirred under $N_2$ at 90° C. for 3.5 h. The mixture was cooled to 20° C., diluted with DCM (3 L), and filtered through Celite. The filtrate was washed sequentially with $H_2O$ (3 L) and brine (1.5 L), dried over $MgSO_4$, filtered, and concentrated. The crude products from four reactions on this scale were combined and triturated with petroleum ether (5 mL/gram crude product) at 25° C. for 1 h to provide (1-((2-cyano-3-(methylthio)-5-(4,4,5,5-tetramethyl-1,3,2-dioxaborolan-2-yl)phenoxy)methyl)cyclopentyl)carbamate as a gray solid (800 g). $^1$H NMR (400 MHz, $CDCl_3$) δ 7.25 (s, 1H), 7.13 (s, 1H), 4.79 (br s, 1H), 4.25 (s, 2H), 2.59 (s, 3H), 1.86-2.02 (m, 4H), 1.66-1.84 (m, 4H), 1.38 (s, 9H), 1.35 (s, 12H).

Preparation O 3-(Dimethylamino)picolinonitrile. To 3-fluoropicolinonitrile (10 g, 82 mmol) at 0° C. was added $Me_2NH$ solution (40% in $H_2O$, 31.1 mL, 246 mmol) dropwise over 3 min. The reaction was stirred at room temperature for 90 min, then was diluted with $H_2O$ and EtOAc. The layers were separated and the organic was washed with $H_2O$ (2×30 mL), and the combined aqueous layers were then extracted with EtOAc (3×30 mL). The combined organics were dried over $MgSO_4$, filtered, and concentrated to provide 3-(dimethylamino)picolinonitrile as a white solid (11.2 g). $^1$H NMR (400 MHz, DMSO-$d_6$) δ 8.09 (app t, 1H), 7.49 (app d, 2H), 3.05 (s, 6H). MS $(M+H)^+$ 148.4.

Preparation P

6-Bromo-3-(dimethylamino)picolinonitrile. A solution of 3-(dimethylamino)picolino-nitrile (11.2 g, 76.3 mmol) and NBS (14.9 g, 83.9 mmol) in $CH_3CN$ (231 mL) was stirred at room temperature for 15 h. The mixture was concentrated and the resulting residue was partitioned between EtOAc (100 mL) and aqueous NaOH solution (1N, 100 mL). The aqueous layer was extracted with EtOAc (3×50 mL). The combined organic layers were dried over $MgSO_4$, filtered, and concentrated to afford 6-bromo-3-(dimethylamino)picolinonitrile as a yellow solid (17.1 g). $^1$H NMR (400 MHz, DMSO-$d_6$) δ 7.65 (d, 1H), 7.45 (d, 1H), 3.10 (s, 6H). MS $(M+H)^+$ 226.0/228.0.

Preparation Q tert-Butyl (6-cyano-5-(dimethylamino)pyridin-2-yl)carbamate. Dioxane (180 mL) was added to a mixture of 6-bromo-3-(dimethylamino)picolinonitrile (12.3 g, 54.4 mmol), tert-butyl carbamate (7.05 g, 60.2 mmol), Pd(OAc) 2 (70.7 mg, 0.315 mmol), Xantphos (271 mg, 0.469 mmol), and $Cs_2CO_3$ (47.9 g, 147 mmol), and the mixture was sparged with $N_2$ for 15 min, then was heated at 100° C. for 22 h. The mixture was cooled to room temperature and was partitioned between $H_2O$ (300 mL) and EtOAc (300 mL). The aqueous layer was extracted with EtOAc (4×225 mL). The organic layers were combined, dried over anhydrous $Na_2SO_4$, filtered, and concentrated. The resulting residue was dissolved in EtOAc (200 mL), and the solution was filtered through Celite. The filtrate was concentrated, diluted with $Et_2O$ (65 mL), and sonicated to a freely-flowing mixture. Heptane (80 mL) was added and the resulting mixture was stirred for 21 h. The solids were collected and were dried under vacuum to provide tert-butyl (6-cyano-5-(dimethylamino)pyridin-2-yl)carbamate as a beige solid (12.1 g). $^1H$ NMR (400 MHz, $CDCl_3$) δ 8.03 (d, 1H), 7.32 (d, 1H), 7.10 (br s, 1H), 3.03 (s, 6H), 1.52 (s, 9H).

Preparation R

6-Amino-3-(dimethylamino)picolinonitrile. EtOAc (190 mL) was added to a mixture of tert-butyl (6-cyano-5-(dimethylamino)pyridin-2-yl)carbamate (9.95 g, 37.9 mmol) and p-toluenesulfonic acid monohydrate (14.4 g, 75.8 mmol), and the mixture was stirred at 70° C. for 24 h. The suspension was then cooled to room temperature and the solids were collected and were dried under vacuum. The solids were then diluted with DCM (200 mL) and saturated aqueous $NaHCO_3$ solution (200 mL), and the mixture was stirred for 30 min. The layers were then separated and the aqueous layer was extracted with EtOAc (3×100 mL). The combined organic layers were dried over $Na_2SO_4$, filtered, and concentrated to provide 6-amino-3-(dimethylamino)picolinonitrile as a yellow solid (5.51 g). $^1H$ NMR (400 MHz, DMSO-$d_6$) δ 7.44 (d, 1H), 6.71 (d, 1H), 6.08 (s, 2H), 2.72 (s, 6H).

Preparation S

6-Amino-3-(dimethylamino)picolinonitrile p-toluenesulfonic acid salt. A mixture of 6-amino-3-(dimethylamino) picolinonitrile (5.51 g, 34.0 mmol) and p-toluenesulfonic acid monohydrate (7.75 g, 40.8 mmol) in EtOAc (170 mL) was stirred at room temperature for 18 h. The suspension was filtered, and the collected solids were washed with $Et_2O$ (50 mL) and then were dried under vacuum to provide 6-amino-3-(dimethylamino)picolino-nitrile p-toluenesulfonic acid salt as a yellow solid (11.4 g). $^1H$ NMR (400 MHz, DMSO-$d_6$) δ 7.45-7.53 (m, 3H), 7.11 (d, 2H), 6.75 (d, 1H), 2.76 (s, 6H), 2.29 (s, 3H).

Preparation T 6-(Dimethylamino)imidazo[1,2-a]pyridine-5-carbonitrile. To 6-amino-3-(dimethylamino)picolinonitrile p-toluenesulfonic acid salt (11.2 g, 33.5 mmol) and $NaHCO_3$ (5.62 g, 66.9 mmol) was added i-PrOH (200 mL). Chloroacetaldehyde solution (55% in $H_2O$, 19.6 mL, 134 mmol) was added dropwise and the mixture was stirred at 80° C. for 3 h. The mixture was concentrated and EtOAc (100 mL) was added to the residue. The organic layer was washed with saturated aqueous $Na_2CO_3$ solution (3×50 mL). The organic layer was dried over $Na_2SO_4$, filtered, and concentrated. The residue was passed through a plug of silica gel with 1:1 heptanes-EtOAc (500 mL). The silica was then washed with 9:1 DCM-MeOH (750 mL) and the filtrate was concentrated to provide 6-(dimethylamino)imidazo[1,2-a]pyridine-5-carbonitrile as a yellow solid (6.2 g). $^1H$ NMR (500 MHz, DMSO-$d_6$) δ 7.83 (app s, 1H), 7.74 (d, 1H), 7.59 (d, 1H), 7.22 (d, 1H), 3.16 (s, 6H).

Preparation U 6-(Dimethylamino)-3-iodoimidazo[1,2-a]pyridine-5-carbonitrile. To 6-(dimethylamino)imidazo[1,2-a]pyridine-5-carbonitrile (6.2 g, 33 mmol) and NIS (8.99 g, 40.0 mmol) was added $CH_3CN$ (166 mL). The mixture was stirred at room temperature for 65 h and then was concentrated to approximately half of the original volume. The suspension was filtered and the solids were washed with cold $CH_3CN$ (2×15 mL) to provide 6-(dimethylamino)-3-iodoimidazo[1,2-a]pyridine-5-carbonitrile as a yellow solid (9.7 g). $^1H$ NMR (400 MHz, DMSO-$d_6$) δ 7.72 (d, 1H), 7.64 (s, 1H), 7.29 (d, 1H), 3.11 (s, 6H).

Preparation V tert-Butyl (1-((2-cyano-5-(5-cyano-6-(dimethylamino) imidazo[1,2-a]pyridin-3-yl)-3-(methylthio)phenoxy) methyl)cyclopentyl)carbamate. MeTHF (940 mL) and $H_2O$ (230 mL) were added to a mixture of 6-(dimethylamino)-3-iodoimidazo[1,2-a]pyridine-5-carbonitrile (29.5 g, 94.6 mmol), tert-butyl (1-((2-cyano-3-(methylthio)-5-(4,4,5,5-tetramethyl-1,3,2-dioxaborolan-2-yl)phenoxy)methyl)cyclopentyl)carbamate (47.1 g, 96.5 mmol), $K_3PO_4$ (62.1 g, 284 mmol), and $Pd(PPh_3)_2Cl_2$ (3.39 g, 4.73 mmol) under $N_2$. The resulting solution was sparged with $N_2$ for 10 min and then was heated at 80° C. for 52 h. The mixture was cooled to room temperature, then was diluted with $H_2O$ (100 mL). The solids were collected by filtration and were dried under vacuum. The solids were dissolved in DCM (200 mL) and Celite (30 g) was added. The mixture was stirred for 20 min, then was filtered through a pad of Celite, rinsing with DCM (3×50 mL). The filtrate was concentrated to provide tert-butyl (1-((2-cyano-5-(5-cyano-6-(dimethylamino)imidazo [1,2-a]pyridin-3-yl)-3-(methylthio)phenoxy)methyl)cyclopentyl)-carbamate as a yellow solid (41.5 g). $^1H$ NMR (400 MHz, DMSO-$d_6$) δ 7.86 (s, 1H), 7.84 (d, 1H), 7.38 (d, 1H), 7.22 (s, 1H), 7.18 (s, 1H), 6.82 (br s, 1H), 4.34 (br s, 2H), 3.16 (s, 6H), 2.64 (s, 3H), 1.88-1.98 (m, 2H), 1.70-1.81 (m, 2H), 1.56-1.69 (m, 4H), 1.27 (s, 9H). MS (M+H)+547.5.

Example 43

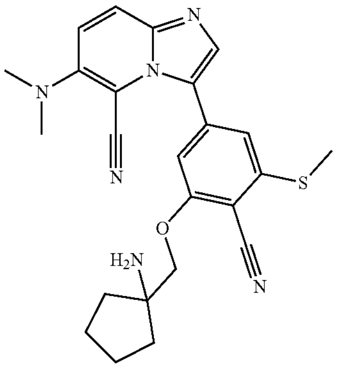

3-(3-((1-Aminocyclopentyl)methoxy)-4-cyano-5-(methylthio)phenyl)-6-(dimethylamino)imidazo[1,2-a]pyridine-5-carbonitrile. Acetyl chloride (0.680 mL, 9.53 mmol) was added to EtOH (5.56 mL) and the mixture was heated at 50° C. for 30 min. The resulting solution was added in a single portion to tert-butyl (1-((2-cyano-5-(5-cyano-6-(dimethylamino)imidazo[1,2-a]pyridin-3-yl)-3-(methylthio)phenoxy)-methyl)cyclopentyl)carbamate (521 mg, 0.953 mmol), and the mixture was stirred at 50° C. under $N_2$ for 4 h. The mixture was concentrated, and the resulting residue was diluted with DCM (30 mL) and saturated aqueous $Na_2CO_3$ solution (30 mL). The biphasic mixture was stirred for 15 min and the organic layer was collected. The aqueous layer was extracted with DCM (2×15 mL) and the combined organics were dried over $Na_2SO_4$, filtered, and concentrated to afford 3-(3-((1-aminocyclopentyl)methoxy)-4-cyano-5-(methylthio)phenyl)-6-(dimethylamino)imidazo[1,2-a]pyridine-5-carbonitrile as a yellow solid (426 mg). $^1$H NMR (400 MHz, MeOD) δ 7.73 (app t, 2H), 7.41 (d, 1H), 7.17 (s, 1H), 7.15 (s, 1H), 4.07 (s, 2H), 3.22 (s, 6H), 2.64 (s, 3H), 1.82-1.91 (m, 4H), 1.70-1.77 (m, 2H), 1.58-1.67 (m, 2H). MS $(M+H)^+$ 447.3.

Preparation W tert-Butyl (5-cyanoimidazo[1,2-a]pyridin-6-yl)(methyl) carbamate. To 6-bromoimidazo[1,2-a]pyridine-5-carbonitrile (565 mg, 2.54 mmol), cesium carbonate (2.49 g, 7.63 mmol) and XPhos-G3-Palladacycle (241 mg, 0.254 mmol) was added toluene (25.4 mL) and tert-butyl methylcarbamate (567 mg, 4.33 mmol). The mixture was degassed with $N_2$ for 5 min and was heated at 100° C. under an atmosphere of $N_2$. After 22 h the sample was cooled to room temperature, and was diluted with EtOAc (10 mL). The mixture was washed with brine (3×10 mL) and the organic layer dried over $MgSO_4$, filtered, and concentrated. The residue was purified via silica gel chromatography (0-100% EtOAc-heptane) to afford tert-butyl (5-cyanoimidazo[1,2-a]pyridin-6-yl)(methyl)carbamate (292 mg). $^1$H NMR (400 MHz, DMSO-$d_6$) δ 8.18 (s, 1H), 8.02 (d, 1H), 7.86 (s, 1H), 7.45 (d, 1H), 3.23 (s, 3H), 1.39 (s, 9H).

Preparation X 6-(Methylamino)imidazo[1,2-a]pyridine-5-carbonitrile. To a solution of tert-butyl (5-cyanoimidazo[1,2-a]pyridin-6-yl)(methyl)carbamate (400 mg, 1.47 mmol) in DCM (7.34 mL) was added TFA (95.9 mmol, 7.34 mL) at 0° C. The reaction was stirred at 0° C. for 2 h, then was concentrated. The solids were partitioned between EtOAc (10 mL) and saturated aqueous $NaHCO_3$ solution. The aqueous layer was extracted with EtOAc (3×10 mL). The combined organics were dried over $MgSO_4$, filtered, and concentrated. The residue was purified via silica gel chromatography (0-20% MeOH-DCM) to provide 6-(methylamino)imidazo[1,2-a]pyridine-5-carbonitrile (234 mg). $^1$H NMR (400 MHz, DMSO-$d_6$) δ 7.75 (s, 1H), 7.70 (d, 1H), 7.54 (d, 1H), 6.97 (d, 1H), 2.96 (d, 3H). MS $(M+H)^+$ 172.9.

Preparation Y

3-Iodo-6-(methylamino)imidazo[1,2-a]pyridine-5-carbonitrile. To 6-(Methylamino)imidazo[1,2-a]pyridine-5-carbonitrile (223 mg, 1.30 mmol) and NIS (350 mg, 1.55 mmol) was added $CH_3CN$ (5.63 mL), and the resulting mixture was stirred at room temperature for 20 h. The mixture was filtered to collect the solids which were washed with cold $CH_3CN$ (2×10 mL), then were dried under vacuum to provide 3-iodo-6-(methylamino)imidazo[1,2-a]pyridine-5-carbonitrile as a yellow solid (311 mg). $^1$H NMR (400 MHz, DMSO-$d_6$) δ 7.72 (d, 1H), 7.57 (s, 1H), 7.07 (d, 1H), 6.50-6.55 (m, 1H), 2.92 (d, 3H). MS $(M+H)^+$ 299.1. The following example was synthesized by analogous methods and starting materials as described for 3-(3-((1-aminocyclohexyl)methoxy)-4-cyano-5-(methylthio)phenyl)imidazo[1,2-a]pyridine-5-carbonitrile.

Example 53

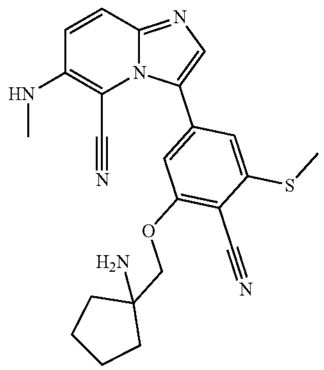 [SMILES: CNc1ccc2ncc(-c3cc(OCC4(N)CCCC4)c(C#N)c(SC)c3)n2c1C#N]

3-(3-((1-Aminocyclopentyl)methoxy)-4-cyano-5-(methylthio)phenyl)-6-(methylamino)imidazo[1,2-a]pyridine-5-carbonitrile. $^1$H NMR (400 MHz, DMSO-$d_6$) δ 7.84 (d, 1H), 7.72 (s, 1H), 7.17 (s, 1H), 7.14 (d, 1H), 7.12 (s, 1H), 6.61-6.68 (m, 1H), 4.02 (s, 2H), 2.93 (d, 3H), 2.63 (s, 3H). MS $(M+H)^+$ 433.4. HPLC: Waters X-bridge BEH Shield RP 18, 2.1×100 mm 2.5μ; A: 0.1% MsOH in $H_2O$, B: 0.1% MsOH in $CH_3CN$, Gradient: 5%-100% B over 8.2 min; 0.5 mL/min, 45° C.; retention time, 1.96 min.

Preparation Z

2-Fluoro-6-methoxy-4-(4,4,5,5-tetramethyl-1,3,2-dioxaborolan-2-yl)benzonitrile. A flask containing a mixture of 4-bromo-2-fluoro-6-methoxybenzonitrile (256 g, 1.11 mol), $B_2(pin)_2$ (339 g, 1.34 mol), and KOAc (328 g, 3.34 mol) in dioxane (3 L) at 25° C. was purged with $N_2$ (3×). $PdCl_2$(dppf) (24.4 g, 33.3 mmol) was added and the resulting mixture was purged with $N_2$ (3×), then was heated at 90° C. for 16 h. The mixture was cooled to 25° C. and was concentrated. The resulting residue was diluted with $H_2O$ (10 L) and EtOAc (10 L). The mixture was filtered to remove insoluble solids, then the layers were separated. The aqueous layer was further extracted with EtOAc (3 L). The combined organics were dried over $Na_2SO_4$, filtered, and concentrated. This crude product and crude product from two additional reactions run on the same scale were combined and were purified by silica gel chromatography (20:1 to 5:1 petroleum ether-EtOAc). Fractions containing desired product (~3 L) were combined and a suspension formed; the slurry was further diluted with petroleum ether (2 L) and the resulting suspension was stirred at 25° C. for 30 min. The solids were collected by filtration to afford 2-fluoro-6-methoxy-4-(4,4,5,5-tetramethyl-1,3,2-dioxaborolan-2-yl) benzonitrile as white solid (765 g). $^1$H NMR (400 MHz, $CDCl_3$) δ 7.17 (d, 1H), 7.13 (s, 1H), 3.98 (s, 3H), 1.34 (s, 12H).

Preparation AA

2-Fluoro-6-methoxy-4-(5-methoxyimidazo[1,2-a]pyridin-3-yl)benzonitrile. A flask containing a mixture of 3-bromo-5-methoxyimidazo[1,2-a]pyridine (260 g, 1.15 mol), 2-fluoro-6-methoxy-4-(4,4,5,5-tetramethyl-1,3,2-dioxaborolan-2-yl)benzonitrile (380.7 g, 1.37 mol), and $K_3PO_4$ (729.1 g, 3.44 mol) in dioxane (2.6 L) and $H_2O$ (0.31 L) at 20° C. was purged with $N_2$ (3×). $PdCl_2$(dppf) (25.1 g, 34.3 mmol) was added, and the resulting mixture was purged with $N_2$ (3×), then was heated at 90° C. for 16 h. The mixture was cooled to 20° C. and was combined with material from another reaction run on the same scale. The combined mixture was concentrated, and the resulting residue was diluted with DCM-MeOH (10:1, 20 L) and $H_2O$ (10 L). The insoluble solids were removed by filtration, then the layers were separated, and the aqueous was extracted with DCM (5 L). The combined organics were dried over $Na_2SO_4$, filtered, and concentrated. The resulting residue was purified by silica gel chromatography (10:0 to 10:1 DCM-MeOH). Fractions containing desired product (~6 L) were combined and a suspension formed. The solids were collected by filtration, rinsing with MTBE, to afford 2-fluoro-6-methoxy-4-(5-methoxyimidazo[1,2-a]pyridin-3-yl)benzonitrile as a yellow solid (399 g). $^1$H NMR (400 MHz, $CDCl_3$) δ 7.61 (s, 1H), 7.37-7.35 (m, 1H), 7.32-7.27 (m, 1H), 6.87-6.79 (m, 2H), 6.16 (dd, 1H), 3.97 (s, 3H), 3.93 (s, 3H). MS $(M+H)^+$ 297.9.

Preparation AB (5S,6R)-6-Ethyl-1,3-diazaspiro[4.4]nonane-2,4-dione and (5R,6S)-6-ethyl-1,3-diazaspiro[4.4]nonane-2,4-dione) (racemate). KF (1.93 kg, 33.9 mol), TMSCN (873 g, 8.80 mol), and ammonium carbonate (1.595 kg) were added sequentially to racemic 2-ethylcyclopentan-1-one (759 g, 6.77 mol) in $H_2O$ (7.60 L) and 2,2,2-trifluoroethanol (7.60 L), and the resulting mixture was stirred at 80° C. for 16 h. The mixture was then concentrated and the resulting solid was dried to afford a mixture of (5R,6R)-6-ethyl-1,3-diazaspiro[4.4]nonane-2,4-dione/(5R,6S)-6-ethyl-1,3-diazaspiro[4.4]nonane-2,4-dione) (cis racemate) and (55,65)-6-ethyl-1,3-diazaspiro[4.4]nonane-2,4-dione/(5R,6R)-6-ethyl-1,3-diazaspiro[4.4]nonane-2,4-dione) (trans racemate) as a solid (985 g). UPLC: Cortecs C18, 100 mm×4.6 mm, 2.7p; A: 0.05% TFA-$H_2O$, B: 0.05% TFA-$CH_3CN$; Gradient: 10%-65% B over 5 min, 65% B for 2 min; 1 mL/min; 40° C.; 210 nM; retention times, cis racemate (2.7 min), trans racemate (2.9 min); cis:trans, 88:12.

Preparation AC (5S,6R)-6-Ethyl-1,3-diazaspiro[4.4]nonane-2,4-dione and (5R,6S)-6-ethyl-1,3-diazaspiro[4.4]nonane-2,4-dione (racemate). A mixture of (5S,6R)-6-ethyl-1,3-diazaspiro[4.4]nonane-2,4-dione/(5R,6S)-6-ethyl-1,3-diazaspiro[4.4]nonane-2,4-dione (cis racemate) and (5S,6S)-6-ethyl-1,3-diazaspiro[4.4]nonane-2,4-dione/(5R,6R)-6-ethyl-1,3-diazaspiro[4.4]nonane-2,4-dione (trans racemate) (>83:17 cis:trans, 1194 g, 5.98 mol) in HOAc (2.626 L) was stirred at 40° C. for 10 min, then the mixture was seeded with a sample of cis racemate (5S,6R)-6-ethyl-1,3-diazaspiro[4.4]nonane-2,4-dione/(5R,6S)-6-ethyl-1,3-diazaspiro[4.4]nonane-2,4-dione. The mixture was cooled to 20° C., then was diluted with $H_2O$ (2.00 L), and the resulting mixture was stirred at 20° C. for 16 h. The solids were collected by filtration, rinsing with $H_2O$ (1 L), then were dried to afford cis racemate (5S,6R)-6-ethyl-1,3-diazaspiro[4.4]nonane-2,4-dione/(5R,6S)-6-ethyl-1,3-diazaspiro[4.4]nonane-2,4-dione (795 g). UPLC: Waters Acquity UPLC BEH C8, 2.1×100 mm, 1.7μ; A: 0.1% TFA-$H_2O$, B: 0.1% TFA-$CH_3CN$; Gradient: 10%-95% B over 5 min, 95% B for 3 min; 0.4 mL/min; 40° C.; 210 nM; retention times, cis racemate (2.5 min), trans racemate (2.6 min); cis:trans, 95:5.

Preparation AD (1S,2R)-1-Amino-2-ethylcyclopentane-1-carboxylic acid hydrobromide salt and (1R,2S)-1-amino-2-ethylcyclopentane-1-carboxylic acid hydrobromide salt (racemate). Hydrobromic acid (48% by weight in $H_2O$, 400 mL) and phosphoric acid (85% by weight in $H_2O$, 50 mL) were added sequentially to racemic (5S,6R)-6-ethyl-1,3-diazaspiro[4.4]nonane-2,4-dione/(5R,6S)-6-ethyl-1,3-diazaspiro[4.4]nonane-2,4-dione (50 g, 270 mmol), and the resulting mixture was heated at 135° C. for 72 h. The mixture was then cooled to 0° C. and was stirred at that temperature for 2 h. The resulting solids were collected by filtration and were dried at 45° C. for 20 h to afford racemic (1R,2S)-1-amino-2-ethylcyclopentane-1-carboxylic acid hydrobromide salt/(1S,2R)-1-amino-2-ethylcyclopentane-1-carboxylic acid hydrobromide salt (65 g). Quantitative $^1$H NMR analysis of the isolated material indicated 52.8% by weight 1-amino-2-ethylcyclo-pentane-1-carboxylic acid. $^1$H NMR (400 MHz, MeOD) δ 2.53-2.35 (m, 2H), 2.25-2.09 (m, 1H), 2.02-1.83 (m, 3H), 1.59-1.40 (m, 2H), 1.36-1.25 (m, 1H), 0.99 (t, 3H).

Preparation AE

Methyl (1S,2R)-1-amino-2-ethylcyclopentane-1-carboxylate and methyl (1R,2S)-1-amino-2-ethylcyclopentane-1-carboxylate (racemate). Thionyl chloride (111 g, 933 mmol) was added dropwise to MeOH (864 mL) at 0° C., then the resulting solution was stirred at 20° C. for 30 min. Racemic (1R,2S)-1-amino-2-ethylcyclopentane-1-carboxylic acid/(1S,2R)-1-amino-2-ethylcyclopentane-1-carboxylic acid hydrobromide salt (62 g, assayed by quantitative $^1$H NMR as 52.8% 1-amino-2-ethylcyclopentane-1-carboxylic acid by weight (32.7 g, 179 mmol)) was added, and the resulting mixture was stirred at 50° C. for 16 h. The mixture was concentrated to a volume of approximately 0.16 L, then was twice sequentially diluted with MTBE (0.2 L) and concentrated to approximately 0.16 L. $H_2O$ (0.1 L) was added and the aqueous layer was collected. MTBE (0.16 L) was added to the aqueous layer and the pH was adjusted to ~8 by the addition of aqueous $Na_2CO_3$ solution (15% by weight) at 0° C. The mixture was then stirred at 25° C. for 1 h. The layers were separated, and the aqueous was further extracted with MTBE (4×0.16 L). The combined organics were washed with brine (16 mL) and then were concentrated to afford racemic methyl (1R,2S)-1-amino-2-ethylcyclopentane-1-carboxylate/methyl (1S,2R)-1-amino-2-ethylcyclopentane-1-carboxylate as an oil (29 g). $^1$H NMR (400 MHz, MeOD) δ 3.71 (s, 3H), 2.25-2.18 (m, 1H), 2.15-2.07 (m, 1H), 2.01-1.91 (m, 1H), 1.89-1.60 (m, 3H), 1.53-1.20 (m, 3H), 0.89 (t, 3H).

Preparation AF

Methyl (1S,2R)-1-amino-2-ethylcyclopentane-1-carboxylate. CES E-2 enzyme (Amano Enzyme USA, item number SUNDV-R&D1 CES E-2 (Chiral), 6.25 g) was dissolved in pH 7 potassium phosphate buffer (0.2M, 932 mL) at 20° C. A solution of racemic methyl (1R,2S)-1-amino-2-ethylcyclopentane-1-carboxylate/methyl (1S,2R)-1-amino-2-ethylcyclopentane-1-carboxylate (31.1 g, 181 mmol) in $CH_3CN$ (90 mL, plus 13-mL rinse) was added over 5 min. After stirring for 22 h, Celite™ (62 g) was added and the mixture was stirred for 5 min. MeTHF (932 mL) was added, and the resulting mixture was stirred for 45 min. The mixture was then filtered through a pad of Celite (62 g, pre-washed with $H_2O$), rinsing sequentially with $H_2O$ and MeTHF (125 mL each). The layers of the filtrate were separated, and the aqueous was adjusted to pH~7.8 by addition of aqueous NaOH solution (1N, 19 mL), then the aqueous was further extracted with MeTHF (932 mL). The organic layers and emulsion were filtered through a pad of Celite (31 g, pre-washed with $H_2O$), then the combined organics were dried over $MgSO_4$, filtered, and concentrated. The resulting residue was dissolved in DCM (150 mL), dried over $MgSO_4$, filtered, and concentrated to afford a methyl (1S,2R)-1-amino-2-ethylcyclopentane-1-carboxylate as an oil (12.3 g). $^1H$ NMR (400 MHz, MeOD) δ 3.71 (s, 3H), 2.26-2.18 (m, 1H), 2.16-2.07 (m, 1H), 2.00-1.92 (m, 1H), 1.86-1.62 (m, 3H), 1.53-1.19 (m, 3H), 0.89 (t, 3H). Chiral SFC for analysis of cis enantiomers: ChiralPak IG, 250 mm×4.6 mm, 5μ; A: $CO_2$, B: [MeOH+0.2% $NH_3$ (7N in MeOH)], Gradient: 10% B for 5 min, 10%-60% B over 3.5 min; 3 mL/min; 40° C.; 120 bar; 210 nM; MS detection by total ion count based on (M)=171; retention times, methyl (1S,2R)-1-amino-2-ethylcyclopentane-1-carboxylate (3.6 min), methyl (1R,2S)-1-amino-2-ethylcyclopentane-1-carboxylate (3.4 min); (1S,2R)-isomer: (1R,2S)-isomer>98:2 based on MS total ion count. Chiral SFC method for detection of all 4 stereoisomers: ChiralTech IG, 250 mm×4.6 mm, 5μ; 85:15 $CO_2$:[MeOH+0.2% $NH_3$ (7N in MeOH)], 4.0 mL/min; 40° C.; 120 bar; 210 nM; retention times, methyl (1S,2R)-1-amino-2-ethylcyclopentane-1-carboxylate (2.7 min), methyl (1R,2S)-1-amino-2-ethylcyclopentane-1-carboxylate (2.4 min), two enantiomers of trans methyl 1-amino-2-ethylcyclopentane-1-carboxylate (2.0 min and 3.6 min, absolute stereochemistry not assigned).

Preparation AG ((1S,2R)-1-Amino-2-ethylcyclopentyl)methanol. A solution of methyl (1S,2R)-1-amino-2-ethylcyclopentane-1-carboxylate (7.13 g, 41.6 mmol) in THF (167 mL) was added dropwise over 20 min to a solution of $LiBH_4$ in THF (2.0M, 100 mL, 200 mmol). The resulting solution was heated at 59° C. for 18 h. The mixture was then cooled to 0° C. and MeOH (200 mL) was slowly added, and the resulting solution was stirred for 1.5 h resulting in formation of a precipitate. The suspension was concentrated to remove solvent, and the resulting solid was dissolved in aqueous KOH solution (20% by weight, 150 mL) and that solution was stirred at ambient temperature for 3 days. The solution was extracted with MeTHF (3×100 mL), and the combined organics were washed with brine (200 mL), dried over $Na_2SO_4$, filtered, and concentrated to afford crude ((1S,2R)-1-amino-2-ethylcyclopentyl)methanol as an oil (5.57 g). This material was combined with another portion of 2.84 g crude (1S,2R)-1-amino-2-ethylcyclopentyl)methanol from an analogous reaction, and the combined material was purified by silica gel chromatography (0%-20% DCM-MeOH (containing 2% aqueous $NH_4OH$ solution (25% by weight)) to afford ((1S,2R)-1-amino-2-ethylcyclopentyl) methanol as an oil (5.01 g). $^1H$ NMR (400 MHz, MeOD) δ 3.39 (m, 2H), 1.98-1.88 (m, 1H), 1.86-1.65 (m, 2H), 1.62-1.32 (m, 5H), 1.24-1.05 (m, 1H), 0.94 (t, 3H).

Example 2A, Alternate Procedure

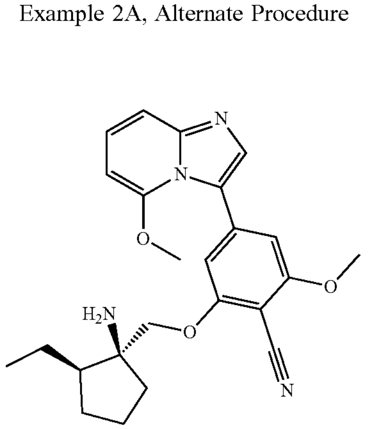

2-(((1S,2R)-1-Amino-2-ethylcyclopentyl)methoxy)-6-methoxy-4-(5-methoxyimidazo[1,2-a]pyridin-3-yl)benzonitrile. A solution of ((1S,2R)-1-amino-2-ethylcyclopentyl) methanol (3.09 g, 21.6 mmol) in THF (20 mL, plus 30-mL rinse) was added to 2-fluoro-6-methoxy-4-(5-methoxyimidazo[1,2-a]pyridin-3-yl)benzonitrile (4.58 g, 15.4 mmol). A solution of NaOtBu in THF (2M, 23.1 mL, 46.2 mmol) was added dropwise to maintain an internal reaction temperature of 21-23° C., then the resulting mixture was stirred at that temperature for 22 h. The mixture was cooled to 5° C., then $H_2O$ (40 mL) was added and the resulting mixture was stirred for 10 min. Additional portions of $H_2O$ and EtOAc (40 mL each) were added, then the mixture was concentrated to remove THF. The layers were separated, and the aqueous was further extracted with EtOAc (3×100 mL). The combined organics were washed with $H_2O$, dried over $Na_2SO_4$, filtered, and concentrated to afford a solid foam (6.9 g). This sample was combined with another batch derived from an analogous reaction, to afford a total of 8.5 g of crude material. The combined solid foam was suspended in MTBE (100 mL) and was heated to 55° C. internal temperature for 4 h, then was held at 40° C. internal temperature for 40 min and was seeded with a sample of 2-(((1S,2R)-1-amino-2-ethylcyclopentyl)methoxy)-6-methoxy-4-(5-methoxyimidazo[1,2-a]pyridin-3-yl)benzonitrile, then was held at 21° C. for 4 days. The solids were collected by filtration to afford 2-(((1S,2R)-1-amino-2-ethylcyclopentyl)methoxy)-6-methoxy-4-(5-methoxyimidazo[1,2-a]pyridin-3-yl)benzonitrile as a tan solid (7.6 g). $^1H$ NMR (400 MHz, DMSO-$d_6$) δ 7.74 (s, 1H), 7.39 (dd, 1H), 7.29 (d, 1H), 6.89 (s, 1H), 6.88 (s, 1H), 6.45 (d, 1H), 3.96 (s, 2H), 3.95 (s, 3H), 3.93 (s, 3H), 1.89-1.10 (m, 9H), 0.87 (t, 3H). MS (M+H)+421.4. Chiral SFC: Chiral Technologies OZ-H, 250 mm×4.6 mm, 5μ; A: $CO_2$, B: 0.2% isopropylamine/EtOH, Gradient: 5% B for 0.5 min, then 5%-80% B over 5 min, then 80% B; 3.0 mL/min; 40° C.; 120 bar; 210 nM and MS detection; retention times, 2-(((1S,2R)-1-amino-2-ethylcyclopentyl)methoxy)-6-methoxy-4-(5-methoxyimidazo[1,2-a]pyridin-3-yl)benzonitrile (2A, 6.0 min), 2-(((1R,2S)-1-amino-2-ethylcyclopentyl)methoxy)-6-methoxy-4-(5-methoxyimidazo[1,2-a]pyridin-3-yl)benzonitrile (2B, 5.6 min), two enantiomers of trans 2-((1-amino-2-ethylcyclopentyl)methoxy)-6-methoxy-4-(5-methoxyimidazo[1,2-a]pyridin-3-yl)benzonitrile (5.7 min and 6.3 min); stereochemical purity>98%.

Biological Protocols

Enzyme Assay: Pan SIK MS IC50 Assay

Salt Induced Kinase (SIK) activity is determined by measuring the effect of a test agent on the activity of the appropriate SIK enzyme to phosphorylate its corresponding substrate. The substrate peptides AQT0868, AQT0252, and AQT0508 were engineered by AssayQuant to be specific for their corresponding enzymes SIK 1, SIK 2, and SIK 3 respectively. The phosphorylated substrate product resulting from the kinase reaction is detected by LCMS/MS, and the area under the peak curve correlates with kinase activity. Before initiating the assay, the assay ready plates (ARP) containing 0.15 μL compound in dose response format (10 μM to 9.5 pM by 4-fold dilution) are thawed for 20-30 minutes at room temperature. The plates are spun at 1000 rpm for 30 seconds to ensure compounds are at the bottom of the well before removing foil covers. 0.15 μL HPE (assay std) and ZPE (DMSO) are added to the ARP using an HP D300 dispenser. Plates are spun again at 1000 rpm for 30 seconds. 20 μL of 1.25× enzyme (one plate each for SIK 1, SIK 2, and SIK 3) with 1 mM ATP in reaction buffer (Reagent Grade Water, 50 mM Hepes pH 7.5, 0.5 mM EGTA, 10 mM MgCl2, 0.01% Brij-35, 1% Glycerol, 0.01% BSA, 1 mM TCEP) are added with a Multidrop Combi and designated small volume cassette. Plates are spun at 1000 rpm for 30 seconds. Plates are then sealed and incubated at RT for 10 minutes. Following incubation, 5 μL of 5× peptide reagent is added with a Multidrop Combi and designated small volume cassette to initiate the kinase reaction. Plates are spun at 1000 rpm for 30 seconds. Plates are then sealed and incubated at RT for 90 minutes. The assay is stopped by the addition of 5 μl of 120 mM EDTA added with a Multidrop Combi and designated small volume cassette (20 mM final concentration). Plates are spun at 1000 rpm for 30 seconds. 10 μl of the final reaction mix from each of the three individual enzyme plates are transferred by a Platemate Plus to the same corresponding 96 well deepwell plate containing 70 μl Water/Methanol (85/15%) for multiplex MS detection (100 μl total volume). Using Activity Base (ABase), an idbs data analysis software tool, the reported area ratio unit data is associated to compound, batch and dose information, the data is evaluated for quality, and the percent inhibition of each well is calculated. The data from each Max effect/HPE and Min effect/ZPE control wells are assessed, and outliers are excluded from all further calculations. The mean and standard deviation of the HPE and ZPE are then calculated for each plate, along with the Z Prime. The compound data is converted into % effect, using the average ZPE and HPE controls as 0% and 100% activity, respectively.

Cytokine Assays: SIK Macrophage Assay

Cytokine activity is determined by measuring the effect of a test agent on the inhibitory release of the cytokine TNFα and the increasing release of the cytokine IL10 from human monocyte derived macrophages (human macrophages) stimulated with lipopolysaccharide (LPS). At the time of assay, human macrophages (CGPS group Pfizer Groton, CT) are removed from cryopreservation, thawed quickly at 37° C., diluted in thaw medium (OptiMEM—Gibco medium, 10% heat inactivated fetal bovine serum (HIFBS)), and then centrifuged at 200×g for 10 minutes. The resulting cell pellet is re-suspended in assay medium (OptiMEM—Gibco medium, 0.5% HIFBS) to a concentration of approximately $0.56\times10^6$ cells/mL and 45 μL of this cell suspension (approximately 25,000 cells) is added to each well of a 384-well cell culture microtiter plate (Greiner) containing 0.05 μL of varying concentrations of test compound. After ~60 minutes in an incubator at 37° C. in a humidified environment in 5% carbon dioxide the cells are stimulated by the addition of 5 μL of LPS (10 ng/mL; Sigma) and the assay plate is returned to an incubator at 37° C. in a humidified environment in 5% carbon dioxide for 4 hours. The final assay conditions are approximately 25,000 human macrophages per well in assay medium containing 1 ng/mL LPS and the indicated final concentration of test compound (approximately 10 μM to 38 pM by 4-fold dilution). The final concentration of DMSO in the assay is approximately 0.1%. After 4 hours, the assay plate is removed from the incubator and centrifuged at 1500 rpm for 10 minutes. A portion of the resulting cell supernatant is then used to determine the amount of IL-10 and TNFα in each well. Cytokine measurements are made using human IL-10 and TNFα HTRF assay kits (Perkin Elmer) following the manufacturer's assay protocol. The concentrations and resulting effect values for tested compounds are plotted and the concentration of compound required for 50% effect (IC50) is determined with a four-parameter logistic dose response equation (IL10 data analysis uses E-WorkBook, and TNFα data analysis uses Activity base, ID Business Solutions Ltd.).

TABLE 1

| Ex. | SIK1 IC50 IC50 (nM) | SIK2 IC50 IC50 (nM) | SIK3 IC50 IC50 (nM) | TNFa IC50 (nM) | IL10 EC50 (nM) |
|---|---|---|---|---|---|
| 1 | 2.5 | 2.2 | 7.5 | 26.4 | 109 |
| 2A | 0.5 | 0.6 | 2.0 | 5.2 | 21 |
| 2B | 12.0 | 11.1 | 71.3 | 271.4 | 570 |
| 3 | 0.8 | 2.1 | 4.7 | 29.7 | 92 |
| 4A | 6.3 | 7.1 | 32.1 | 225.4 | 387 |
| 4B | 0.7 | 1.0 | 2.2 | 12.2 | 30 |
| 4C | 5.6 | 11.0 | 32.4 | 160.1 | 328 |
| 4D | 1.1 | 2.9 | 10.2 | 54.6 | 118 |
| 5A | 49.9 | 36.7 | 136.6 | 707.1 | 1211 |
| 5B | 1.6 | 1.4 | 3.9 | 15.1 | 64 |
| 6A | 0.7 | 0.9 | 2.5 | 22.7 | 66 |
| 6B | 0.1 | 0.3 | 0.8 | 0.5 | 2 |
| 7 | 0.5 | 0.8 | 1.8 | 1.5 | 5 |
| 8 | 1.1 | 1.0 | 3.3 | 11.1 | 23 |
| 9 | 0.9 | 1.1 | 2.0 | 5.3 | 12 |
| 10A | 3.5 | 5.3 | 16.4 | 67.3 | 88 |
| 10B | 0.3 | 0.5 | 1.0 | 1.7 | 9 |
| 11A | 0.2 | 0.7 | 1.3 | 3.6 | 19 |
| 11B | 0.2 | 0.5 | 1.6 | 6.3 | 39 |
| 11C | 13.4 | 21.0 | 63.5 | 346.4 | 715 |
| 11D | 9.1 | 21.7 | 81.2 | 559.0 | 1469 |
| 12 | 2.4 | 1.8 | 4.8 | 20.1 | 67 |
| 13A | 8.1 | 9.6 | 34.7 | 171.4 | 332 |
| 13B | 1.4 | 1.4 | 5.0 | 24.4 | 54 |
| 14 | 0.6 | 1.5 | 1.2 | 13.7 | 45 |
| 15A | 2.1 | 2.9 | 2.5 | 36.5 | 68 |
| 15B | 0.2 | 0.6 | 1.1 | 4.4 | 18 |
| 16 | 0.8 | 1.7 | 1.7 | 4.8 | 14 |
| 17A | 5.3 | 13.2 | 17.9 | 117.9 | 221 |
| 17B | 0.2 | 0.4 | 1.2 | 2.5 | 12 |
| 18 | 0.1 | 0.6 | 1.0 | 1.1 | 5 |
| 19A | 0.7 | 1.0 | 1.0 | 18.7 | 49 |
| 19B | 0.1 | 0.6 | 0.7 | 0.5 | 2 |
| 20A | 51.8 | 49.6 | 217.8 | 865.4 | 825 |
| 20B | 0.5 | 0.8 | 3.9 | 13.8 | 33 |
| 21A | 1.0 | 1.1 | 4.4 | 19.6 | 50 |
| 21B | 5.2 | 6.2 | 13.7 | 101.5 | 257 |
| 22 | 1.6 | 1.3 | 5.9 | 32.4 | 357 |
| 23A | 13.2 | 6.4 | 16.6 | 128.4 | 799 |
| 23B | 1.1 | 0.8 | 3.1 | 19.8 | 89 |
| 24A | 2.1 | 1.1 | 6.7 | 28.9 | 135 |
| 24B | 12.3 | 12.1 | 46.2 | 193.4 | 609 |
| 25 | 2.3 | 0.9 | 5.3 | 15.6 | 177 |
| 26A | 0.6 | 1.0 | 3.0 | 20.0 | 66 |
| 26B | 12.5 | 9.7 | 54.8 | 368.9 | 692 |
| 27 | 3.3 | 2.5 | 5.1 | 25.8 | 142 |
| 28A | 2.8 | 1.5 | 3.0 | 22.7 | 14 |
| 28B | 1.9 | 1.4 | 3.6 | 32.5 | 208 |
| 29 | 2.4 | 2.9 | 11.4 | 29.1 | 75 |
| 30A | 7.8 | 9.6 | 35.2 | 122.3 | 484 |
| 30B | 1.2 | 2.2 | 5.2 | 23.7 | 78 |
| 31 | 0.7 | 1.6 | 4.8 | 13.8 | 36 |
| 32A | 46.3 | 27.5 | 132.8 | 535.3 | 966 |
| 32B | 38.9 | 60.6 | 150.6 | 287.4 | 598 |

TABLE 1-continued

| Ex. | SIK1 IC50 IC50 (nM) | SIK2 IC50 IC50 (nM) | SIK3 IC50 IC50 (nM) | TNFa IC50 (nM) | IL10 EC50 (nM) |
|---|---|---|---|---|---|
| 32C | 0.5 | 0.8 | 2.0 | 4.9 | 21 |
| 32D | 0.7 | 1.2 | 1.5 | 11.4 | 34 |
| 33A | 0.6 | 1.0 | 2.2 | 13.9 | 34 |
| 33B | 10.9 | 9.9 | 23.4 | 258.4 | 338 |
| 34 | 1.2 | 0.9 | 1.8 | 6.9 | 28 |
| 35 | 0.5 | 0.2 | 0.7 | 4.9 | 23 |
| 36 | 1.2 | 0.8 | 2.1 | 4.8 | 35 |
| 37 | 0.3 | 0.4 | 0.9 | 3.9 | 27 |
| 38 | 1.5 | 1.0 | 1.8 | 20.1 | 51 |
| 39 | 0.5 | 1.0 | 1.1 | 6.0 | 25 |
| 40 | 0.4 | 0.6 | 1.6 | 6.1 | 17 |
| 41 | 1.9 | 0.8 | 0.7 | 5.3 | 54 |
| 42 | 3.0 | 0.9 | 2.2 | 10.7 | 85 |
| 43 | 0.2 | 0.4 | 1.1 | 0.6 | 2 |
| 44 | 2.3 | 1.7 | 2.1 | 21.0 | 38 |
| 45 | 0.1 | 0.2 | 0.4 | 0.6 | 3 |
| 46 | 0.8 | 1.5 | 2.8 | 6.9 | 28 |
| 47 | 0.2 | 0.4 | 0.9 | 1.4 | 6 |
| 48 | 0.4 | 0.7 | 1.7 | 0.8 | 4 |
| 49 | 0.9 | 0.7 | 2.4 | 6.5 | 18 |
| 50 | 1.2 | 0.5 | 0.8 | 4.2 | 29 |
| 51 | 1.5 | 0.5 | 1.6 | 5.7 | 26 |
| 52 | 5.1 | 1.1 | 2.1 | 12 | 178 |
| 53 | 0.1 | 0.4 | 1.5 | 0.5 | 4 |

The invention claimed is:

1. A compound of formula IA having the structure:

IA

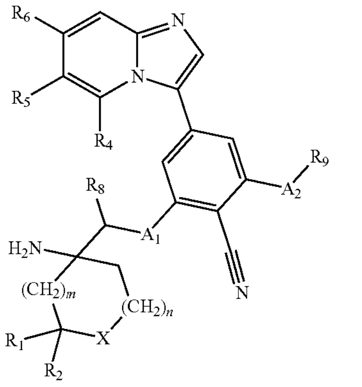

or a pharmaceutically acceptable salt thereof, wherein $A_1$ and $A_2$ are independently O or S;

X is selected from $CH_2$, $CD_2$, $NR_3$, O, and S, where $R_3$ is selected from hydrogen, $C_1$-$C_4$ linear or branched chain alkyl, halo($C_1$-$C_4$) linear or branched chain alkyl, and hydroxyl($C_1$-$C_4$) linear or branched chain alkyl;

$R_1$ and $R_2$ are independently selected from hydrogen, deuterium, $C_1$-$C_4$ linear or branched chain alkyl, halo ($C_1$-$C_4$) linear or branched chain alkyl, hydroxyl($C_1$-$C_4$) linear or branched chain alkyl, cyano ($C_1$-$C_4$) linear or branched chain alkyl, and $C_1$-$C_3$ alkoxy ($C_1$-$C_4$) linear or branched chain alkyl; or a $C_1$-$C_2$ alkyl substituted with a $C_3$-$C_5$ cycloalkyl ring; or taken together to form a $C_3$-$C_6$ cycloalkyl ring; or where X is $CH_2$ or $CD_2$, then $R_1$ and $R_2$ are independently selected from hydrogen, deuterium, halogen, hydroxyl, $C_1$-$C_4$ linear or branched chain alkyl, halo($C_1$-$C_4$) linear or branched chain alkyl, hydroxyl($C_1$-$C_4$) linear or branched chain alkyl, cyano ($C_1$-$C_4$) linear or branched chain alkyl, and $C_1$-$C_3$ alkoxy ($C_1$-$C_4$) linear or branched chain alkyl, and a $C_1$-$C_2$ alkyl substituted with a $C_3$-$C_5$ cycloalkyl ring;

$R_4$ is selected from hydrogen, deuterium, cyano, halogen, ($C_1$-$C_3$) alkoxy, halo($C_1$-$C_3$) alkoxy, $C_1$-$C_3$ alkyl-substituted thiol, $C_1$-$C_4$ linear or branched chain alkyl, halo($C_1$-$C_4$) linear or branched chain alkyl, and a hydroxyl($C_1$-$C_4$) linear or branched chain alkyl;

$R_5$ is selected from hydrogen, deuterium, halogen, $C_1$-$C_3$ alkoxy, amino, ($C_1$-$C_4$ linear or branched chain alkyl) amino, di($C_1$-$C_4$ linear or branched chain alkyl)amino, (4-6 membered) heterocyclic, $C_1$-$C_4$ linear or branched chain alkyl, halo($C_1$-$C_4$) linear or branched chain alkyl, and a hydroxyl($C_1$-$C_4$) linear or branched chain alkyl;

$R_6$ is selected from hydrogen, deuterium, halogen, $C_1$-$C_4$ linear or branched chain alkoxy, $CONH_2$, $C_1$-$C_4$ linear or branched chain alkyl, halo($C_1$-$C_4$) linear or branched chain alkyl, hydroxyl($C_1$-$C_4$) linear or branched chain alkyl, and $CO_2R_7$ where $R_7$ is selected from H and $C_1$-$C_4$ linear or branched chain alkyl;

$R_8$ is selected from hydrogen, deuterium, and $C_1$-$C_3$ linear or branched chain alkyl;

$R_9$ is selected from $C_1$-$C_3$ linear or branched chain alkyl, and a halo($C_1$-$C_3$) linear or branched chain alkyl; and, n and m are independently selected from 0, 1 and 2.

2. The compound of claim 1 or a pharmaceutically acceptable salt thereof, wherein $A_1$ is O.

3. The compound of claim 1 or a pharmaceutically acceptable salt thereof, wherein $A_2$ is O or S.

4. The compound of claim 1 or a pharmaceutically acceptable salt thereof, wherein $R_1$ and $R_2$ are independently selected from ethyl, methyl, and H.

5. The compound of claim 1 or a pharmaceutically acceptable salt thereof, wherein $R_4$ is cyano or methoxy.

6. The compound of claim 1 or a pharmaceutically acceptable salt thereof, wherein $R_5$ is H.

7. The compound of claim 1 or a pharmaceutically acceptable salt thereof, wherein $R_5$ is azetidine, pyrrolidine, or dimethylamino.

8. The compound of claim 1 or a pharmaceutically acceptable salt thereof, wherein $R_6$ is H.

9. The compound of claim 1 or a pharmaceutically acceptable salt thereof, wherein $R_8$ is H.

10. The compound of claim 1 or a pharmaceutically acceptable salt thereof, wherein $R_9$ is methyl.

11. The compound of claim 1 or a pharmaceutically acceptable salt thereof, wherein X is $CH_2$.

12. The compound of claim 1 or a pharmaceutically acceptable salt thereof, wherein X is O.

13. The compound of claim 1 or a pharmaceutically acceptable salt thereof, wherein m is 0 and n is 1.

14. The compound of claim 1 or a pharmaceutically acceptable salt thereof, wherein m is 1 and n is 1.

15. The compound of claim 1 selected from the group consisting of:

2-((1-Aminocyclopentyl) methoxy)-4-(5-methoxyimidazo[1,2-a]pyridin-3-yl)-6-(methylthio)benzonitrile;

2-(((1S,2R)-1-Amino-2-ethylcyclopentyl) methoxy)-6-methoxy-4-(5-methoxyimidazo[1,2-a]pyridin-3-yl) benzonitrile;

2-(((1R,2S)-1-Amino-2-ethylcyclopentyl) methoxy)-6-methoxy-4-(5-methoxyimidazo[1,2-a]pyridin-3-yl) benzonitrile;

2-((1-Amino-3-ethylcyclopentyl) methoxy)-6-methoxy-4-(5-methoxyimidazo[1,2-a]pyridin-3-yl)benzonitrile;

2-(((1R,3R)-1-Amino-3-ethylcyclopentyl) methoxy)-6-methoxy-4-(5-methoxyimidazo[1,2-a]pyridin-3-yl) benzonitrile;

2-(((1S,3S)-1-Amino-3-ethylcyclopentyl) methoxy)-6-methoxy-4-(5-methoxyimidazo[1,2-a]pyridin-3-yl) benzonitrile;

2-(((1R,3S)-1-Amino-3-ethylcyclopentyl) methoxy)-6-methoxy-4-(5-methoxyimidazo[1,2-a]pyridin-3-yl) benzonitrile;

2-(((1S,3R)-1-Amino-3-ethylcyclopentyl) methoxy)-6-methoxy-4-(5-methoxyimidazo[1,2-a]pyridin-3-yl) benzonitrile;

2-(((1S,2S)-1-Amino-2-ethylcyclopentyl) methoxy)-6-methoxy-4-(5-methoxyimidazo[1,2-a]pyridin-3-yl) benzonitrile;

2-(((1R,2R)-1-Amino-2-ethylcyclopentyl) methoxy)-6-methoxy-4-(5-methoxyimidazo[1,2-a]pyridin-3-yl) benzonitrile;

3-(3-(((1S,2R)-1-Amino-2-ethylcyclopentyl) methoxy)-4-cyano-5-(methylthio)phenyl) imidazo[1,2-a]pyridine-5-carbonitrile;

3-(3-(((1R,2S)-1-Amino-2-ethylcyclopentyl) methoxy)-4-cyano-5-(methylthio)phenyl) imidazo[1,2-a]pyridine-5-carbonitrile;

2-((1-Amino-2-ethylcyclopentyl) methoxy)-4-(5-methoxyimidazo[1,2-a]pyridin-3-yl)-6-(methylthio) benzonitrile;

2-(((1S,2R)-1-Amino-2-ethylcyclopentyl) methoxy)-4-(5-methoxyimidazo[1,2-a]pyridin-3-yl)-6-(methylthio) benzonitrile;

2-(((1R,2S)-1-amino-2-ethylcyclopentyl) methoxy)-4-(5-methoxyimidazo[1,2-a]pyridin-3-yl)-6-(methylthio) benzonitrile;

2-(((2S,3R)-3-Amino-2-ethyltetrahydrofuran-3-yl) methoxy)-4-(5-methoxyimidazo[1,2-a]pyridin-3-yl)-6-(methylthio)benzonitrile;

2-(((2R,3R)-3-Amino-2-ethyltetrahydrofuran-3-yl) methoxy)-4-(5-methoxyimidazo[1,2-a]pyridin-3-yl)-6-(methylthio)benzonitrile;

2-(((2R,3S)-3-Amino-2-ethyltetrahydrofuran-3-yl) methoxy)-4-(5-methoxyimidazo[1,2-a]pyridin-3-yl)-6-(methylthio)-benzonitrile;

2-(((2S,3S)-3-Amino-2-ethyltetrahydrofuran-3-yl) methoxy)-4-(5-methoxyimidazo[1,2-a]pyridin-3-yl)-6-(methylthio)benzonitrile;

(R)-3-(3-((1-Amino-3,3-difluorocyclopentyl) methoxy)-4-cyano-5-(methylthio)phenyl) imidazo[1,2-a]pyridine-5-carbonitrile;

(S)-3-(3-((1-amino-3,3-difluorocyclopentyl) methoxy)-4-cyano-5-(methylthio)phenyl) imidazo[1,2-a]pyridine-5-carbonitrile;

(R)-2-((1-Amino-3,3-difluorocyclopentyl) methoxy)-4-(5-methoxyimidazo[1,2-a]pyridin-3-yl)-6-(methylthio) benzonitrile;

(S)-2-((1-Amino-3,3-difluorocyclopentyl) methoxy)-4-(5-methoxyimidazo[1,2-a]pyridin-3-yl)-6-(methylthio) benzonitrile;

(R)-3-(3-((1-Amino-3,3-dimethylcyclohexyl) methoxy)-4-cyano-5-(methylthio)phenyl) imidazo[1,2-a]pyridine-5-carbonitrile;

(S)-3-(3-((1-amino-3,3-dimethylcyclohexyl) methoxy)-4-cyano-5-(methylthio)phenyl) imidazo[1,2-a]pyridine-5-carbonitrile;

2-(((1R,3R)-1-Amino-3-ethylcyclohexyl) methoxy)-6-methoxy-4-(5-methoxyimidazo[1,2-a]pyridin-3-yl) benzonitrile;

2-(((1S,3S)-1-Amino-3-ethylcyclohexyl) methoxy)-6-methoxy-4-(5-methoxyimidazo[1,2-a]pyridin-3-yl) benzonitrile;

3-(3-(((1S,3S)-1-Amino-3-ethylcyclohexyl) methoxy)-4-cyano-5-(methylthio)phenyl) imidazo[1,2-a]pyridine-5-carbonitrile;

3-(3-(((1R,3R)-1-Amino-3-ethylcyclohexyl) methoxy)-4-cyano-5-(methylthio)phenyl) imidazo[1,2-a]pyridine-5-carbonitrile;

(S)-2-((1-Aminospiro [4.4]nonan-1-yl) methoxy)-6-methoxy-4-(5-methoxyimidazo[1,2-a]pyridin-3-yl) benzonitrile;

(R)-2-((1-Aminospiro[4.4]nonan-1-yl) methoxy)-6-methoxy-4-(5-methoxyimidazo[1,2-a]pyridin-3-yl) benzonitrile;

(S)-2-((3-Amino-1-(2,2,2-trifluoroethyl) piperidin-3-yl) methoxy)-6-methoxy-4-(5-methoxyimidazo[1,2-a] pyridin-3-yl)benzonitrile;

(R)-2-((3-Amino-1-(2,2,2-trifluoroethyl) piperidin-3-yl) methoxy)-6-methoxy-4-(5-methoxyimidazo[1,2-a] pyridin-3-yl)benzonitrile;

(R)-2-((3-Aminotetrahydrothiophen-3-yl) methoxy)-4-(imidazo[1,2-a]pyridin-3-yl)-6-(methylthio)benzonitrile;

(S)-2-((3-Aminotetrahydrothiophen-3-yl) methoxy)-4-(imidazo[1,2-a]pyridin-3-yl)-6-(methylthio)benzonitrile;

(R)-2-((3-Aminotetrahydrofuran-3-yl) methoxy)-4-(5-methoxyimidazo[1,2-a]pyridin-3-yl)-6-(methylthio) benzonitrile;

(S)-2-((3-Aminotetrahydrofuran-3-yl) methoxy)-4-(5-methoxyimidazo[1,2-a]pyridin-3-yl)-6-(methylthio) benzonitrile;

(R)-2-((1-Amino-3,3-difluorocyclopentyl) methoxy)-4-(imidazo[1,2-a]pyridin-3-yl)-6-(methylthio)benzonitrile;

(S)-2-((1-Amino-3,3-difluorocyclopentyl) methoxy)-4-(imidazo[1,2-a]pyridin-3-yl)-6-(methylthio)benzonitrile;

(R)-3-(3-((3-Aminotetrahydrothiophen-3-yl) methoxy)-4-cyano-5-(methylthio)phenyl) imidazo[1,2-a]pyridine-5-carbonitrile;

(S)-3-(3-((3-Aminotetrahydrothiophen-3-yl) methoxy)-4-cyano-5-(methylthio)phenyl) imidazo[1,2-a]pyridine-5-carbonitrile;

2-((1-Aminocyclohexyl) methoxy)-4-(5-methoxyimidazo [1,2-a]pyridin-3-yl)-6-(methylthio)benzonitrile;

(R)-2-((3-Aminotetrahydrothiophen-3-yl) methoxy)-4-(5-methoxyimidazo[1,2-a]pyridin-3-yl)-6-(methylthio) benzonitrile;

(S)-2-((3-Aminotetrahydrothiophen-3-yl) methoxy)-4-(5-methoxyimidazo[1,2-a]pyridin-3-yl)-6-(methylthio) benzonitrile;

2-(((1S)-1-Amino-3-(methoxymethyl)cyclohexyl) methoxy)-4-(imidazo[1,2-a]pyridin-3-yl)-6-(methylthio)benzonitrile;

2-(((1R)-1-Amino-3-(methoxymethyl)-cyclohexyl) methoxy)-4-(imidazo[1,2-a]pyridin-3-yl)-6-(methylthio)benzonitrile;

2-(((1S,2S)-1-Amino-2-(cyclopropylmethyl)cyclopentyl) methoxy)-6-methoxy-4-(5-methoxyimidazo[1,2-a] pyridin-3-yl)benzonitrile;

2-(((1R,2R)-1-Amino-2-(cyclopropylmethyl)cyclopentyl) methoxy)-6-methoxy-4-(5-methoxyimidazo[1,2-a] pyridin-3-yl)benzonitrile;

2-(((1S,2R)-1-Amino-2-(cyclopropylmethyl)cyclopentyl) methoxy)-6-methoxy-4-(5-methoxyimidazo[1,2-a] pyridin-3-yl)benzonitrile;

2-(((1R,2S)-1-Amino-2-(cyclopropylmethyl)cyclopentyl) methoxy)-6-methoxy-4-(5-methoxyimidazo[1,2-a] pyridin-3-yl)benzonitrile;

2-(((1S,3S)-1-Amino-3-(trifluoromethyl)cyclohexyl) methoxy)-4-(imidazo[1,2-a]pyridin-3-yl)-6-(methylthio)benzonitrile;

2-(((1R,3R)-1-Amino-3-(trifluoromethyl)cyclohexyl) methoxy)-4-(imidazo[1,2-a]pyridin-3-yl)-6-(methylthio)benzonitrile;

2-(((1R,3S)-1-Amino-3-(trifluoromethyl)cyclohexyl) methoxy)-4-(imidazo[1,2-a]pyridin-3-yl)-6-(methylthio)benzonitrile;

2-(((1S,3R)-1-Amino-3-(trifluoromethyl)cyclohexyl) methoxy)-4-(imidazo[1,2-a]pyridin-3-yl)-6-(methylthio)benzonitrile;

3-(3-((1-Aminocyclohexyl) methoxy)-4-cyano-5-(methylthio)phenyl) imidazo[1,2-a]pyridine-5-carbonitrile;

3-(3-((1-Aminocyclopentyl) methoxy)-4-cyano-5-(methylthio)phenyl) imidazo[1,2-a]pyridine-5-carbonitrile;

3-(3-((1-Aminocyclopentyl) methoxy)-4-cyano-5-(methylthio)phenyl) pyrazolo[1,5-a]pyridine-4-carbonitrile;

Ethyl 3-(3-((1-aminocyclopentyl) methoxy)-4-cyano-5-(methylthio)phenyl)-5-cyanoimidazo[1,2-a]pyridine-7-carboxylate;

3-(3-((1-Aminocyclopentyl) methoxy)-4-cyano-5-(methylthio)phenyl)-6-methoxyimidazo[1,2-a]pyridine-5-carbonitrile;

3-(3-((1-Aminocyclopentyl) methoxy)-4-cyano-5-(methylthio)phenyl)-7-methylimidazo[1,2-a]pyridine-5-carbonitrile;

3-(3-((1-Aminocyclopentyl) methoxy)-4-cyano-5-(methylthio)phenyl)-6-(dimethylamino) imidazo[1,2-a]pyridine-5-carbonitrile;

3-(3-((1-Aminocyclopentyl) methoxy)-4-cyano-5-(methylthio)phenyl)-6-ethylimidazo[1,2-a]pyridine-5-carbonitrile;

3-(3-((1-Aminocyclopentyl) methoxy)-4-cyano-5-(methylthio)phenyl)-6-methylimidazo[1,2-a]pyridine-5-carbonitrile;

3-(3-((1-Aminocyclopentyl) methoxy)-4-cyano-5-(methylthio)phenyl)-7-chloroimidazo[1,2-a]pyridine-5-carbonitrile;

3-(3-((1-Aminocyclohexyl) methoxy)-4-cyano-5-(methylthio)phenyl) pyrazolo[1,5-a]pyridine-4-carbonitrile;

6-Amino-3-(3-((1-aminocyclopentyl) methoxy)-4-cyano-5-(methylthio)phenyl) imidazo[1,2-a]pyridine-5-carbonitrile;

3-(3-((1-Aminocyclopentyl) methoxy)-4-cyano-5-(methylthio)phenyl)-6-(azetidin-1-yl) imidazo[1,2-a]pyridine-5-carbonitrile;

3-(3-((1-Aminocyclopentyl) methoxy)-4-cyano-5-(methylthio)phenyl)-6-(pyrrolidin-1-yl) imidazo[1,2-a]pyridine-5-carbonitrile;

3-(3-((1-Aminocyclopentyl) methoxy)-4-cyano-5-methoxyphenyl)-6-(dimethylamino) imidazo[1,2-a] pyridine-5-carbonitrile;

3-(3-((1-Aminocyclohexyl) methoxy)-4-cyano-5-(methylthio)phenyl)-6-methoxyimidazo[1,2-a]pyridine-5-carbonitrile;

3-(3-((1-Aminocyclopentyl) methoxy)-4-cyano-5-(methylthio)phenyl)-7-methoxyimidazo[1,2-a]pyridine-5-carbonitrile;

3-(3-((1-Aminocyclohexyl) methoxy)-4-cyano-5-(methylthio)phenyl)-7-methoxyimidazo[1,2-a]pyridine-5-carbonitrile;

3-(3-((1-Aminocyclohexyl) methoxy)-4-cyano-5-methoxyphenyl)-7-methoxyimidazo[1,2-a]pyridine-5-carbonitrile; and 3-(3-((1-Aminocyclopentyl) methoxy)-4-cyano-5-(methylthio)phenyl)-6-(methylamino) imidazo[1,2-a]pyridine-5-carbonitrile or, a pharmaceutically acceptable salt thereof.

16. The compound of claim 1 selected from the group consisting of:

3-(3-((1-Aminocyclohexyl) methoxy)-4-cyano-5-(methylthio)phenyl) imidazo[1,2-a]pyridine-5-carbonitrile;

2-(((1S,2R)-1-Amino-2-ethylcyclopentyl) methoxy)-6-methoxy-4-(5-methoxyimidazo[1,2-a]pyridin-3-yl) benzonitrile;

2-(((2S,3R)-3-Amino-2-ethyltetrahydrofuran-3-yl) methoxy)-4-(5-methoxyimidazo[1,2-a]pyridin-3-yl)-6-(methylthio)benzonitrile;

3-(3-(((1S,2R)-1-Amino-2-ethylcyclopentyl) methoxy)-4-cyano-5-(methylthio)phenyl) imidazo[1,2-a]pyridine-5-carbonitrile; and 3-(3-((1-aminocyclopentyl) methoxy)-4-cyano-5-(methylthio)phenyl)-6-(dimethylamino) imidazo[1,2-a]pyridine-5-carbonitrile;

or, a pharmaceutically acceptable salt thereof.

17. 3-(3-((1-Aminocyclohexyl) methoxy)-4-cyano-5-(methylthio)phenyl) imidazo[1,2-a]pyridine-5-carbonitrile; or, a pharmaceutically acceptable salt thereof.

18. 2-(((1S,2R)-1-Amino-2-ethylcyclopentyl) methoxy)-6-methoxy-4-(5-methoxyimidazo[1,2-a]pyridin-3-yl)benzonitrile; or, a pharmaceutically acceptable salt thereof.

19. 2-(((2S,3R)-3-Amino-2-ethyltetrahydrofuran-3-yl) methoxy)-4-(5-methoxyimidazo[1,2-a]pyridin-3-yl)-6-(methylthio)benzonitrile; or, a pharmaceutically acceptable salt thereof.

20. 3-(3-(((1S,2R)-1-Amino-2-ethylcyclopentyl) methoxy)-4-cyano-5-(methylthio)phenyl) imidazo[1,2-a] pyridine-5-carbonitrile; or, a pharmaceutically acceptable salt thereof.

21. 3-(3-((1-Aminocyclopentyl) methoxy)-4-cyano-5-(methylthio)phenyl)-6-(dimethylamino) imidazo[1,2-a]pyridine-5-carbonitrile; or, a pharmaceutically acceptable salt thereof.

22. A pharmaceutical composition comprising a compound according to claim 1, or a pharmaceutically acceptable salt thereof, or a pharmaceutically acceptable solvate of said compound or salt, and a pharmaceutically acceptable excipient.

* * * * *